(12) United States Patent
Stevens et al.

(10) Patent No.: US 7,144,893 B2
(45) Date of Patent: Dec. 5, 2006

(54) 4-ARYL QUINOLS AND ANALOGS THEREOF AS THERAPEUTIC AGENTS

(75) Inventors: Malcolm Francis Graham Stevens, Nottingham (GB); Geoffrey Wells, London (GB); Andrew David Westwell, Nottingham (GB); Tracey Dawn Poole, Nottingham (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 10/482,912

(22) PCT Filed: Jul. 5, 2002

(86) PCT No.: PCT/GB02/03097

§ 371 (c)(1),
(2), (4) Date: Apr. 27, 2004

(87) PCT Pub. No.: WO03/004479

PCT Pub. Date: Jan. 16, 2003

(65) Prior Publication Data

US 2004/0220236 A1 Nov. 4, 2004

(30) Foreign Application Priority Data

Jul. 6, 2001 (GB) ................................. 0116594.3

(51) Int. Cl.
  *A61K 31/47* (2006.01)
  *A61K 31/425* (2006.01)
  *C07D 217/02* (2006.01)
  *C07D 277/62* (2006.01)
  *C07D 333/16* (2006.01)

(52) U.S. Cl. ........................ 514/307; 514/312; 514/367; 514/365; 514/374; 514/375; 514/412; 514/394; 514/396; 546/144; 546/173; 546/344; 548/178; 548/224; 548/302.7; 549/78; 549/469

(58) Field of Classification Search ................ 514/307, 514/312, 367, 365, 374, 375, 394, 396, 412; 546/144, 173, 344; 548/178, 224, 302.7; 549/78, 469

See application file for complete search history.

(56) References Cited

U.S. PATENT DOCUMENTS

| 4,357,345 A | * | 11/1982 | Moore | 514/461 |
| 4,535,165 A | * | 8/1985 | Moore | 548/204 |
| 5,391,570 A | | 2/1995 | Catt et al. | |
| 6,153,611 A | | 11/2000 | Mattson et al. | |

FOREIGN PATENT DOCUMENTS

| EP | 0 469 984 | | 2/1992 |
| EP | 0 546 583 | | 6/1993 |
| EP | 0 546 583 A | | 6/1993 |
| WO | 83/01775 | * | 5/1983 |
| WO | 01/92239 A | | 12/2001 |
| WO | WO 01/92239 | | 12/2001 |
| WO | WO 03/004479 | | 1/2003 |

OTHER PUBLICATIONS

DeCosta, Chemical Abstracts 117:191642, 1992, abstract of J of the Chem Soc, Perkin Trans 1: Organic and Bio-org Chem, (1972-1999), vol. 13, pp. 1671-1680, 1992.*
Wada, Chemical Abstracts 109:3771, abstract of Chem & Pharm Bull, vol. 35(12), p. 4757-4762, 1987.*
Fukushima, Chemical Abstract 72:21599, abstract of Yakugaku Zasshi, vol. 89(9), pp. 1272-1275, 1969.*
Noro, Chemical Abstracts 71:81092, abstract of Yakugaku Zasshi, vol. 89(6), pp. 851-856, 1969.*
NL 6513784, Chemical Abstracts 65:82177, abstract only, 1966.*
Minz, CA 93:222093, abstract of Kemia=Kemi, 7(9), 477-480, 1980.*
Ershov, CA 59:3192, abstract of Izvestiya akademii nauk sssr, Seriya Khimicheskaya, pp. 157-161, 1963.*
Alcaraz, L., et al., 1998, "Manumycin A: synthesis of the (+)-enantiomer and revision of stereochemical assignment," *J. Org. Chem.*, vol. 63, pp. 3526-3527.

(Continued)

*Primary Examiner*—D. Margaret Seaman
(74) *Attorney, Agent, or Firm*—Nixon & Vanderhye P.C.

(57) ABSTRACT

The present invention pertains to compounds of the formula (1) which are, inter alia, antiproliferative agents, anticancer agents, antimycobacterial agents, antituberculosis agents, and/or thioredoxin/thioredoxin reductase inhibitor: wherein: Q is =O or =N—S(=O)$_2$—R$^Q$; R$^Q$ is —H or optionally substituted C$_{1-7}$alkyl, C$_{3-20}$heterocyclyl, or C$_{5-20}$aryl; Ar is optionally substituted C$_{5-20}$aryl; R$^O$ is an oxy substituent; the bond marked α is a single bond or a double bond; the bond marked β is a single bond or a double bond; R$^3$ and R$^5$ are each independently ring substituents; R$^2$ and R$^6$ are each independently ring substituents; and pharmaceutically acceptable salts, esters, amides, solvates, hydrates, and protected forms thereof. The present invention also pertains to pharmaceutical compositions comprising such compounds, and the use of such compounds and compositions, both in vitro and in vivo, for example, in the treatment of proliferative conditions, (e.g., cancer), mycobacterial infections (e.g., tuberculosis), and/or conditions mediated by thioredoxin/thioredoxin reductase

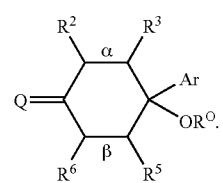

(1)

45 Claims, 3 Drawing Sheets

OTHER PUBLICATIONS

Alley et al., 1988, "Feasibility of drug screening with panels of human tumor cell lines using a microculture tetrazolium assay," *Cancer Research*, vol. 48, pp. 589-601.

Boyd, M.R., Paull, K.D., 1995, "Some practical considerations and applications of the National Cancer Institute in vitro anticancer drug discovery system," *Drug Dev. Res.*, vol. 34, pp. 91-104.

Callinan et al., 1990, "Spiro-annulated 2,5-cyclohexadienones via oxidation 2'-alkenyl-p-phenyl phenols with iodobenzene diacetate," *Tetraderon Letters*, vol. 31, No. 32, pp. 4551-4552.

Capparelli et al., 1987, "Structural and solvent/electrolyte effects on the selectivity and efficiency of the anodic oxidation of para-substituted aromatic ethers. An efficient route to quinol ether ketals and quinol ethers," *J. Org. Chem.*, vol. 52, pp. 4953-4961.

Collins, L.; Franzblau, S.G.; 1997, "Microplate Alamar Blue Assay versus BACTEC 460 System for High-throughput Screening of Compounds against *Mycobacterium tuberculosis* and *Mycobacterium avium*,"*Antimicrob. Agents Chemother.*, vol. 41, pp. 1004-1009.

Dengler et al., 1995, "Development of a propidium iodide fluorescence assay for proliferation and cytotoxicity assays," *Anti-cancer drugs*, vol. 6, pp. 522-532.

Faaland et al., 1991, "Rapid uptake to tyrphostin into A431 human epidermoid cells is followed by delayed inhibition of epidermal growth factor (EGF) stimulated EFG receptor tyrosine kinase activity," *Mol. Cell Biol.*, vol. 11, pp. 2697-2703.

Gasdaska et al., 1994, "The predicted amino acid sequence of human thioredoxin is identical to that of the autocrine growth factor human adult T-cell derived cofactor (ADF): thioredoxin mRNA is elevated in some human tumors," *Biochimica et Biophysica Acta*, vol. 1218, pp. 292-296.

Geran et al., 1972, "Protocols for screening chemical agents and natural products against tumor and other biological systems," *Cancer Chemother. Rep.*, vol. 3, No. 2, pp. 1-103.

Hutchinson et al., 2001, Antitumour benzothiazoles. 14. Synthesis and in vitro biological properties of fluroinated 2-(4-aminophenyl)benzothiazoles, *J. Med. Chem.*, vol. 44, pp. 1446-1455.

Kirkpatrick et al., 1999, "Parallel synthesis of disulfide inhibitors of the thioredoxin redox system as potential antitumor agents," *Anti-Cancer Drug Design*, vol. 14, pp. 421-432.

Kunkel et al., 1997, "Cell-line-directed screening assay for inhibitors of thioredoxin reductase signaling as potential anti-cancer drugs," *Anti-Cancer Drug Design*, vol. 12, pp. 659-670.

McKillop et al., 1993, "A concise synthesis of the novel antibiotic aranorosin," *Tetrahedron Lett.*, vol. 34, pp. 5519-5522.

Milić, D. R., et al., "X-Ray crystal structure of 10β-hydroxy-4β,5β-epoxyestr-1-en-3,17-dione and antitumor activity of its congeners," *Molecules*, vol. 4, pp. 338-352.

Oblong et al., 1993, "Purification of human thioreductase; properties and characterization by absorption and circular dichroism spectroscopy," *Biochemistry*, vol. 32, pp. 7271-7277.

Pelter, A., Elgendy, S.M.A., 1993, "Phenolic oxidations with phenyliodonium diacetate," *J. Chem. Soc., Perkin Trans. 1*, pp. 1891-1896.

Powis, G., Mustacich, D, Coon, A., 2000, "The role of the redox protein thioredoxin in cell growth and cancer," Free Radical Biology & Medicine, vol. 29, Nos. 3/4, pp. 312-322.

Rambas et al., 1994, "The degree of inhibition of protein tyrosine kinase activity by activity by Tyrphostin 23 and 25 is related to their instability," *Cancer Research*, vol. 54, pp. 867-869.

Reddy et al., 1992, "Inhibition of breast cancer cell growth in vitro by a tyrosine kinase inhibitor," *Cancer Research*, vol. 52, pp. 3631-3641.

Sonnenwirth, A.C., and Jarett, L. (eds.), Gradwohl's Clinical Laboratory Methods and Diagnosis, 8th edition, vol. 2, pp. 1707-1708.

Umezawa et al., 1991, "Use of erbstatin as protein tyrosine kinase inhibitor," *Methods Enzymol.*, vol. 201, pp. 379-385.

Wada, H., et al., 1987, "Chemical and chemotaxonomical studies of ferns. LXXIII. New flavonoids with modified B-ring from the genus Pseudophegopteris (Thelypteridacae)," *Chem. Pharm. Bull.*, vol. 35, pp. 4757-4762.

Weinstein, J. N., et al., 1997, "An information-intensive approach to the molecular pharmacology of cancer," *Science*, vol. 275, pp. 343-349.

Wells et al., Mar. 6, 2000, "Antitumour benzothiazoles. Part 10: The synthesis and antitumour activity of benzothiazole substituted quinol derivatives," *Bioorganic & Medicinal Chemistry Letters*, vol. 10, No. 5, pp. 513-515.

Wessely et al., 1952, "Uber die Elnwirkung von metallorganischen Verbingungen auf Chinole I," *Monatsch. Chem.*, vol. 83, pp. 1253-1261.

Wipf, P., et al., "Synthesis of the antitumor antibiotic LL-C10037α," *J. Org. Chem.*, vol. 59, pp. 3518-3519.

Takeya et al; "Total Synthesis of (+/−)-Plumbazeylanone, A Naphthoquinone Trimer from Plubago Zeylanica"; Chemical and Pharmaceutical Bulletin, vol. 47, No. 2, 1999, pp. 209-219, XP002215315.

Dodge et al; "Competitive Dienone-Phenol Type Rearrangements for the Regioselective Preparation of 2,4-Disubstituted-NAPHT-1-OLS"; Tetrahedron Letters, Elsevier Science, vol. 29, No. 38, 1988, pp. 4827-4830, XP002201194.

Well et al; Antitumor Benzothiazoles. Part 10: The Synthesis and Antitumor Activity of Benzothiazole Quinol Derivatives; Bioorganic & Medicinal Chemistry Letters, vol. 10, 2000, pp. 513-515, XP002215316.

Hutchinson, et al; "Antitumor Benzothiazoles. 14. Synthesis and In Vitro Biological Properties of Fluorinated 2-(4-Aminophenyl)Benzothiazoles"; Journal of Medicinal Chemistry, vol. 44, 2001, pp. 1446-1455, XP002215317.

* cited by examiner

4-ARYL QUINOLS AND ANALOGS THEREOF AS THERAPEUTIC AGENTS

This application is the US national phase of international application PCT/GB02/03097 filed in English on 05 Jul. 2002, which designated the US. PCT/GB02/03097 claims priority to GB Application No. 0116594.3 filed 06 Jul. 2001. The entire contents of these applications are incorporated herein by reference.

RELATED APPLICATION

This application is related to (and where permitted by law, claims priority to) United Kingdom patent application GB 0116594.3 filed 06 Jul. 2001, the contents of which are incorporated herein by reference in their entirety.

TECHNICAL FIELD

This invention pertains generally to the field of therapeutic agents, and more specifically to certain 4-aryl-cyclohexa-2,5-dienone compounds (4-aryl quinols), and analogs thereof, which are, inter alia, antiproliferative agents, anticancer agents, antimycobacterial agents, antituberculosis agents, and/or thioredoxin/thioredoxin reductase inhibitors. The present invention also pertains to compositions comprising such compounds, and the use of such compounds and compositions, both in vitro and in vivo, for example, in the treatment of proliferative conditions, cancer, mycobacterial infections (e.g., tuberculosis), and/or conditions mediated by thioredoxin/thioredoxin reductase.

BACKGROUND

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiments.

Phenolic xenobiotics can be modified by cellular systems in a number of ways, e.g., oxidation, glucoronidation, sulphation, methylation, acetylation, etc., and the instability of certain phenolic protein tyrosine kinase (PTK) inhibitors has been documented. For example, the antitumor PTK inhibitor erbstatin, shown below, is known to have a short half-life (<30 min) in fetal calf serum (see, e.g., Umezawa et al., 1991), and the lack of correlation between the activity of tyrphostins, shown below, against isolated enzymes and their effects in vitro and in vivo, is noteworthy (see, e.g., Rambas et al., 1994). Di- and tri-phenolic tyrphostins decompose in solution to more active PTK inhibitors (see, e.g., Faaland et al., 1991), whereas tyrphostins devoid of hydroxy groups have a rapid onset of cellular activity (see, e.g., Reddy et al., 1992), implicating metabolic oxidation to a quinone (or other) moiety as a possible bioactivating step.

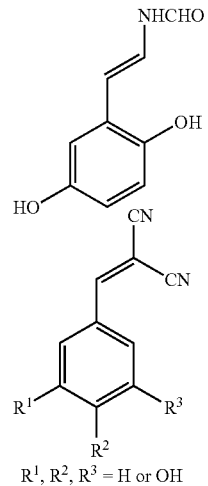

The present invention pertains to compounds which may be considered to be the oxidation products of bioactive phenols, and analogues thereof. Such oxidation products include, e.g., optionally substituted 4-aryl-cyclohexa-2,5-dienones (4-aryl quinols), 4-aryl-4-substituted-cyclohexa-2-enones, 4-aryl-4-substituted-cyclohexanones, sulfonamide analogs, and the like.

Callinan et al., 1990, describe the synthesis of certain phenyl substituted quinol ethers, shown below, where R is, for example, —H, -Me, —OMe, —CH=CH$_2$.

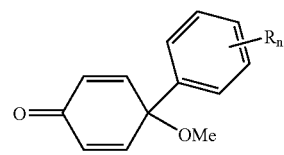

Weesely et al., 1952, describe the synthesis of certain substituted quinols, shown below, where R is, for example, —H or —Ac; R$^1$ is -Me or -Ph; and R$^2$ and R$^3$ are —H or -Me.

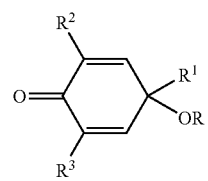

Capparelli et al., 1987, describe the synthesis of certain substituted quinols, shown below, where, for example, R is —H or -Me; R$^1$ is -Et, -iPr, -tBu, —CH$_2$Ph, -Ph, methyl or methoxy subsituted -Ph, or thiophen-2-yl; R$^2$ is —H or -Me; and, R$^3$ is —H or —OMe.

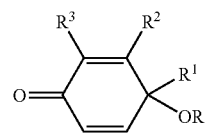

Wells et al., 2000, describe several benzothiazole substituted quinol derivatives, shown below, where R$^1$ is —Ac, -Me, -Et, -nPr, or —CH$_2$C≡CH (denoted herein as Q5, Q15, Q16, Q17, Q18, Q19, and Q20, respectively), and R$^2$ is -Me or -Et. These compounds were reported to have activity against certain colon (HCT-116 and HT29) and breast (MCF-7 and MDA468) cancer cell lines in vitro. Note that there is no mention of possible application to Mycobacteria infections, or as thioredoxin/thioredoxin reductase inhibitors.

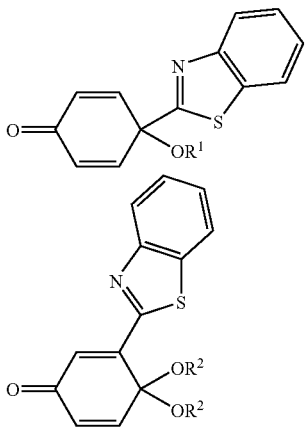

Two compounds that contain a hydroxycyclohexadienone structure and which apparently have antitumor activity have been reported: a hydroxylated flavone-substituted quinol (i.e., a chromone substituted quinol) (see, e.g., Wada et al., 1987) and an oxidized estrone (see, e.g., Milic et al., 1999).

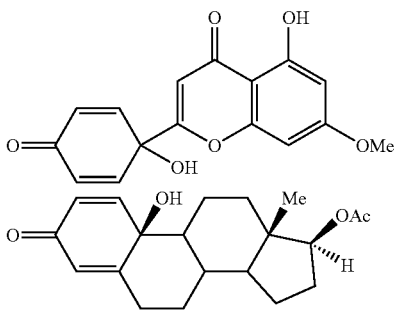

Several related antitumor epoxyquinols, such as Manumycin A (see, e.g., Alcaraz et al., 1998) and LL-C 10037α (see, e.g., Wipf et al., 1994) are known.

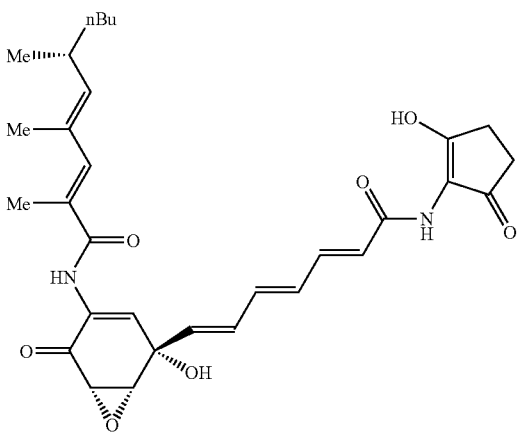

-continued

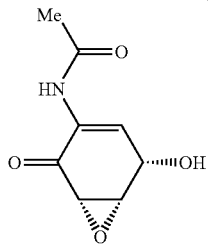

SUMMARY OF THE INVENTION

Figure 1:
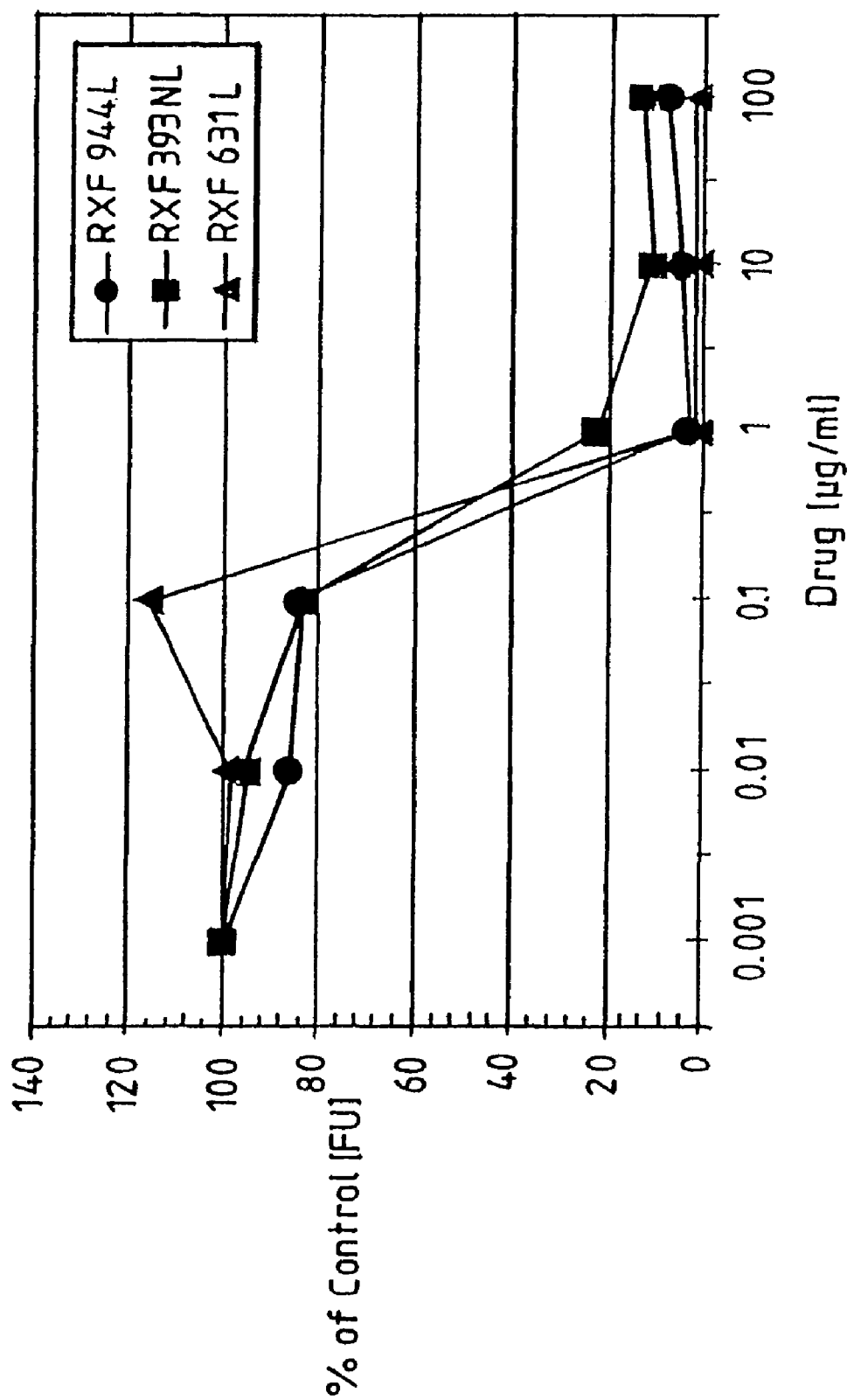
FIG. 1 is a graph of % of control (fluorescence units) (one representative of three independent experiments) versus drug concentration (μg/mL) for the compound under study, Q05, and shows dose response curves for three renal carcinoma cell lines, hypernephroma RXF 944L (▲) followed by RXF 631L (▼) and RXF 393NL (■).

One aspect of the invention pertains to novel compounds as described herein.

Another aspect of the invention pertains to a composition comprising an active compound as described herein and a pharmaceutically acceptable carrier or diluent.

Another aspect of the invention pertains to an active compound as described herein for use in a method of treatment of the human or animal body.

Another aspect of the invention pertains to use of an active compound as described herein for the manufacture of a medicament for use in the treatment of, for example, a proliferative condition (e.g., cancer), a mycobacterial condition (e.g., tuberculosis), a condition mediated by thioredoxin/thioredoxin reductase, etc.

Another aspect of the invention pertains to a method of inhibiting thioredoxin/thioredoxin reductase, in vitro or in vivo, comprising contacting a cell with an effective amount of an active compound as described herein.

Another aspect of the invention pertains to a method of regulating cell proliferation, in vitro or in vivo, comprising contacting a cell with an effective amount of an active compound as described herein.

Another aspect of the invention pertains to a method of (a) inhibiting cell proliferation; (b) inhibiting cell cycle progression; (c) promoting apoptosis; or (d) a combination of one or more of these, in vitro or in vivo, comprising contacting a cell with an effective amount of a compound as described herein.

Another aspect of the invention pertains to a method for the treatment of, for example, a proliferative condition (e.g., cancer), a mycobacterial condition (e.g., tuberculosis), a condition mediated by thioredoxin/thioredoxin reductase, etc., comprising administering to a subject suffering from said condition a therapeutically-effective amount of an active compound, as described herein.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention pertains compounds having the following formula:

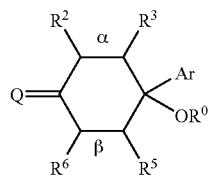

(1)

wherein:

Q is =O or =N—S(=O)$_2$—R$^Q$;

R$^Q$ is —H or optionally substituted C$_{1-7}$alkyl, C$_{3-20}$heterocyclyl, or C$_{5-20}$aryl;

Ar is optionally substituted C$_{5-20}$aryl;

R$^O$ is an oxy substituent;

the bond marked α is a single bond or a double bond;

the bond marked β is a single bond or a double bond;

R$^3$ and R$^5$ are each independently ring substituents;

R$^2$ and R$^6$ are each independently ring substituents; and, and pharmaceutically acceptable salts, esters, amides, solvates, hydrates, and protected forms thereof.

In one embodiment:

R$^O$ is —H or optionally substituted C$_{1-7}$alkyl, C$_{3-20}$heterocyclyl, C$_{5-20}$aryl, C$_{1-7}$alkyl-acyl, C$_{3-20}$heterocyclyl-acyl, or C$_{5-20}$aryl-acy;

each of the ring substituents, R$^3$, R$^4$, R$^5$, and R$^6$, is:

(a) H;

or:

(b) a ring substituent which, together with an adjacent ring substituent, and together with the ring atoms to which these ring substituents are attached, form a fused ring;

or:

(c) a divalent monodentate substituent selected from optionally substituted C$_{1-7}$alkylidene and C$_{5-20}$aryl-C$_{1-7}$alkylidene;

and if one or both of R$^2$ and R$^3$ is a divalent monodentate group, then α is a single bond;

and if one or both of R$^5$ and R$^6$ is a divalent monodentate group, then β is a single bond.

or:

(d) a monovalent monodentate substituent;

with the proviso that, if Q is =O, α is a double bond, β is a double bond, each of R$^2$, R$^3$, R$^5$, and R$^6$ is —H; and Ar is benzothiazol-2-yl, then R$^O$ is other than: -Me, -Et, —Pr, —CH$_2$—C≡CH, and —C(=O)CH$_3$; and, with the proviso that, if Q is =O, α is a double bond, β is a double bond, then Ar is other than: phenyl, substituted phenyl, thiophenyl, chromone, or substituted chromone.

Provisos

Insofar as the present invention pertains to compounds, per se, these compounds are as defined herein, with certain provisos, as stated herein. However, some or all of these provisos do not apply to the present invention in its other aspects, for example, as it pertains to pharmaceutical compositions comprising the compounds, methods of treatment (e.g., of one or more particular indications) employing the compounds, the compounds for medical use, use of the compounds in the preparation of medicaments, and the like.

Optical Isomers

Note that, in these compounds, one, two, three, four, or five of the ring atoms (marked with an asterisk (*) in the following formula) may be chiral (for example, depending on the bonds α and β, and the substituents, R$^3$ and R$^5$, and R$^2$ and R$^6$) and if so, may be in R or S configuration. Unless otherwise specified, the resulting optical isomers (discussed below) are encompassed by the corresponding structure, which is silent as to configuration.

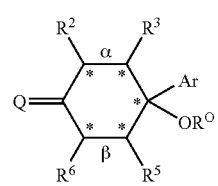

The Bonds, α and β

The bond marked α is a single bond or a double bond;

and the bond marked β is a single bond or a double bond.

In one embodiment:

the bond marked α is a double bond; and the bond marked β is a double bond.

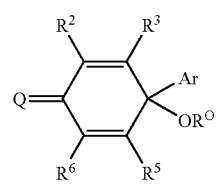

(2)

In one embodiment:

the bond marked α is a single bond; and the bond marked β is a double bond.

(3)

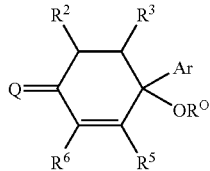

In one embodiment:

the bond marked α is a double bond; and the bond marked β is a single bond.

(4)

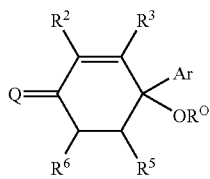

In one embodiment:

the bond marked α is a single bond; and the bond marked β is a single bond.

(5)

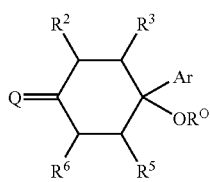

The Carbonyl Group or Sulfonyl-Imino Group, Q

The group Q is =O or =N—S(=O)$_2$—R$^Q$.

In one embodiment, Q is =O.

In one embodiment, the compounds have the following formula:

(6)

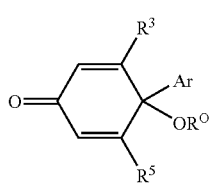

In one embodiment, the compounds have the following formula:

(7)

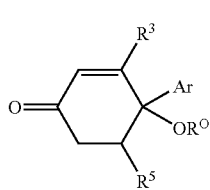

In one embodiment, the compounds have the following formula:

(8)

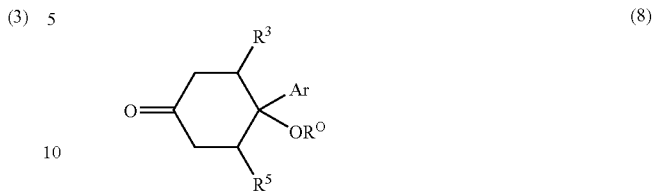

In one embodiment, Q is =N—S(=O)$_2$—R$^Q$.

In one embodiment, the compounds have the following formula:

(9)

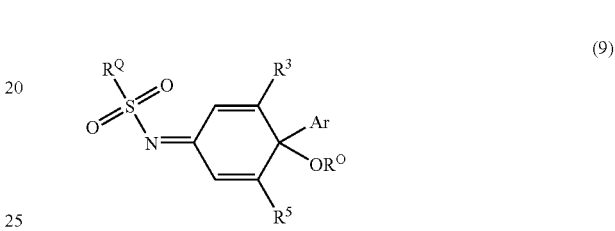

In one embodiment, the compounds have the following formula:

(10)

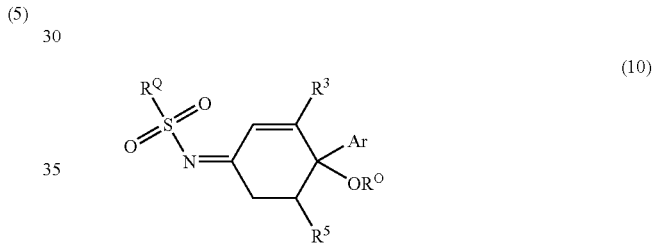

In one embodiment, the compounds have the following formula:

(11)

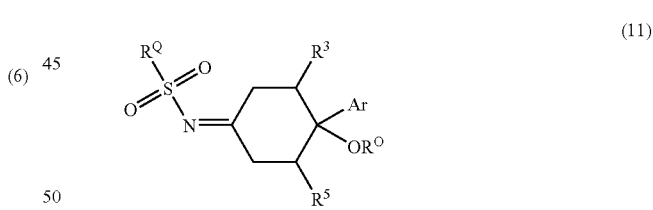

The Sulfonyl-Imino Substituent, R$^Q$

In one embodiment, Q is =N—S(=O)$_2$—R$^Q$. In such cases, R$^Q$ is —H or optionally substituted $C_{1-7}$alkyl, $C_{3-20}$heterocyclyl, or $C_{5-20}$aryl.

Examples of suitable R$^Q$ groups include, but are not limited to, methyl, ethyl, phenyl, tolyl, and halo-substituted analogs thereof (e.g., halo-substituted methyl, ethyl, etc.).

Oxy Subsitutents, R$^O$

In one embodiment, the oxy substituent, R$^O$, is —H, or is other than —H.

In one embodiment, the oxy substituent, R$^O$, is other than —H.

In one embodiment, the oxy substituent, R$^O$, is —H.

Oxy Subsitutent, R$^O$, is —H

In one embodiment, the oxy substituent, R$^O$, is —H.

In one embodiment, the oxy substituent, $R^O$, is —H; the ring substituents, $R^2$ and $R^6$, are both —H; and Q, Ar, $R^3$, $R^5$, α, and β are as defined herein, and the compounds have the following formula:

(12)

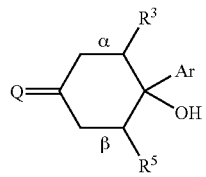

In one embodiment, the oxy substituent, $R^O$, is —H; the ring substituents, $R^2$ and $R^6$, are both —H; Q is =O; and Ar, $R^3$, $R^5$, α, and β are as defined herein, and the compounds have the following formula:

(13)

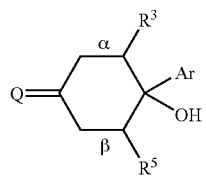

In one embodiment, the oxy substituent, $R^O$, is —H; the ring substituents, $R^2$ and $R^6$, are both —H; and Q, Ar, $R^3$, and $R^5$ are as defined herein, and the compounds have the following formula:

(14)

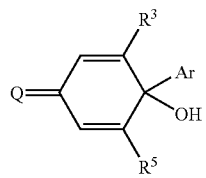

In one embodiment, the oxy substituent, $R^O$, is —H; the ring substituents, $R^2$ and $R^6$, are both —H; and Q, Ar, $R^3$, and $R^5$ are as defined herein, and the compounds have the following formula:

(15)

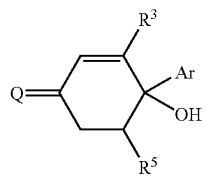

In one embodiment, the oxy substituent, $R^O$, is —H; the ring substituents, $R^2$ and $R^6$, are both —H; and Q, Ar, $R^3$, and $R^5$ are as defined herein, and the compounds have the following formula:

(16)

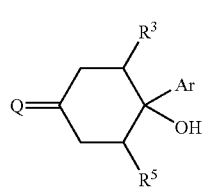

In one embodiment, the oxy substituent, $R^O$, is —H; Q is =O; the ring substituents, $R^2$ and $R^6$, are both —H; and Ar, $R^3$, and $R^5$ are as defined herein, and the compounds have the following formula:

(17)

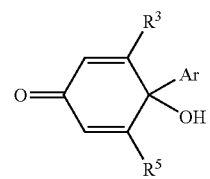

In one embodiment, the oxy substituent, $R^O$, is —H; Q is =O; the ring substituents, $R^2$ and $R^6$, are both —H; and Ar, $R^3$, and $R^5$ are as defined herein, and the compounds have the following formula:

(18)

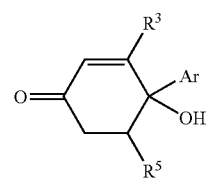

In one embodiment, the oxy substituent, $R^O$, is —H; Q is =O; the ring substituents, $R^2$ and $R^6$, are both —H; and Ar, $R^3$, and $R^5$ are as defined herein, and the compounds have the following formula:

(19)

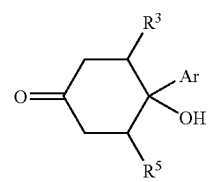

In one embodiment, the oxy substituent, $R^O$, is —H; $R^3$ and $R^5$ are both —H; the ring substituents, $R^2$ and $R^6$, are both —H; and Q and Ar is as defined herein, and the compounds have the following formula:

(20)

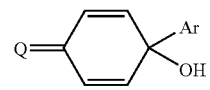

In one embodiment, the oxy substituent, $R^O$, is —H; $R^3$ and $R^5$ are both —H; the ring substituents, $R^2$ and $R^6$, are both —H; and Q and Ar is as defined herein, and the compounds have the following formula:

(21)

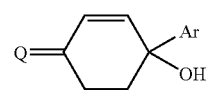

In one embodiment, the oxy substituent, $R^O$, is —H; $R^3$ and $R^5$ are both —H; the ring substituents, $R^2$ and $R^6$, are both —H; and Q and Ar is as defined herein, and the compounds have the following formula:

(22)

In one embodiment, the oxy substituent, $R^O$, is —H; $R^3$ and $R^5$ are both —H; Q is =O; the ring substituents, $R^2$ and $R^6$, are both —H; and Ar is as defined herein, and the compounds have the following formula:

(23)

In one embodiment, the oxy substituent, $R^O$, is —H; $R^3$ and $R^5$ are both —H; Q is =O; the ring substituents, $R^2$ and $R^6$, are both —H; and Ar is as defined herein, and the compounds have the following formula:

(24)

In one embodiment, the oxy substituent, $R^O$, is —H; $R^3$ and $R^5$ are both —H; Q is =O; the ring substituents, $R^2$ and $R^6$, are both —H; and Ar is as defined herein, and the compounds have the following formula:

(25)

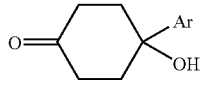

In one embodiment, the oxy substituent, $R^O$, is —H; either (a) α is a double bond; β is a single bond; $R^3$ is —H; and $R^5$ is other than —H; or (b) α is a single bond; β is a double bond; $R^3$ is other than —H; $R^5$ is —H; and, the ring substituents, $R^2$ and $R^6$, are both —H; Q and Ar are as defined herein, and the compounds have one of the following formulae:

(26)

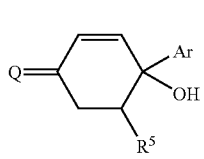

(27)

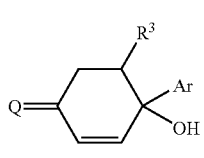

In one embodiment, the oxy substituent, $R^O$, is —H; either (a) α is a double bond; β is a single bond; $R^3$ is —H; and $R^5$ is other than —H; or (b) α is a single bond; β is a double bond; $R^3$ is other than —H; $R^5$ is —H; and, the ring substituents, $R^2$ and $R^6$, are both —H; Q is =O; and Ar is as defined herein, and the compounds have one of the following formulae:

(28)

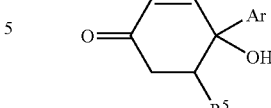

(29)

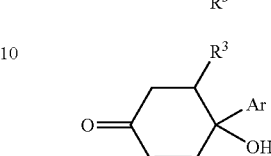

In one embodiment, the oxy substituent, $R^O$, is —H; α is a single bond; β is a single bond; $R^3$ and $R^5$ are both other than —H; the ring substituents, $R^2$ and $R^6$, are both —H; and Q and Ar are as defined herein, and the compounds have the following formula:

(30)

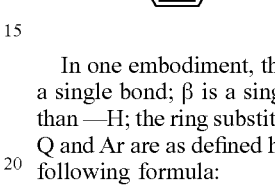

In one embodiment, the oxy substituent, $R^O$, is —H; α is a single bond; β is a single bond; $R^3$ and $R^5$ are both other than —H; Q is =O; the ring substituents, $R^2$ and $R^6$, are both —H; and Ar is as defined herein, and the compounds have the following formula:

(31)

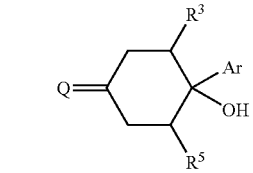

Oxy Substituent, $R^O$, is Other Than —H

In one embodiment, the oxy substituent, $R^O$, is other than —H.

When $R^O$ is other than —H, it may be, for example, $C_{1-7}$alkyl, $C_{3-20}$heterocyclyl, $C_{5-20}$aryl (i.e., —$OR^O$ is an ether); acyl (i.e., —$OR^O$ is an ester), for example, $C_{1-7}$alkyl-acyl, $C_{3-20}$heterocyclyl-acyl, or $C_{5-20}$aryl-acyl; and is optionally substituted.

In one embodiment, $R^O$ is an amino-alkyl-acyl group, of the formula —C(=O)-J-K, wherein J is a $C_{1-7}$alkylene group, and K is an amino group. In one embodiment, $R^O$ is —C(=O)(CH$_2$)$_n$—K, where n is an integer from 1 to 7, preferably 1 to 3, and K is an amino group. For example, in one embodiment, $R^O$ is —C(=O)CH$_2$CH$_2$CH$_2$NH$_2$.

Oxy Substituent, $R^O$: Provisos

In one embodiment, the compounds are as described herein, with the proviso that $R^O$ is other than: $C_{1-7}$alkyl and $C_{1-7}$alkyl-acyl.

In one embodiment, the compounds are as described herein, with the proviso that $R^O$ is other than: -Me, -Et, —Pr, —CH$_2$—C≡CH, and —C(=O)CH$_3$.

In one embodiment, the compounds are as described herein, with the proviso that, if Ar is benzothiazol-2-yl, then $R^O$ is other than: $C_{1-7}$alkyl and $C_{1-7}$alkyl-acyl.

In one embodiment, the compounds are as described herein, with the proviso that, if Ar is benzothiazol-2-yl, then $R^O$ is other than: -Me, -Et, —Pr, —CH$_2$—C≡CH, and —C(=O)CH$_3$.

In one embodiment, the compounds are as described herein, with the proviso that, if Q is =O and Ar is benzothiazol-2-yl, then $R^O$ is other than: $C_{1-7}$alkyl and $C_{1-7}$alkyl-acyl.

In one embodiment, the compounds are as described herein, with the proviso that, if Q is =O and Ar is benzothiazol-2-yl, then $R^O$ is other than: -Me, -Et, —Pr, —CH$_2$—C≡CH, and —C(=O)CH$_3$.

In one embodiment, the compounds are as described herein, with the proviso that, if Q is =O, α is a double bond, β is a double bond, and Ar is benzothiazol-2-yl, then $R^O$ is other than: $C_{1-7}$alkyl and $C_{1-7}$alkyl-acyl.

In one embodiment, the compounds are as described herein, with the proviso that, if Q is =O, α is a double bond, β is a double bond, and Ar is benzothiazol-2-yl, then $R^O$ is other than: -Me, -Et, —Pr, —CH$_2$—C≡CH, and —C(=O)CH$_3$.

In one embodiment, the compounds are as described herein, with the proviso that, if Q is =O, α is a double bond, β is a double bond, each of $R^2$, $R^3$, $R^5$, and $R^6$ is —H; and Ar is benzothiazol-2-yl, then $R^O$ is other than: $C_{1-7}$alkyl and $C_{1-7}$alkyl-acyl.

In one embodiment, the compounds are as described herein, with the proviso that, if Q is =O, α is a double bond, β is a double bond, each of $R^2$, $R^3$, $R^5$, and $R^6$ is —H; and Ar is benzothiazol-2-yl, then $R^O$ is other than: -Me, -Et, —Pr, —CH$_2$—C≡CH, and —C(=O)CH$_3$.

Where compatible, any of the above provisos may be combined with a proviso as described for the aryl substituent, Ar.

The Aryl Group, Ar

The aryl group, Ar, is a $C_{5-20}$aryl group, and is optionally substituted.

In one embodiment, the aryl group, Ar, is a $C_{5-20}$heteroaryl group, and is optionally substituted.

In one embodiment, the aryl group, Ar, is a monocyclic or bicyclic $C_{5-20}$aryl group, and is optionally substituted.

In one embodiment, the aryl group, Ar, is a monocyclic or bicyclic $C_{5-20}$heteroaryl group, and is optionally substituted.

In one embodiment, the aryl group, Ar, is a monocyclic $C_{5-6}$aryl group, and is optionally substituted.

In one embodiment, the aryl group, Ar, is a bicyclic $C_{8-10}$aryl group, and is optionally substituted.

In one embodiment, the aryl group, Ar, is a monocyclic $C_{5-6}$heteroaryl group, and is optionally substituted.

In one embodiment, the aryl group, Ar, is a bicyclic $C_{8-10}$heteroaryl group, and is optionally substituted.

In one embodiment, the aryl group, Ar, is a bicyclic $C_{8-10}$aryl group, a monocyclic $C_{5-6}$heteroaryl group, or a bicyclic $C_{8-10}$heteroaryl group, and is optionally substituted.

In one embodiment, the aryl group, Ar, is a bicyclic $C_{8-10}$aryl group, or a bicyclic $C_{8-10}$heteroaryl group, and is optionally substituted.

In one embodiment, the aryl group, Ar, is one of the following groups, and is optionally substituted:

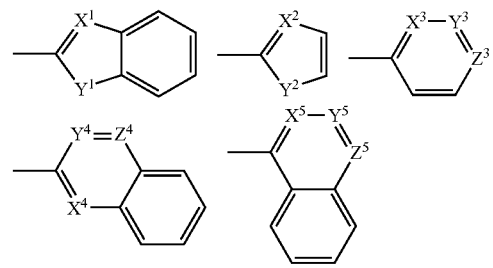

wherein:
$X^1$ is =CH— or =N—;
$Y^1$ is —NR$^N$—, —O—, or —S—;
$X^2$ is =CH— or =N—;
$Y^2$ is NR$^N$—, —O—, or —S—;
$X^3$ is =CH— or =N—;
$Y^3$ is —CH= or —N=;
$Z^3$ is =CH— or =N—;
$X^4$ is =CH— or =N—;
$Y^4$ is —CH= or —N=;
$Z^4$ is =CH— or =N—;
$X^5$ is =CH— or =N—;
$Y^5$ is —CH= or —N=; and,
$Z^5$ is =CH— or =N—.

In one embodiment:
$X^1$ is =CH— and $Y^1$ is —NR$^N$-(indol-2-yl); or,
$X^1$ is =CH— and $Y^1$ is —O-(benzofuran-2-yl); or,
$X^1$ is =CH— and $Y^1$ is —S-(benzothiophen-2-yl); or,
$X^1$ is =N— and $Y^1$ is —NR$^N$-(benzimidazol-2-yl); or,
$X^1$ is =N— and $Y^1$ is —O-(benzoxazol-2-yl); or
$X^1$ is =N— and $Y^1$ is —S-(benzothiazol-2-yl).

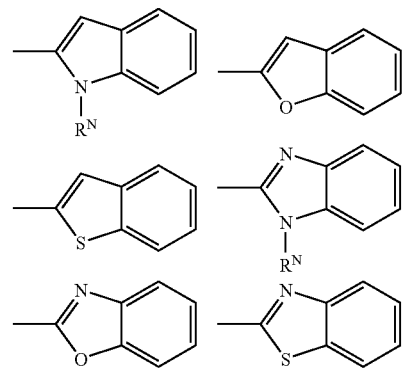

In one embodiment:
$X^2$ is =CH— and $Y^2$ is —NR$^N$-(pyrrol-2-yl); or,
$X^2$ is =CH— and $Y^2$ is —O-(furan-2-yl); or,
$X^2$ is =CH— and $Y^2$ is —S-(thiophen-2-yl); or,
$X^2$ is =N— and $Y^2$ is —NR$^N$-(imidazol-2-yl); or,
$X^2$ is =N— and $Y^2$ is —O-(oxazol-2-yl); or,
$X^2$ is =N— and $Y^2$ is —S-(thiazol-2-yl).

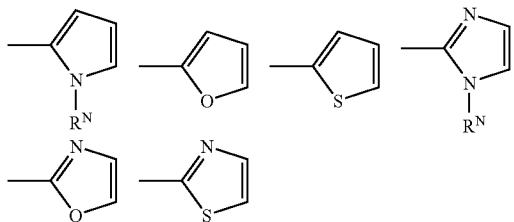

In one embodiment:
$X^3$ is =CH—; $Y^3$ is —CH=; and, $Z^3$ is =CH-(phenyl); or,
$X^3$ is =N—; $Y^3$ is —CH=; and, $Z^3$ is =CH-(pyrid-2-yl); or,
$X^3$ is =CH—; $Y^3$ is —N=; and, $Z^3$ is =CH-(pyrid-3-yl); or,
$X^3$ is =CH—; $Y^3$ is —CH=; and, $Z^3$ is =N-(pyrid-4-yl).

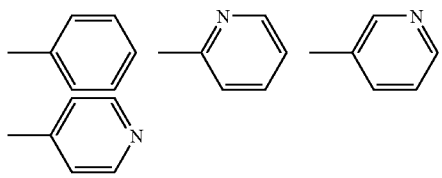

In one embodiment:
$X^3$ is =N—; $Y^3$ is —CH=; and, $Z^3$ is =CH-(pyrid-2-yl); or,
$X^3$ is =CH—; $Y^3$ is —N=; and, $Z^3$ is =CH-(pyrid-3-yl); or,
$X^3$ is =CH—; $Y^3$ is —CH=; and, $Z^3$ is =N-(pyrid-4-yl).

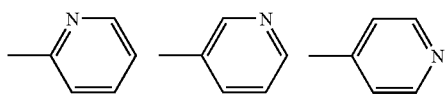

In one embodiment:
$X^4$ is =CH—; $Y^4$ is —CH=; and, $Z^4$ is =CH-(naphth-2-yl); or,
$X^4$ is =N—; $Y^4$ is —CH=; and, $Z^4$ is =CH-(quinolin-2-yl); or,
$X^4$ is =CH—; $Y^4$ is —N=; and, $Z^4$ is =CH-(isoquinolin-3-yl); or,
$X^4$ is =CH—; $Y^4$ is —CH=; and, $Z^4$ is =N-(quinolin-3-yl).

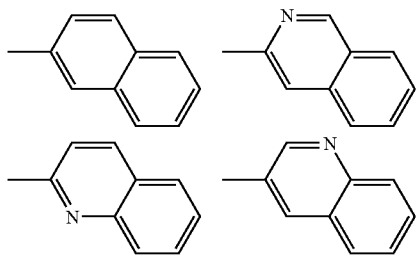

In one embodiment:
$X^5$ is =CH—; $Y^5$ is —CH=; and, $Z^5$ is =CH-(naphth-1-yl); or,
$X^5$ is =N—; $Y^5$ is —CH=; and, $Z^5$ is =CH-(isoquinolin-1-yl); or,
$X^5$ is =CH—; $Y^5$ is —N=; and, $Z^5$ is =CH-(isoquinolin-4-yl); or,
$X^5$ is =CH—; $Y^5$ is —CH=; and, $Z^5$ is =N-(quinolin-4-yl).

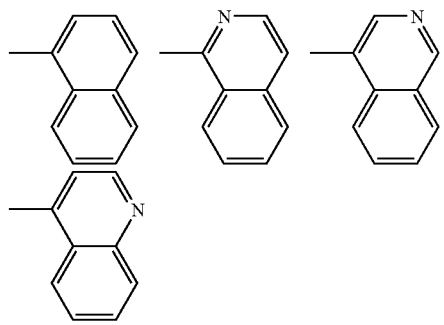

In one embodiment, the aryl group, Ar, is one of the following groups, and is optionally substituted:

[Structures of indole, benzofuran, benzothiophene, benzimidazole, benzoxazole, benzothiazole]

Nitrogen Substituent, $R^N$

In the above formulae, the nitrogen substituent, $R^N$, is —H, $C_{1-7}$alkyl, $C_{3-20}$heterocyclyl, or $C_{5-20}$aryl.

In one embodiment, the nitrogen substituent, $R^N$, is —H or $C_{1-5}$alkyl, including, e.g., $C_{1-5}$cycloalkyl, amino-substituted $C_{1-5}$alkyl.

Aryl Group, Ar: Provisos

In one embodiment, the compounds are as described herein, with the proviso that Ar is other than: phenyl or substituted phenyl.

In one embodiment, the compounds are as described herein, with the proviso that Ar is other than: phenyl, substituted phenyl, or thiophenyl.

In one embodiment, the compounds are as described herein, with the proviso that Ar is other than: phenyl, substituted phenyl, thiophenyl, chromone, or substituted chromone.

In one embodiment, the compounds are as described herein, with the proviso that, if Q is =O, then Ar is other than: phenyl or substituted phenyl.

In one embodiment, the compounds are as described herein, with the proviso that, if Q is =O, then Ar is other than: phenyl, substituted phenyl, or thiophenyl.

In one embodiment, the compounds are as described herein, with the proviso that, if Q is =O, then Ar is other than: phenyl, substituted phenyl, thiophenyl, chromone, or substituted chromone.

In one embodiment, the compounds are as described herein, with the proviso that, if Q is =O, α is a double bond, and β is a double bond, then Ar is other than: phenyl or substituted phenyl.

In one embodiment, the compounds are as described herein, with the proviso that, if Q is =O, α is a double bond, and β is a double bond, then Ar is other than: phenyl, substituted phenyl, or thiophenyl.

In one embodiment, the compounds are as described herein, with the proviso that, if Q is =O, α is a doublebond, and β is a double bond, then Ar is other than: phenyl, substituted phenyl, thiophenyl, chromone, or substituted chromone.

In one embodiment, the compounds are as described herein, with the proviso that, if Q is =O and $R^O$ is —H, then Ar is other than: phenyl or substituted phenyl.

In one embodiment, the compounds are as described herein, with the proviso that, if Q is =O and $R^O$ is —H, then Ar is other than: phenyl, substituted phenyl, or thiophenyl.

In one embodiment, the compounds are as described herein, with the proviso that, if Q is =O and $R^O$ is —H, then Ar is other than: phenyl, substituted phenyl, thiophenyl, chromone, or substituted chromone.

In one embodiment, the compounds are as described herein, with the proviso that, if Q is =O, $R^O$ is —H, α is a double bond, and β is a double bond, then Ar is other than: phenyl or substituted phenyl.

In one embodiment, the compounds are as described herein, with the proviso that, if Q is =O, $R^O$ is —H, α is a double bond, and β is a double bond, then Ar is other than: phenyl, substituted phenyl, or thiophenyl.

In one embodiment, the compounds are as described herein, with the proviso that, if Q is =O, $R^O$ is —H, α is a double bond, and β is a double bond, then Ar is other than: phenyl, substituted phenyl, thiophenyl, chromone, or substituted chromone.

In one embodiment, the compounds are as described herein, with the proviso that, if Q is =O, $R^3$ is —H, $R^5$ is —H, and $R^O$ is —H, then Ar is other than: phenyl or substituted phenyl.

In one embodiment, the compounds are as described herein, with the proviso that, if Q is =O, $R^3$ is —H, $R^5$ is —H, and $R^O$ is —H, then Ar is other than: phenyl, substituted phenyl, or thiophenyl.

In one embodiment, the compounds are as described herein, with the proviso that, if Q is =O, $R^3$ is —H, $R^5$ is —H, and $R^O$ is —H, then Ar is other than: phenyl, substituted phenyl, thiophenyl, chromone, or substituted chromone.

In one embodiment, the compounds are as described herein, with the proviso that, if Q is =O, α is a double bond, β is a double bond, $R^3$ is —H, $R^5$ is —H, and $R^O$ is —H, then Ar is other than: phenyl or substituted phenyl.

In one embodiment, the compounds are as described herein, with the proviso that, if Q is =O, α is a double bond, β is a double bond, $R^3$ is —H, $R^5$ is —H, and $R^O$ is —H, then Ar is other than: phenyl, substituted phenyl, or thiophenyl.

In one embodiment, the compounds are as described herein, with the proviso that, if Q is =O, α is a double bond, β is a double bond, $R^3$ is —H, $R^5$ is —H, and $R^O$ is —H, then Ar is other than: phenyl, substituted phenyl, thiophenyl, chromone, or substituted chromone.

Where compatible, any of the above provisos may be combined with a proviso as described for the oxy substituent, $R^O$.

Optional Substituents for Aryl Groups

As discussed above, the aryl group, Ar, is optionally substituted.

Examples of aryl substituents include, but are not limited to, the following:

halo; hydroxy; ether (e.g., $C_{1-7}$alkoxy); formyl; acyl (e.g., $C_{1-7}$alkylacyl, $C_{5-20}$arylacyl); carboxy; ester; acyloxy; amido; acylamido; thioamido; tetrazolyl; amino; nitro; azido; cyano; cyanato; thiocyano; isothiocyano; sulfhydryl; thioether (e.g., $C_{1-7}$alkylthio); sulfonic acid; sulfonate; sulfonyl; sulfonyloxy; sulfinyloxy; sulfamino; sulfonamino; sulfinamino; sulfamyl; sulfonamido; $C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; and $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

Examples of preferred aryl substituents include, but are not limited to, the following:

halo; hydroxy; ether (e.g., $C_{1-7}$alkoxy); formyl; acyl (e.g., $C_{1-7}$alkylacyl, $C_{5-20}$arylacyl); carboxy; ester; acyloxy; amido; acylamido; amino; sulfonyl; sulfonamido; $C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; and $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

Examples of preferred aryl substituents include, but are not limited to, the following:

halo; $C_{1-7}$alkyl; $C_{1-7}$haloalkyl; $C_{1-7}$alkoxy; $C_{1-7}$haloalkoxy; and sulfonyl.

In one embodiment, aryl substituents include, but are not limited to, the following:

—F, —Cl, —Br, —I, -Me, -Et, —CF$_3$, —CCl$_3$, —OMe, —OEt, —SO$_2$Me, and —SO$_2$Et.

Aryl Group: Benzothiazoles

In one embodiment, the aryl group, Ar, is the following group, and is optionally substituted:

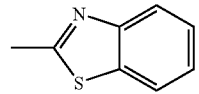

In one embodiment, the aryl group, Ar, is the following group, wherein m is an integer from 0 ro 4, and each $R^A$ is independently an aryl substituent, for example, as described herein under the heading "Optional Substituents for Aryl Groups":

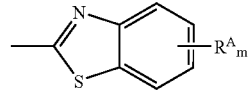

In one embodiment, m is 0, 1, 2, 3, or 4.
In one embodiment, m is 0, 1, 2, or 3.
In one embodiment, m is 0, 1, or 2.
In one embodiment, m is 0 or 1.
In one embodiment, m is 1, 2, 3, or 4.
In one embodiment, m is 1, 2, or 3.
In one embodiment, m is 1 or 2.
In one embodiment, m is 4.
In one embodiment, m is 3.
In one embodiment, m is 2.
In one embodiment, m is 1.

In one embodiment, α, β, $R^2$, $R^3$, $R^5$, $R^6$, Q, $R^O$, m, and $R^A$ are as defined herein, and the compounds have the following formula:

(32)

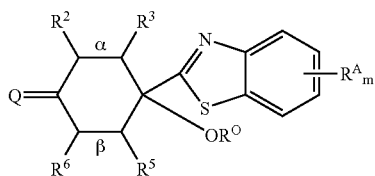

In one embodiment, α is a double bond; β is a double bond; $R^2$, $R^3$, $R^5$, $R^6$, Q, $R^O$, m, and $R^A$ are as defined herein, and the compounds have the following formula:

(33)

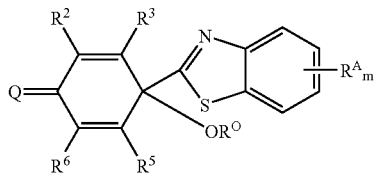

In one embodiment, α is a double bond; β is a double bond; the ring substituents, $R^3$ and $R^5$ are both —H; the ring substituents, $R^2$ and $R^6$, are both —H; and Q, $R^O$, m, and $R^A$ are as defined herein, and the compounds have the following formula:

(34)

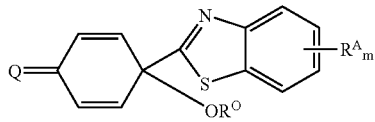

In one embodiment, α is a double bond; β is a double bond; the ring substituents, $R^3$ and $R^5$ are both —H; the ring substituents, $R^2$ and $R^6$, are both —H; Q is =O; and $R^O$, m, and $R^A$ are as defined herein, and the compounds have the following formula:

(35)

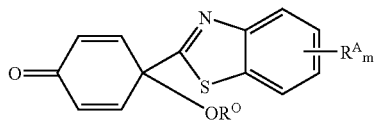

In one embodiment, $R^O$ is —H; and α, β, $R^2$, $R^3$, $R^5$, $R^6$, Q, m, and $R^A$ are as defined herein, and the compounds have the following formula:

(36)

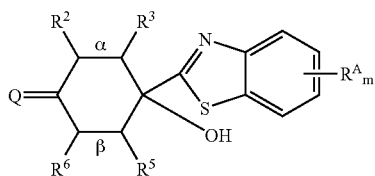

In one embodiment, $R^O$ is —H; α is a double bond; β is a double bond; $R^2$, $R^3$, $R^5$, $R^6$, Q, m, and $R^A$ are as defined herein, and the compounds have the following formula:

(37)

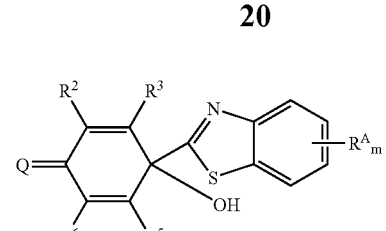

In one embodiment, $R^O$ is —H; α is a double bond; β is a double bond; the ring substituents, $R^3$ and $R^5$ are both —H; the ring substituents, $R^2$ and $R^6$, are both —H; and Q, m, and $R^A$ are as defined herein, and the compounds have the following formula:

(38)

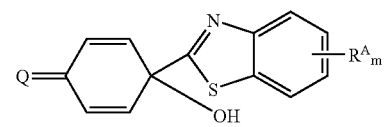

In one embodiment, $R^O$ is —H; α is a double bond; β is a double bond; the ring substituents, $R^3$ and $R^5$ are both —H; the ring substituents, $R^2$ and $R^6$, are both —H; Q is =O; and m and $R^A$ are as defined herein, and the compounds have the following formula:

(39)

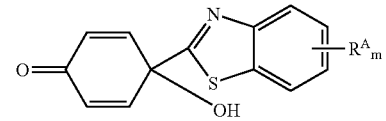

Ring Substituents, $R^2$, $R^3$, $R^4$ and $R^5$

The ring substituents, $R^3$, $R^4$, $R^5$, and $R^6$, may be selected to improve the physical or biological properties of the compound, for example, to improve water solubility and/or bioavailability.

In one embodiment, each of the ring substituents, $R^3$, $R^4$, $R^5$, and $R^6$, is:

(a) H;
or:
(b) a ring substituent which, together with an adjacent ring substituent, and together with the ring atoms to which these ring substituents are attached, form a fused ring (fused to the main ring), as described below under the heading "Ring Substituents: Fused Rings;"
or:
(c) a divalent monodentate substituent, as described below under the heading "Ring Substituents: Monovalent Monodentate Substituents;"
    and if one or both of $R^2$ and $R^3$ is a divalent monodentate group, then α is a single bond;
    and if one or both of $R^5$ and $R^6$ is a divalent monodentate group, then β is a single bond.
or:
(d) a monovalent monodentate substituent, as described below under the heading "Ring Substituents: Monovalent Monodentate Substituents."

In one embodiment, each of the ring substituents, $R^3$, $R^4$, $R^5$, and $R^6$, is:

(a) H;
or:
(b) a monovalent monodentate substituent, as described below under the heading "Ring Substituents: Monovalent Monodentate Substituents."

Ring Substituents: Fused Rings

In one embodiment, one or more ring substituents (e.g., $R^3$, $R^4$, $R^5$, or $R^6$), together with an adjacent ring substituent (i.e., selected from the remainder of $R^3$, $R^4$, $R^5$, and $R^6$), and together with the ring atoms to which these ring substituents are attached, form a fused ring (fused to the main ring).

In one embodiment, one or more ring substituent (e.g., $R^3$, $R^4$, $R^5$, or $R^6$), together with an adjacent ring substituent, and together with the ring atoms to which these ring substituents are attached, form a fused aromatic ring (fused to the main ring).

In one embodiment, one or more ring substituent (e.g., $R^3$, $R^4$, $R^5$, or $R^6$), together with an adjacent ring substituent, and together with the ring atoms to which these ring substituents are attached, form a fused aromatic ring (fused to the main ring) with 5 or 6 ring atoms.

In one embodiment, one or more ring substituent (e.g., $R^3$, $R^4$, $R^5$, or $R^6$), together with an adjacent ring substituent, and together with the ring atoms to which these ring substituents are attached, form a fused aromatic ring (fused to the main ring) with 6 ring atoms.

In one embodiment, one or more ring substituent (e.g., $R^3$, $R^4$, $R^5$, or $R^6$), together with an adjacent ring substituent, and together with the ring atoms to which these ring substituents are attached, form a fused aromatic ring (fused to the main ring) with 6 ring carbon atoms.

In one embodiment, $R^2$, together with $R^3$, together with the ring atoms to which they are attached, form a fused ring (fused to the main ring), as described above (e.g., a fused aromatic ring; a fused aromatic ring with 5 or 6 ring atoms; a fused aromatic ring with 6 ring atoms; a fused aromatic ring with 6 ring carbon atoms).

In one embodiment, $R^5$, together with $R^6$, together with the ring atoms to which they are attached, form a fused ring (fused to the main ring), as described above (e.g., a fused aromatic ring; a fused aromatic ring with 5 or 6 ring atoms; a fused aromatic ring with 6 ring atoms; a fused aromatic ring with 6 ring carbon atoms).

In one embodiment, the compounds have the following formula, wherein $\beta$, Q, Ar, $R^O$, $R^5$, and $R^6$ are as defined herein:

(40)

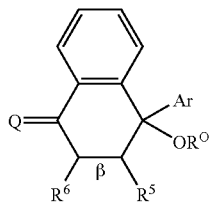

In one embodiment, the bond marked $\beta$ is a double bond; Q, Ar, $R^O$, $R^5$, and $R^6$ are as defined herein; and the compounds have the following formula:

(41)

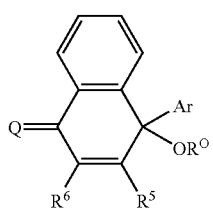

In one embodiment, the bond marked $\beta$ is a double bond; Q is =O; and Ar, $R^O$, $R^5$, and $R^6$ are as defined herein; and the compounds have the following formula:

(42)

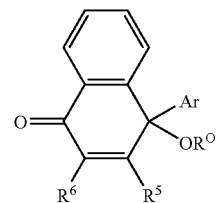

In one embodiment, the bond marked $\beta$ is a double bond; Q is =O; $R^6$ is —H; and Ar, $R^O$, and $R^5$ are as defined herein; and the compounds have the following formula:

(43)

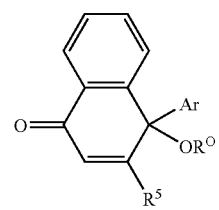

In one embodiment, the bond marked $\beta$ is a double bond; Q is =O; $R^5$ is —H; $R^6$ is —H; and Ar and $R^O$ are as defined herein; and the compounds have the following formula:

(44)

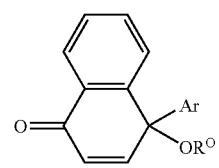

Where the ring substituents, $R^2$ and $R^3$, together with the ring atoms to which they are attached, form an aromatic ring (fused to the main ring), that ring may itself be substituted with one or more aryl substituents, as described herein under the heading "Optional Substituents for Aryl Groups."

In one embodiment, the compound is as defined above, and additionally $R^O$ is —H.

Ring Substituents: Divalent Monodentate Substituents

In one embodiment, one or more of the ring substituents, $R^2$, $R^3$, $R^5$, and $R^6$, is a divalent monodentate group;
  and if one or both of $R^2$ and $R^3$ is a divalent monodentate group, then $\alpha$ is a single bond;
  and if one or both of $R^5$ and $R^6$ is a divalent monodentate group, then $\beta$ is a single bond.

In one embodiment, $\alpha$ is a single bond; $\beta$ is a single bond; and each of $R^3$ and $R^5$ is a divalent monodentate group.

In one embodiment, $\alpha$ is a single bond; $\beta$ is a single bond; each of $R^3$ and $R^5$ is a divalent monodentate group; and each of $R^2$ and $R^6$ is —H.

In one embodiment, $\alpha$ is a single bond; $\beta$ is a single bond; and each of $R^2$ and $R^6$ is a divalent monodentate group.

In one embodiment, $\alpha$ is a single bond; $\beta$ is a single bond; each of $R^2$ and $R^6$ is a divalent monodentate group; and each of $R^3$ and $R^5$ is —H.

In one embodiment, the divalent monondentate group is selected from optionally substituted $C_{1-7}$alkylidene and $C_{5-20}$aryl-$C_{1-7}$alkylidene. In one embodiment, the $C_{5-20}$aryl group of the $C_{5-20}$aryl-$C_{1-7}$alkylidene group is optionally substituted, for example, with one or more aryl substituents, as described herein under the heading "Optional Substituents for Aryl Groups."

In one embodiment, the divalent monondentate group is selected from ethylidine (=CHCH$_3$), vinylidene (=C=CH$_2$), isopropylidene (=C(CH$_3$)$_2$), and benzylidene (=CHPh).

In one embodiment, α is a single bond; β is a single bond; each of R$^2$ and R$^6$ is benzylidene group; each of R$^3$ and R$^5$ is —H; and Q, Ar and R$^O$ are as defined herein; and the compounds have the following formula:

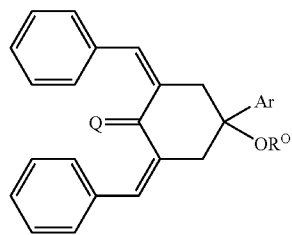

(45)

Ring Substituents: Monovalent Monodentate Substituents

In one embodiment, one or more of the ring substituents, R$^2$, R$^3$, R$^5$, and R$^6$, is a monovalent monodentate group selected from:
halo; hydroxy; ether (e.g., C$_{1-7}$alkoxy); formyl; acyl (e.g., C$_{1-7}$alkylacyl, C$_{5-20}$arylacyl); carboxy; ester; acyloxy; amido; acylamido; thioamido; tetrazolyl; amino; nitro; azido; cyano; cyanato; thiocyano; isothiocyano; sulfhydryl; thioether (e.g., C$_{1-7}$alkylthio); sulfonic acid; sulfonate; sulfone; sulfonyloxy; sulfinyloxy; sulfamino; sulfonamino; sulfinamino; sulfamyl; sulfonamido; C$_{1-7}$alkyl (including, e.g., unsubstituted C$_{1-7}$alkyl, C$_{1-7}$haloalkyl, C$_{1-7}$hydroxyalkyl, C$_{1-7}$carboxyalkyl, C$_{1-7}$aminoalkyl, C$_{5-20}$aryl-C$_{1-7}$alkyl); C$_{3-20}$heterocyclyl; and C$_{5-20}$aryl (including, e.g., C$_{5-20}$carboaryl, C$_{5-20}$heteroaryl, C$_{1-7}$alkyl-C$_{5-20}$aryl and C$_{5-20}$haloaryl)).

In one embodiment, one or more of the ring substituents, R$^2$, R$^3$, R$^5$, and R$^6$, is a monovalent monodentate group selected from:
halo; C$_{1-7}$alkyl; acyl; and, thioether.

In one embodiment, one or more of the ring substituents, R$^2$, R$^3$, R$^5$, and R$^6$, is a monovalent monodentate group selected from:
—F, —Cl, —Br, —I;
-Me, -Et, -nPr, -iPr, —CH$_2$C≡CH;
—C(=O)Me, —C(=O)Et, —C(=O)nPr, —C(=O)iPr, —C(=O)tBu;
—C(=O)Ph; and,
—SR$^S$.

In one embodiment, one or more of the ring substituents, R$^2$, R$^3$, R$^5$, and R$^6$, is a monovalent monodentate group selected from:
—F, —C, —Br, —I, and —SR$^S$.

Ring Substituents: Thioethers

In one embodiment, one or more of the ring substituents, R$^2$, R$^3$, R$^5$, and R$^6$, is a thioether group, —SR$^S$.

In one embodiment, each of the ring substituents, R$^3$ and R$^5$, is —H or a thioether group, —SR$^S$.

In one embodiment, each of the ring substituents, R$^3$ and R$^5$, is —H or a thioether group, —SR$^S$; and the ring substituents, R$^2$ and R$^6$, are —H.

In one embodiment, each of the ring substituents, R$^3$ and R$^5$, is a thioether group, —SR$^S$.

In one embodiment, each of the ring substituents, R$^3$ and R$^5$, is a thioether group, —SR$^S$; and the ring substituents, R$^2$ and R$^6$, are —H.

In one embodiment, one or both of R$^3$ and R$^5$ is a thioether group, —SR$^S$.

In one embodiment, one or both of R$^3$ and R$^5$ is a thioether group, —SR$^S$; and the ring substituents, R$^2$ and R$^6$, are —H.

R$^S$ is an organic group (typically from 1 to 30 atoms other than hydrogen) which optionally bears one or more substituents, such as hydroxy, carboxy, carboxylate, acyloxy, amino, amido, and acyl amido groups.

In one embodiment, R$^S$ is optionally substituted C$_{1-7}$alkyl, C$_{3-20}$heterocyclyl, or C$_{5-20}$aryl.

In one embodiment, R$^S$ is C$_{1-7}$alkyl, for example, -Me, -Et, -nPr, -iPr, -nBu, -iBu, -sBu, or -tBu.

In one embodiment, R$^S$ is C$_{5-20}$aryl-C$_{1-7}$alkyl, for example, —CH$_2$-Ph.

In one embodiment, R$^S$ is C$_{5-20}$aryl, for example, -Ph.

In one embodiment, R$^S$ is a thioether group derived from a sulfhydryl containing compound, such as, for example, an amino acid, e.g., cysteine, glutathione, etc., and analogs thereof (e.g., homocysteine). Examples of such groups include, but are not limited to, the following (where n is e.g., 1, 2, or 3):

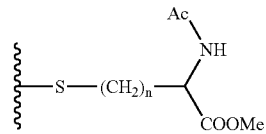

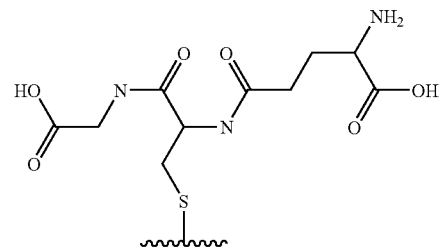

Absence of Ring Substituents

In one embodiment, each of the ring substituents, R$^3$ and R$^5$, is —H; each of the ring substituents, R$^2$ and R$^6$, is —H; and Q, Ar, R$^O$, α, and β are as defined herein, and the compounds have the following formula:

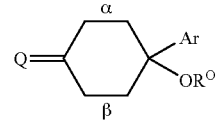

(46)

In one embodiment, each of the ring substituents, R$^3$ and R$^5$, is —H; each of the ring substituents, R$^2$ and R$^6$, is —H;

and Q, Ar, and $R^O$ are as defined herein, and the compounds have the following formula:

(47)

In one embodiment, each of the ring substituents, $R^3$ and $R^5$, is —H; each of the ring substituents, $R^2$ and $R^6$, is —H; and Q, Ar, and $R^O$ are as defined herein, and the compounds have the following formula:

(48)

In one embodiment, each of the ring substituents, $R^3$ and $R^5$, is —H; each of the ring substituents, $R^2$ and $R^6$, is —H; and Q, Ar, and $R^O$ are as defined herein, and the compounds have the following formula:

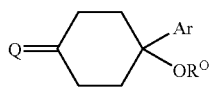

(49)

In one embodiment, each of the ring substituents, $R^3$ and $R^5$, is —H; each of the ring substituents, $R^2$ and $R^6$, is —H; Q is =O; and Ar and $R^O$ are as defined herein, and the compounds have the following formula:

(50)

In one embodiment, each of the ring substituents, $R^3$ and $R^5$, is —H; each of the ring substituents, $R^2$ and $R^6$, is —H; Q is =O; and Ar and $R^O$ are as defined herein, and the compounds have the following formula:

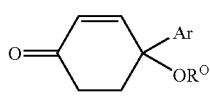

(51)

In one embodiment, each of the ring substituents, $R^3$ and $R^5$, is —H; each of the ring substituents, $R^2$ and $R^6$, is —H; Q is =O; and Ar and $R^O$ are as defined herein, and the compounds have the following formula:

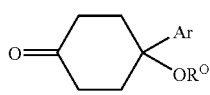

(52)

In one embodiment, the compound is as defined above, and additionally $R^O$ is —H.

Ring Substituents, $R^2$ and $R^6$

In one embodiment, each of the ring substituents, $R^2$ and $R^6$, is —H; and $R^3$, $R^5$, Q, Ar, $R^O$, α, and β are as defined herein, and the compounds have the following formula:

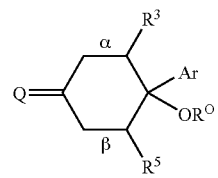

(53)

In one embodiment, one of the ring substituents, $R^2$ and $R^6$, is —H, and the other is other than —H.

In one embodiment, each of the ring substituents, $R^2$ and $R^6$, is other than —H.

In one embodiment, each of the ring substituents, $R^2$ and $R^6$, is other than —H; and each of the ring substituents, $R^3$ and $R^5$, is —H.

In one embodiment, each of the ring substituents, $R^3$ and $R^5$, is —H; each of the ring substituents, $R^2$ and $R^6$, are as defined herein (e.g., —H; a monovalent monodentate substituent; a divalent monodentate substituent); and α, β, Q, Ar, and $R^O$ are as defined herein, and the compounds have the following formula:

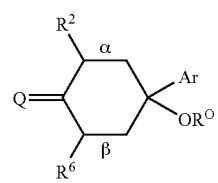

(54)

In one embodiment, each of the ring substituents, $R^2$ and $R^6$, is other than —H (e.g., a monovalent monodentate substituent; a divalent monodentate substituent); each of the ring substituents, $R^3$ and $R^5$, is —H; and α, β, Q, Ar, and $R^O$ are as defined herein, and the compounds have the following formula:

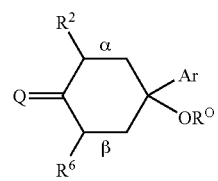

(55)

In one embodiment, each of the ring substituents, $R^2$ and $R^6$, is other than —H (e.g., a monovalent monodentate substituent; a divalent monodentate substituent); each of the ring substituents, $R^3$ and $R^5$, is —H; Q is =O; and α, β, Ar, and $R^O$ are as defined herein, and the compounds have the following formula:

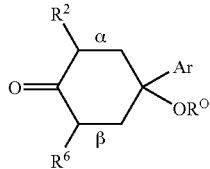
(56)

In one embodiment, α is a single bond; β is a single bond; each of the ring substituents, $R^3$ and $R^5$, is —H; each of the ring substituents, $R^2$ and $R^6$, are as defined herein (e.g., —H; a monovalent monodentate substituet; a divalent monodentate substituent); and Q, Ar, and $R^O$ are as defined herein, and the compounds have the following formula:

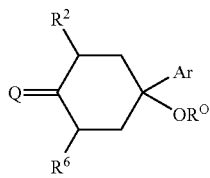
(57)

In one embodiment, α is a single bond; β is a single bond; each of the ring substituents, $R^2$ and $R^6$, is other than —H (e.g., a monovalent monodentate substituent; a divalent monodentate substituent); each of the ring substituents, $R^3$ and $R^5$, is —H; and Q, Ar, and $R^O$ are as defined herein, and the compounds have the following formula:

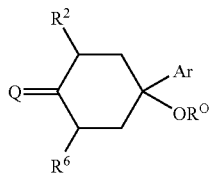
(58)

In one embodiment, α is a single bond; β is a single bond; each of the ring substituents, $R^2$ and $R^6$, is other than —H (e.g., a monovalent monodentate substituent; a divalent monodentate substituent); each of the ring substituents, $R^3$ and $R^5$, is —H; Q is =O; and Ar and $R^O$ are as defined herein, and the compounds have the following formula:

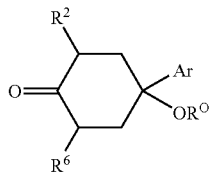
(59)

In one embodiment, α is a double bond; β is a double bond; each of the ring substituents, $R^3$ and $R^5$, is —H; each of the ring substituents, $R^2$ and $R^6$, are as defined herein (e.g., —H; a monovalent monodentate substituet); and Q, Ar, and $R^O$ are as defined herein, and the compounds have the following formula:

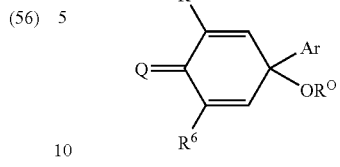
(60)

In one embodiment, α is a double bond; β is a double bond; each of the ring substituents, $R^2$ and $R^6$, is other than —H (e.g., a monovalent monodentate substituent); each of the ring substituents, $R^3$ and $R^5$, is —H; and Q, Ar, and $R^O$ are as defined herein, and the compounds have the following formula:

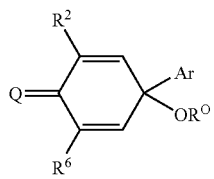
(61)

In one embodiment, α is a double bond; β is a double bond; each of the ring substituents, $R^2$ and $R^6$, is other than —H (e.g., a monovalent monodentate substituent); each of the ring substituents, $R^3$ and $R^5$, is —H; Q is =O; and Ar and $R^O$ are as defined herein, and the compounds have the following formula:

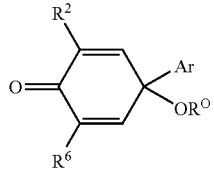
(62)

In one embodiment, the compound is as defined above, and additionally $R^O$ is —H.

Ring Substituents, $R^3$ and $R^5$

In one embodiment, each of the ring substituents, $R^3$ and $R^5$, is —H; each of the ring substituents, $R^2$ and $R^6$, is as defined herein (e.g., —H; a monovalent monodentate substituent; a divalent monodentate substituent); and Q, Ar, $R^O$, α, and β are as defined herein, and the compounds have the following formula:

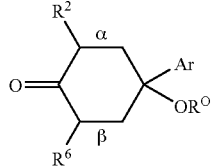
(63)

In one embodiment, one of the ring substituents, $R^3$ and $R^5$, is —H, and the other is other than —H.

In one embodiment, one of the ring substituents, $R^3$ and $R^5$, is —H, and the other is other than —H; and each of the ring substituents, $R^2$ and $R^6$, is —H.

In one embodiment, either (a) α is a double bond; β is a single bond; $R^3$ is —H; and $R^5$ is as defined herein (e.g., —H; a monovalent monodentate substituent; a divalent monodentate substituent); or (b) α is a single bond; β is a double bond; $R^3$ is as defined herein (e.g., —H; a monovalent monodentate substituent; a divalent monodentate substituent); $R^5$ is —H; and each of the ring substituents, $R^2$ and $R^6$, is —H; Q, Ar, and $R^O$ are as defined herein, and the compounds have one of the following formulae:

(64)

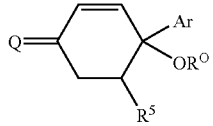

(65)

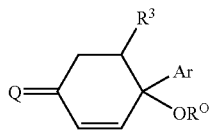

In one embodiment, either (a) α is a double bond; β is a single bond; $R^3$ is —H; and $R^5$ is other than —H (e.g., a monovalent monodentate substituent; a divalent monodentate substituent); or (b) α is a single bond; β is a double bond; $R^3$ is other than —H (e.g., a monovalent monodentate substituent; a divalent monodentate substituent); $R^5$ is —H; and, each of the ring substituents, $R^2$ and $R^6$, is —H; Q, Ar, and $R^O$ are as defined herein, and the compounds have one of the following formulae:

(66)

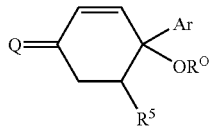

(67)

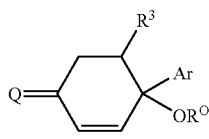

In one embodiment, either (a) α is a double bond; α is a single bond; $R^3$ is —H; $R^5$ is other than —H (e.g., a monovalent monodentate substituent; a divalent monodentate substituent); or (b) α is a single bond; β is a double bond; $R^3$ is other than —H (e.g., a monovalent monodentate substituent; a divalent monodentate substituent); $R^5$ is —H; and, each of the ring substituents, $R^2$ and $R^6$, is —H; Q is =O; Ar, and $R^O$ are as defined herein, and the compounds have one of the following formulae:

(68)

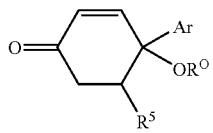

(69)

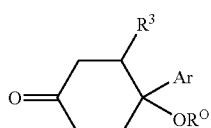

In one embodiment, neither of the ring substituents, $R^3$ and $R^5$, is —H.

In one embodiment, neither of the ring substituents, $R^3$ and $R^5$, is —H; and each of the ring substituents, $R^2$ and $R^6$, is —H.

In one embodiment, α is a single bond; β is a single bond; each of the ring substituents, $R^2$ and $R^6$, is —H; each of the ring substituents, $R^3$ and $R^5$, is as defined herein (e.g., —H; a monovalent monodentate substituent; a divalent monodentate substituent); and Q, Ar, and $R^O$ are as defined herein, and the compounds have the following formula:

(70)

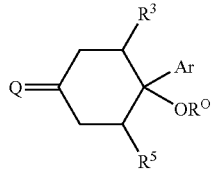

In one embodiment, α is a single bond; β is a single bond; each of the ring substituents, $R^3$ and $R^5$, is other than —H (e.g., a monovalent monodentate substituent; a divalent monodentate substituent); each of the ring substituents, $R^2$ and $R^6$, is —H; and Q, Ar, and $R^O$ are as defined herein, and the compounds have the following formula:

(71)

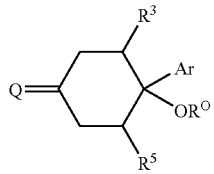

In one embodiment, α is a single bond; β is a single bond; each of the ring substituents, $R^3$ and $R^5$, is other than —H (e.g., a monovalent monodentate substituent; a divalent monodentate substituent); each of the ring substituents, $R^2$ and $R^6$, is —H; Q is =O; and Ar and $R^O$ are as defined herein, and the compounds have the following formula:

(72)

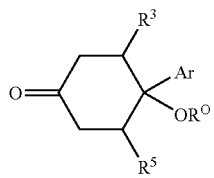

In one embodiment, α is a double bond; β is a double bond; each of the ring substituents, $R^2$ and $R^6$, is —H; each of the ring substituents, $R^3$ and $R^5$ is as defined herein (e.g., —H; a monovalent monodentate substituent); and Q, Ar, and $R^O$ are as defined herein, and the compounds have the following formula:

(73)

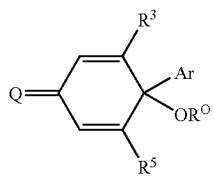

In one embodiment, α is a double bond; β is a double bond; each of the ring substituents, $R^3$ and $R^5$, is other than —H (e.g., a monovalent monodentate substituent); each of the ring substituents, $R^2$ and $R^6$, is —H; and Q, Ar, and $R^O$ are as defined herein, and the compounds have the following formula:

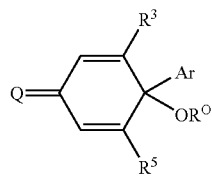

(74)

In one embodiment, α is a double bond; β is a double bond; each of the ring substituents, $R^3$ and $R^5$, is other than —H (e.g., a monovalent monodentate substituent); each of the ring substituents, $R^2$ and $R^6$, is —H; Q is =O; and Ar and $R^O$ are as defined herein, and the compounds have the following formula:

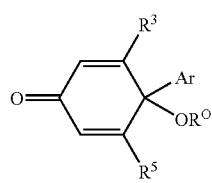

(75)

In one embodiment, each of ring substituents, $R^3$ and $R^5$, is —H or as defined under the heading "Ring Substituents: Monovalent Monodentate Substituents."

In one embodiment, each of ring substituents, $R^3$ and $R^5$, is as defined under the heading "Ring Substituents: Monovalent Monodentate Substituents."

In one embodiment, the compound is as defined above, and additionally $R^O$ is —H.

EXAMPLES OF SPECIFIC EMBODIMENTS

Some individual embodiments of the present invention include the following compounds:

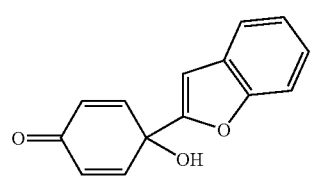

Q01

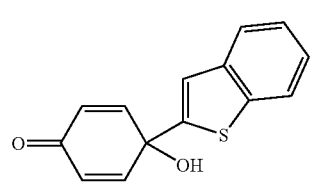

Q02

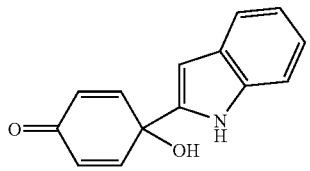

Q03

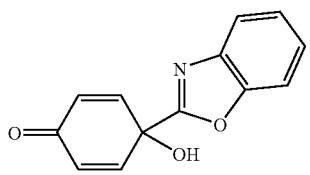

Q04

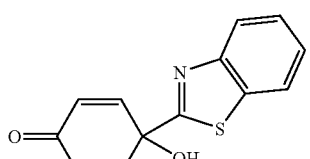

Q05

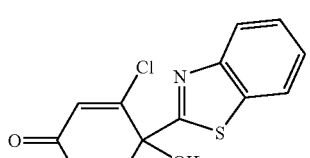

Q06

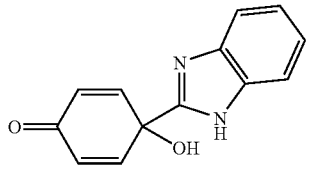

Q07

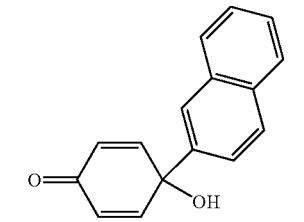

Q08

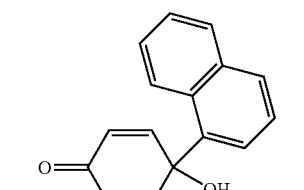

Q09

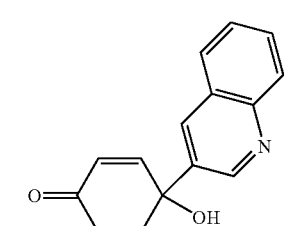

Q10

-continued
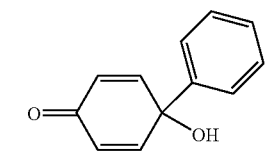 Q11
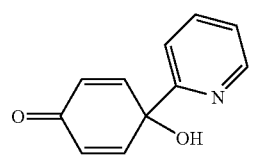 Q12
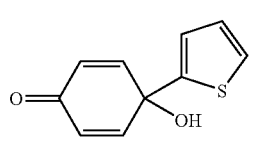 Q13
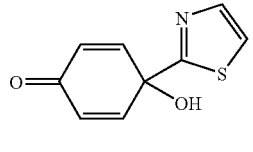 Q14
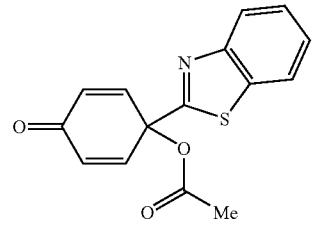 Q15
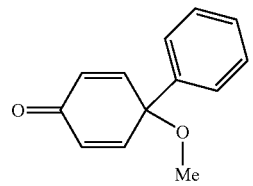 Q16
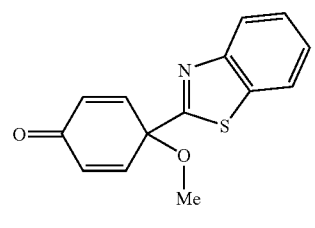 Q17
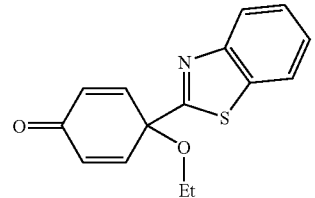 Q18
-continued
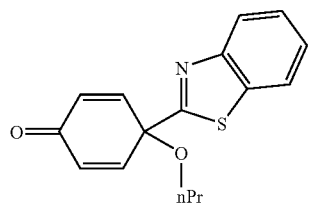 Q19
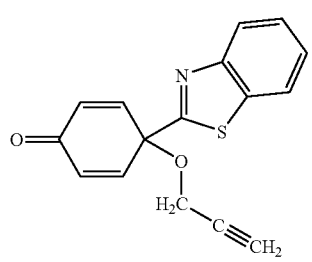 Q20
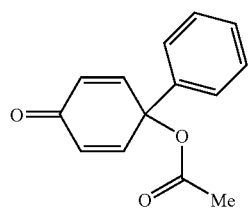 Q21
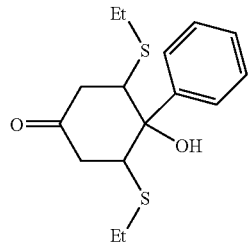 Q22
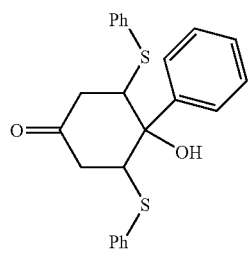 Q23
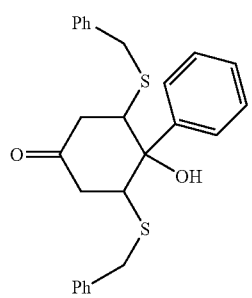 Q24

-continued
Q25 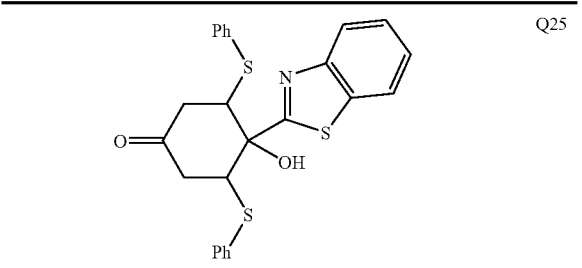
Q26 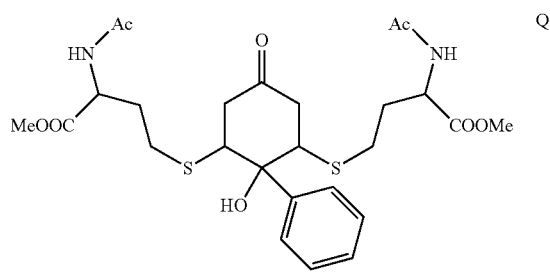
Q27 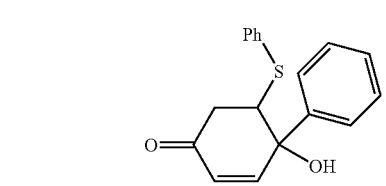
Q28 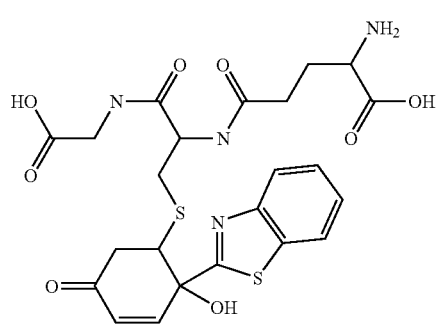
Q29 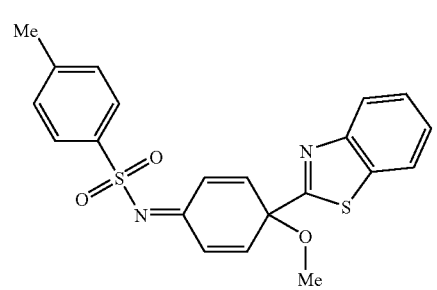
Q30 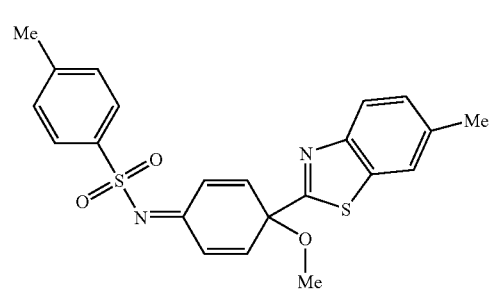
-continued
Q31 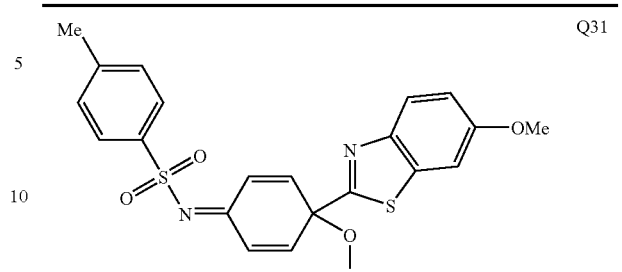
Q32 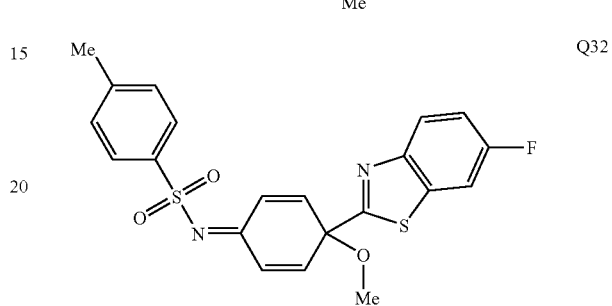
Q33 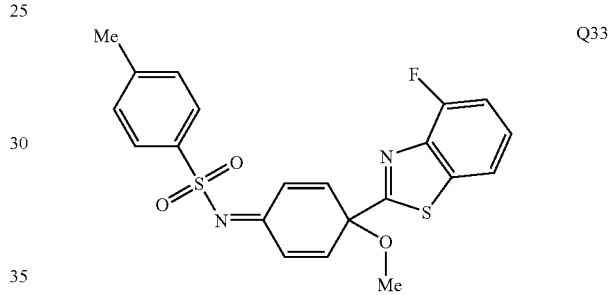
Q34 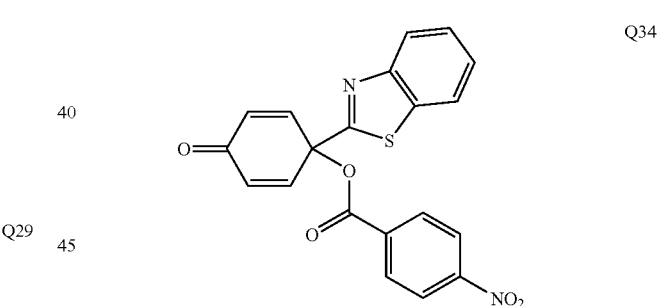
Q35 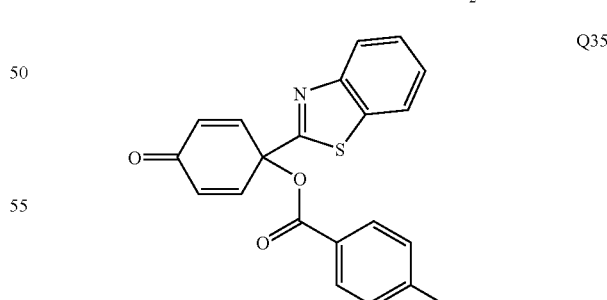
Q36 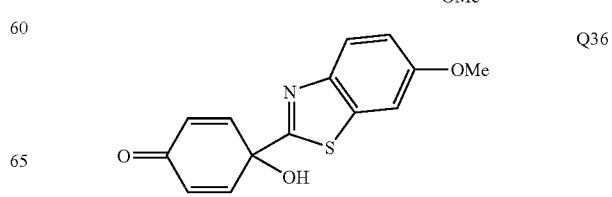

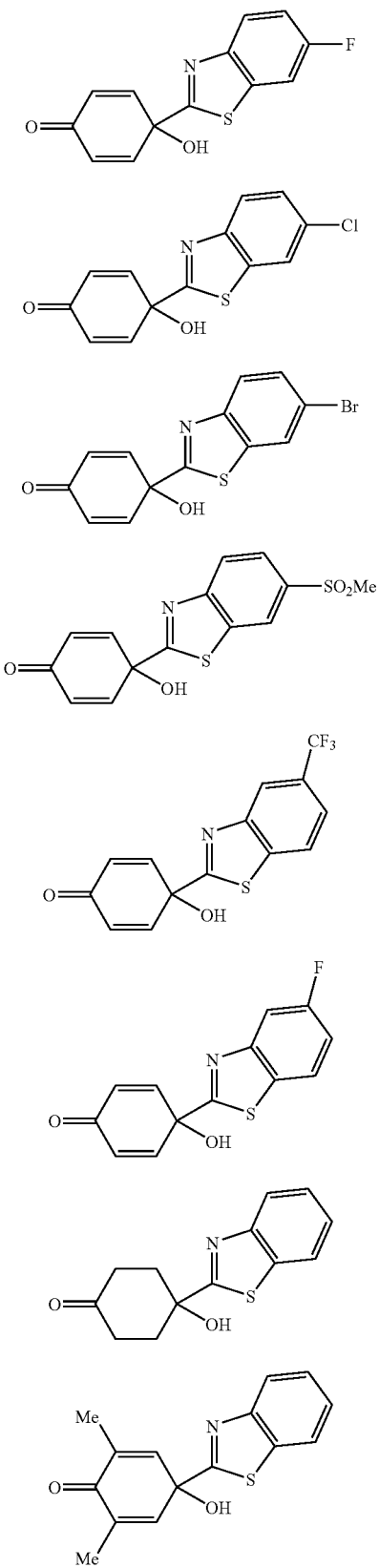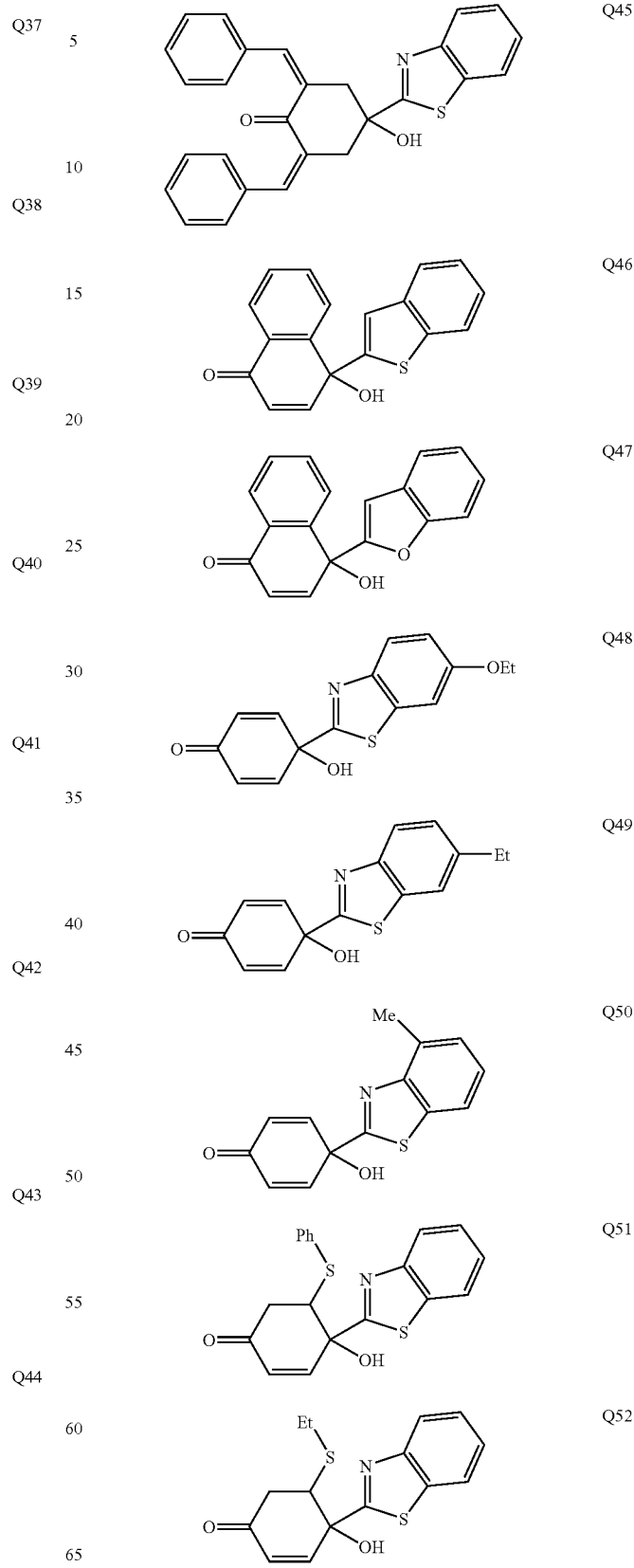

-continued

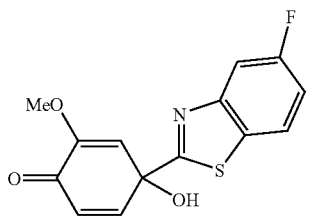

Q53

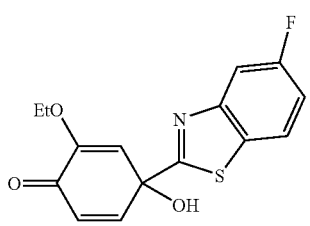

Q54

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and $C_{1-7}$alkyl.

The term "multivalent monodentate substituents," as used herein, pertains to substituents which have one point of covalent attachment, but through a double bond or triple bond. Examples of such substituents include oxo, imino, alkylidene, and alklidyne.

The term "bidentate substituents," as used herein, pertains to substituents which have two points of covalent attachment, and which act as a linking group between two other moieties. Examples of such substituents include $C_{1-7}$alkylene and $C_{5-20}$arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Examples of groups of alkyl groups include $C_{1-4}$alkyl (lower alkyl), $C_{1-7}$alkyl, $C_{1-20}$alkyl.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), n-undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Examples of (unsubstituted) saturated alicyclic (and carbocyclic) alkyl groups, which are also referred to herein as "cycloalkyl" groups, include, but are not limited to, cyclopropyl ($C_3$), cyclobutyl ($C_4$), cyclopentyl ($C_5$), cyclohexyl ($C_6$), cycloheptl ($C_7$), norbornyl ($C_7$), and adamantyl ($C_{10}$).

Examples of saturated alicyclic (and carbocyclic) alkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl.

Examples of saturated alicyclic (and carbocyclic) alkyl groups, which are also referred to herein as "cycloalkyl-alkyl" groups, include, but are not limited to, cyclopropylmethyl, cyclobutylmethyl, cyclopentylmethyl, and cyclohexylmethyl.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (—C(CH$_3$)=CH$_2$), butenyl ($C_4$), pentenyl ($C_5$), and hexenyl ($C_6$).

Examples of (unsubstituted) unsaturated alicyclic (and carbocyclic) alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Examples of unsaturated alicyclic (and carbocyclic) alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of unsaturated alicyclic (carbocyclic) alkenyl groups, which are also referred to herein as "cycloalkenyl-alkyl" groups, include, but are not limited to, cyclopropenylmethyl and cyclohexenylmethyl.

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —CH$_2$—C≡CH).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidene groups include $C_{1-4}$alkylidene, $C_{1-7}$alkylidene, $C_{1-20}$alkylidene.

Examples of alkylidene groups include, but are not limited to, methylidene (=CH$_2$), ethylidene (=CH—CH$_3$), vinylidene (=C=CH$_2$), and isopropylidene (=C(CH$_3$)$_2$).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include $C_{1-4}$alkylidyne, $C_{1-7}$alkylidyne, $C_{1-20}$alkylidyne.

Examples of alkylidyne groups include, but are not limited to, methylidyne (≡CH) and ethylidyne (≡C—CH$_3$).

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-7}$aryl, $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, as in "heteroaryl groups" (e.g., $C_{5-20}$heteroaryl).

Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:
  $C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
  $C_{10}$heterocyclic groups (with 2 fused rings) derived from benzodioxan ($O_2$), quinoline ($N_1$), isoquinoline ($N_1$), benzoxazine ($N_1O_1$), benzodiazine ($N_2$), pyridopyridine ($N_2$), quinoxaline ($N_2$), quinazoline ($N_2$);
  $C_{13}$heterocyclic groups (with 3 fused rings) derived from carbazole ($N_1$), dibenzofuran ($O_1$), dibenzothiophene ($S_1$); and,
  $C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N═ group may be substituted in the form of an N-oxide, that is, as —N(→O)═ (also denoted —N⁺(→O⁻)═). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (═O) groups on ring carbon atoms. Monocyclic examples of such groups include, but are not limited to, those derived from:
$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (═O) groups on ring carbon atoms include, but are not limited to, those derived from:
  cyclic anhydrides (—C(═O)—O—C(═O)— in a ring), including but not limited to maleic anhydride ($C_5$), succinic anhydride ($C_5$), and glutaric anhydride ($C_6$);
  cyclic carbonates (—O—C(═O)—O— in a ring), such as ethylene carbonate ($C_5$) and 1,2-propylene carbonate ($C_5$);
  imides (—C(═O)—NR—C(═O)— in a ring), including but not limited to, succinimide ($C_5$), maleimide ($C_5$), phthalimide, and glutarimide ($C_6$);
  lactones (cyclic esters, —O—C(═O)— in a ring), including, but not limited to, β-propiolactone, γ-butyrolactone, δ-valerolactone (2-piperidone), and ε-caprolactone;
  lactams (cyclic amides, —NR—C(═O)— in a ring), including, but not limited to, β-propiolactam ($C_4$), γ-butyrolactam (2-pyrrolidone) ($C_5$), δ-valerolactam ($C_6$), and ε-caprolactam ($C_7$);
  cyclic carbamates (—O—C(═O)—NR— in a ring), such as 2-oxazolidone ($C_5$);
  cyclic ureas (—NR—C(═O)—NR— in a ring), such as 2-imidazolidone ($C_5$) and pyrimidine-2,4-dione (e.g., thymine, uracil) ($C_6$).

The above alkyl, alkylidene, alkylidyne, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-buoy), —O(sBu) (sec-buoy), —O(iBu) (isobutoxy), and —O(tBu) (tert-buoy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

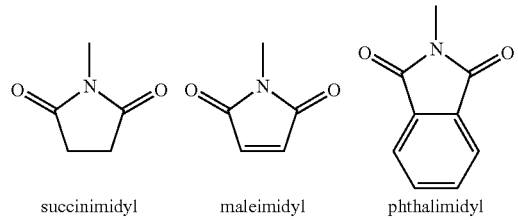

succinimidyl    maleimidyl    phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

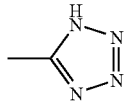

Amino: —NR$^1$R$^2$, wherein R$^1$ and R$^2$ are independently amino substituents, for example, hydrogen, a C$_{1-7}$alkyl group (also referred to as C$_{1-7}$alkylamino or di-C$_{1-7}$alkylamino), a C$_{3-20}$heterocyclyl group, or a C$_{5-20}$aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a C$_{1-7}$alkyl group, a C$_{3-20}$heterocyclyl group, or a C$_{5-20}$aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$alkyl group, a C$_{3-20}$heterocyclyl group, or a C$_{5-20}$aryl group, preferably H or a C$_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.

Azido: —N$_3$.

Cyano (nitrile, carbonitrile): —CN.

Cyanato: —OCN.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$alkyl group (also referred to as a C$_{1-7}$alkylthio group), a C$_{3-20}$heterocyclyl group, or a C$_{5-20}$aryl group, preferably a C$_{1-7}$alkyl group. Examples of C$_{1-7}$alkylthio groups include, but are not limited to, —SCH$_3$ and —SCH$_2$CH$_3$.

Disulfide: —SS—R, wherein R is a disulfide substituent, for example, a C$_{1-7}$alkyl group, a C$_{3-20}$heterocyclyl group, or a C$_{5-20}$aryl group, preferably a C$_{1-7}$alkyl group (also referred to herein as C$_{1-7}$alkyl disulfide). Examples of C$_{1-7}$alkyl disulfide groups include, but are not limited to, —SSCH$_3$ and —SSCH$_2$CH$_3$.

Sulfonic acid (sulfo): —S(=O)$_2$OH, —SO$_3$H.

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ and —S(=O)$_2$OCH$_2$CH$_3$.

Sulfinic acid: —S(=O)OH, —SO$_2$H.

Sulfinate (sulfinic acid ester): —S(=O)OR; wherein R is a sulfinate substituent, for example, a C$_{1-7}$alkyl group, a C$_{3-20}$heterocyclyl group, or a C$_{5-20}$aryl group, preferably a C$_{1-7}$alkyl group. Examples of sulfinate groups include, but are not limited to, —S(=O)OCH$_3$ and —S(=O)OCH$_2$CH$_3$.

Sulfate: —OS(=O)$_2$OR; wherein R is a sulfate substituent, for example, a C$_{1-7}$alkyl group, a C$_{3-20}$heterocyclyl group, or a C$_{5-20}$aryl group, preferably a C$_{1-7}$alkyl group. Examples of sulfate groups include, but are not limited to, —OS(=O)$_2$OCH$_3$ and —SO(=O)$_2$OCH$_2$CH$_3$.

Sulfone (sulfonyl): —S(=O)$_2$R, wherein R is a sulfone substituent, for example, a C$_{1-7}$alkyl group, a C$_{3-20}$heterocyclyl group, or a C$_{5-20}$aryl group, preferably a C$_{1-7}$alkyl group, for example, a fluorinated or perfluorinated C$_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfine (sulfinyl, sulfoxide): —S(=O)R, wherein R is a sulfine substituent, for example, a C$_{1-7}$alkyl group, a C$_{3-20}$heterocyclyl group, or a C$_{5-20}$aryl group, preferably a C$_{1-7}$alkyl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfamino: —NR$^1$S(=Q)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Phosphino (phosphine): —PR$_2$, wherein R is a phosphino substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$alkyl group, a $C_{3-20}$heterocyclyl group, or a $C_{5-20}$aryl group, preferably a $C_{1-7}$alkyl group or a $C_{5-20}$aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2_2$, where R$^1$ and R$^2$ are phosphoramidite substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2_2$, where R$^1$ and R$^2$ are phosphoramidate substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Silyl: —SiR$_3$, where R is a silyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of silyl groups include, but are not limited to, —SiH$_3$, —SiH$_2$(CH$_3$), —SiH(CH$_3$)$_2$, —Si(CH$_3$)$_3$, —Si(Et)$_3$, —Si(iPr)$_3$, —Si(tBu)(CH$_3$)$_2$, and —Si(tBu)$_3$.

Oxysilyl: —Si(OR)$_3$, where R is an oxysilyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of oxysilyl groups include, but are not limited to, —Si(OH)$_3$, —Si(OMe)$_3$, —Si(OEt)$_3$, and —Si(OtBu)$_3$.

Siloxy (silyl ether): —OSiR$_3$, where SiR$_3$ is a silyl group, as discussed above.

Oxysiloxy: —OSi(OR)$_3$, wherein OSi(OR)$_3$ is an oxysilyl group, as discussed above.

In many cases, substituents may themselves be substituted. For example, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkoxy-$C_{5-20}$aryl group, e.g., as in anisole).

These and other specific examples of such substituted-substituents are described below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a "$C_{1-7}$perhaloalkyl group." Examples of $C_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

$C_{1-7}$haloalkoxy: —OR, wherein R is a $C_{1-7}$haloalkyl group. Examples of $C_{1-7}$haloalkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —CH$_2$OH, —CH$_2$CH$_2$OH, and —CH(OH)CH$_2$OH.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

$C_{1-7}$aminoalkylamino: The term "$C_{1-7}$aminoalkylamino," as used herein, pertains to an amino group, —NR$^1$R$^2$, in which one of the substituents, R$^1$ or R$^2$, is itself a $C_{1-7}$aminoalkyl group (—$C_{1-7}$alkyl-NR$^1$R$^2$). The $C_{1-7}$aminoalkylamino may be represented, for example, by the formula —NR$^1$—$C_{1-7}$alkyl-NR$^1$R$^2$. Examples of amino-$C_{1-7}$alkylamino groups include, but are not limited to, groups of the formula —NR$^1$(CH$_2$)$_n$NR$^1$R$^2$, where n is 1 to 6, for example, —NHCH$_2$NH$_2$, —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH (Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), and —NH(CH$_2$)$_6$NH(Et).

C$_{1-7}$alkyl-C$_{5-20}$aryl: The term "C$_{1-7}$alkyl-C$_{5-20}$aryl," as used herein, describes certain C$_{5-20}$aryl groups which have been substituted with a C$_{1-7}$alkyl group. Examples of such groups include, but are not limited to, tolyl (as in toluene), xylyl (as in xylene), mesityl (as in mesitylene), styryl (as in styrene), and cumenyl (as in cumene).

C$_{1-7}$alkyl-C$_{5-20}$aryloxy: The term "C$_{1-7}$alkyl-C$_{5-20}$aryloxy," as used herein, describes certain C$_{5-20}$aryloxy groups which have been substituted with a C$_{1-7}$alkyl group. Examples of such groups include, but are not limited to, tolyloxy, xylyloxy, mesityloxy, and cumenyloxy.

C$_{5-20}$aryl-C$_{1-7}$alkyl: The term "C$_{5-20}$aryl-C$_{1-7}$alkyl," as used herein, describers certain C$_{1-7}$alkyl groups which have been substituted with a C$_{5-20}$aryl group. Examples of such groups include, but are not limited to, benzyl (phenylmethyl), tolylmethyl, phenylethyl, triphenylmethyl (trityl), and cinnamyl (3-phenyl-2-propenyl, C$_6$H$_5$—CH=CH—CH$_2$—).

C$_{5-20}$aryl-C$_{1-7}$alkoxy: The term "C$_{5-20}$aryl-C$_{1-7}$alkoxy," as used herein, describes certain C$_{1-7}$alkoxy groups which have been substituted with a C$_{5-20}$aryl group. Examples of such groups include, but are not limited to, benzyloxy, tolylmethoxy, and phenylethoxy.

C$_{5-20}$haloaryl: The term "C$_{5-20}$haloaryl," as used herein, describes certain C$_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d-and l-forms; (+) and (-) forms; keto-, enol-, and enolate-forms; syn- and anti-forms; synclinal- and anticlinal-forms; α- and β-forms; axial and equatorial forms; boat-, chair-, twist-, enyelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

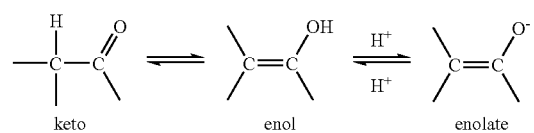

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; F may be in any isotopic form, including $^{18}$F and $^{19}$F; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1–19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, gycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991) and *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O$).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl
(e.g., -Me, -Et, -nPr, -iPr, -nBu, -sBu, -iBu, -tBu);
C:$_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Additional acronyms:
2,2,6,6-tetramethyl-1-piperidinyloxy free radical (TEMPO);
bis(trifluoroacetoxy)-iodobenzene (BTIB);
di(acetoxy)iodobenzene (DAIB);
4-dimethylaminopyridine (DMAP).

Synthesis

Several methods for the chemical synthesis of compounds of the present invention are described herein. These methods may be modified and/or adapted in known ways in order to facilitate the synthesis of additional compounds within the scope of the present invention.

Method A

General Method for the Synthesis of Quinols: 1,2-Addition of a Lithioaromatic Compound to a Quinone Monoacetal An efficient and general one-pot method for the synthesis of aromatic and heteroaromatic quinol derivatives is described in detail below. Treatment of the appropriate aromatic or heteroaromatic compound with n-butyl lithium in THF at −78° C. (conditions which are not necessary if commercially available phenyl lithium is employed) followed by addition to 4,4-dimethoxy-2,5-cyclohexadien-1-one generates the required quinol protected as its dimethyl acetal. Deprotection using dilute acetic acid gives the desired quinols in good overall yield. See, for example, Capparelli et al., 1987.

A solution of the appropriate aromatic/heteroaromatic compound (26.0 mmol) in THF (30 mL) was added to a solution of n-butyllithium (17.8 mL of a 1.6 M solution in hexanes, 28.5 mmol) in THF (30 mL) at −78° C. with stirring. After stirring at −78° C. for one hour, the aryllithium compound solution was transferred via cannula to a solution of 4,4-dimethoxy-2,5-cyclohexadien-1-one (3.6 mL, 26.0 mmol) in THF (60 mL). After stirring for two hours at −78° C., the reaction mixture was poured into brine (100 mL) and the layers separated. The aqueous/THF layer was extracted using dichloromethane (3×100 mL) and the combined organic layers dried (MgSO$_4$), filtered and concentrated in vacuo to yield the protected aromatic quinol. The protected product was dissolved in acetone (40 mL) and 10% aqueous acetic acid (40 mL) was added. The mixture was heated at reflux, and then allowed to cool and the acetone removed in vacuo. The aqueous phase was extracted using dichloromethane (3×50 mL), dried (MgSO$_4$), filtered and concentrated to give the aromatic or heteroaromatic quinol, which was purified by flash column chromatography where necessary.

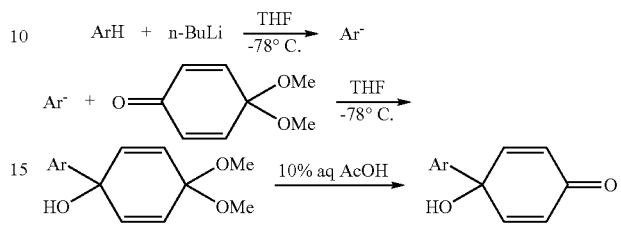

Method B

General Method for the Synthesis of Quinols: 1,2-Addition of a Lithioaromatic Compound to a Cyanohydrin TMS Ether Protected Quinone To benzothiazole (2.497 g, 18.5 mmol) in dry diethylether (20 mL) under nitrogen at −78° C. was added n-butyllithium (7.39 mL of a 2.5 M solution in hexanes, 18.5 mmol) dropwise over 10 minutes. After stirring for 30 minutes the reaction mixture was cooled to −196° C. (liquid N$_2$) and 4-cyano-4-trimethylsilyloxy-2,5-cyclohexadienone (3.83 g, 18.5 mmol) in dry diethylether (10 mL) was added dropwise over 10 minutes. The reaction mixture was slowly warmed to −100° C. and stirred for 2.5 hours after which water (20 mL) was added and the mixture warmed to room temperature. Diethylether (20 mL) was added and the organic fraction washed with water (2×20 mL). The organic layer was dried over magnesium sulphate and the solvent removed under in vacuo. The residue was treated with tetrabutylammonium fluoride trihydrate (11.673 g, 37 mmol) in THF (50 mL) for 2 hours. Water (100 mL) was added and the mixture extracted with ether (2×50 mL). The combined organic layers were washed with water (2×50 mL) and dried over magnesium sulphate. The quinol was purified by flash column chromatography using ethyl acetate:hexane (1:4) as eluant. The yield was 24%.

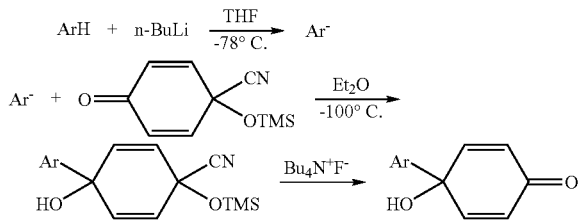

Method C

General Method for the Synthesis of Quinols: Oxidation of 4-(substituted)phenols This method employs bis(trifluoroacetoxy)-iodobenzene (BTIB) and the stable free radical, 2,2,6,6-tetramethyl-1- piperidinyloxy (TEMPO), in order to inhibit unwanted side reactions, and give a cleaner reaction with improved yields.

To 2-(4-hydroxyphenyl)benzothiazole (0.227 g, 1.0 mmol) and TEMPO (0.031 g, 0.2 mmol, 0.2 equivalents) dissolved in acetonitrile:water (9:1, 40 mL) was added BTIB (0.650 g, 1.5 mmol, 1.5 equivalents) in acetonitrile (5 mL) over 1 minute. The volume was reduced to 20 mL under vacuum and diluted with water (50 mL). The product was extracted with diethylether (2×25 mL) and the combined organic layers washed with saturated potassium carbonate solution (2×25 mL) and water (25 mL) then dried over magnesium sulphate and the solvent removed in vacuo. The quinol was purified by flash column chromatography using ethyl acetate:hexane (1:4) as eluant. The yield was 52%.

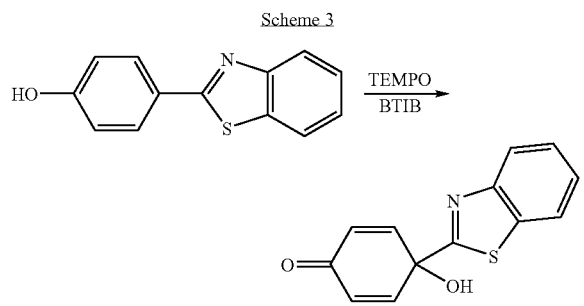

Method D

General Method for the Synthesis of Quinol Acetate Esters

This method uses the hypervalent iodine oxidizing agent, di(acetoxy)iodobenzene (DAIB). See, e.g., Wells et al., 2000; Pelter et al., 1993.

To the 4-(substituted)phenol (0.5 g) in acetic acid (40 ml) was added DAIB (1.1 eq.) in acetic acid (30 ml). The reaction was maintained at 50° C. for 2 hours. After cooling and filtering the solvent was removed in vacuo and the quinol acetate purified by flash column chromatography (eluted with ethyl acetate/hexane 1:4).

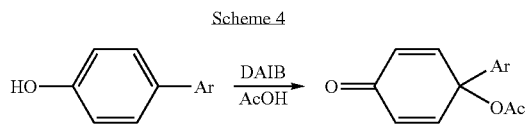

Method E

General Method for the Synthesis of Quinol Ethers

To the 4-(substituted)phenol (0.5 g) in alcohol (15 ml) was added di(acetoxy)iodobenzene (DAIB) (1.1 equivalents) in alcohol (5 ml) with stirring. After 5 minutes, the solvent was removed in vacuo and the quinol ether purified by flash column chromatography (eluted with ethyl acetate/hexane 1:4). See, for example, Callinan et al., 1990.

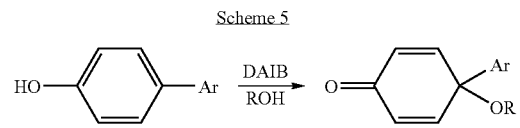

Method F

General Method for the Synthesis of Quinol Esters from Quinols

To the quinol, e.g., 4-hydroxy-4-phenyl-2,5-cyclohexadienone (0.335 g, 1.8 mmol), acetic anhydride (0.276 g, 2.7 mmol, 1.5 eq.) and triethylamine (0.273 g, 2.7 mmol, 1.5 eq.) dissolved in dichloromethane (20 mL) was added DMAP (0.044 g, 0.36 eq.). The reaction mixture was stirred for 24 hours at room temperature, washed with 1 M HCl (20 mL), then saturated sodium hydrogen carbonate solution (2×20 mL) and the organic layer dried over magnesium sulphate. Removal of the solvent in vacuo gave an oil which was dissolved in ether, filtered, and the solvent removed in vacuo to give the desired quinol ester. See, e.g., Wessley et al., 1952.

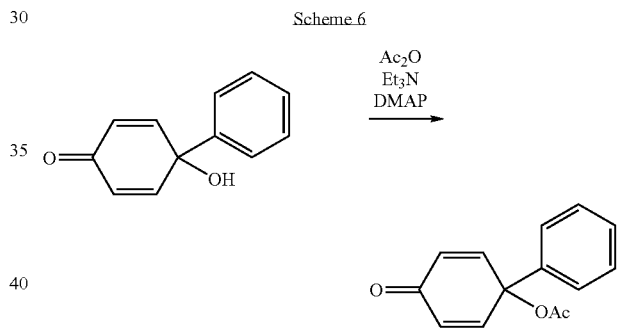

In an analogous method, an acyl chloride, RC(=O)Cl, (e.g., para-nitrophenylacyl chloride, para-methoxyphenylacyl chloride, etc.) is used instead of acetic anhydride.

Method G

General method for the Synthesis of Quinol Methyl Ethers from Quinols

To 4-benzothiazol-2-yl-4-hydroxy-cyclohexadienone (0.1 g, 0.41 mmol) in dry THF (5 mL) at −78° C. under $N_2$ was added potassium t-butoxide (0.069 g, 0.615 mmol, 1.5 equivalents) suspended in THF (2 mL) with stirring. After 20 minutes, methyl iodide (0.088 g, 0.615 mmol, 1.5 equivalents) was added and the reaction mixture warmed to 0° C. for 4 hours. Water (20 mL) was added and the reaction warmed to room temperature and extracted with diethylether (2×20 mL). The combined organic layers were combined, washed with water (2×10 mL) and dried over magnesium sulphate. Removal of the solvent in vacuo gave a solid which was stirred with hexane then collected on a filter, washed with hexane and dried under vacuum. The yield of quinol methyl ether was 49%.

Scheme 7

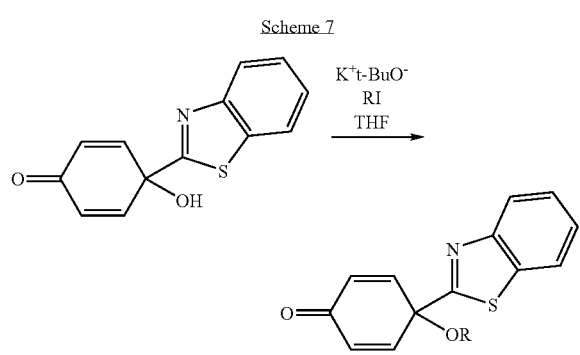

Method H

General Method for the Synthesis of bis-Thiol Adducts

To a solution of the quinol (0.1 g) in ethanol (5 mL) was added the thiol (2.0 equivalents) followed by triethylamine (0.1 equivalents). After two hours the solvent was removed under vacuum and the residue stirred with diethylether: hexane (1:1, 5 mL). The precipitate was collected on a filter and dried under vacuum.

Scheme 8

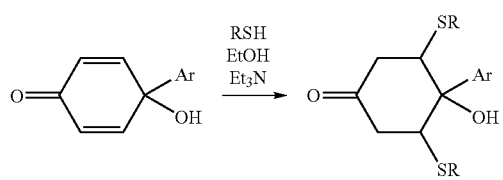

Method I

General Method for the Synthesis of mono-Thiol Adducts

To a solution of the quinol (0.1 g) in ethanol (5 mL) was added the thiol (2.0 equivalents). After two hours the solvent was removed under vacuum and the residue dissolved in diethylether (1 mL) and purified by column chromatography (silica gel, EtOAc:hexane 2:8).

Scheme 9

Method J

General Method for the Synthesis of Sulfonylimines

To 2-(4-aminophenyl)benzothiazole (0.5 g, 2.2 mmol) in pyridine (6 mL) is added para-toluenesulphonyl chloride (0.506 g, 2.7 mmol, 1.5 eq.) in pyridine (4 mL). The reaction mixture is heated at reflux for 10 mins, then cooled and water (10 mL) added. The white precipitate formed is collected on a filter, washed with water, and dried under vacuum to give N-[4-(benzothiazol-2-yl)phenyl]-4-methyl-benzenesulfonamide as a white solid.

To the sulfonamide (0.1 g) dissolved in methanol (2 mL) is added BTIB (1.1 eq.) in one portion as a solid. The resulting suspension is stirred at room temperature for 5 hours. The precipitate formed is collected on a filter, washed with ice cold methanol (2 mL) and dried under vacuum.

Scheme 10

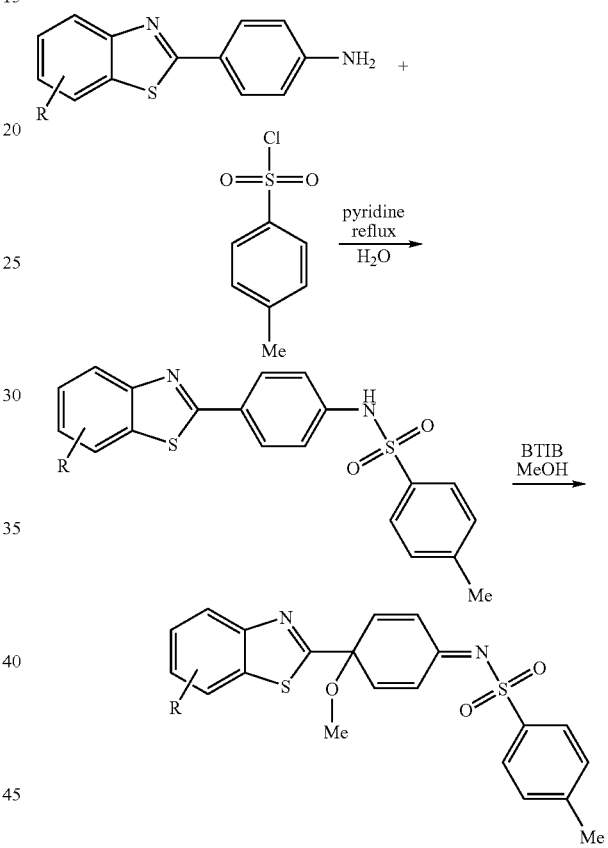

Method K

General Method for the Synthesis of Benzothiazolyl Quinols

The starting materials, 2-aminobenzothiazoles, were synthesized from the corresponding substituted anilines (see, e.g., Hutchinson et al., 2001) or were purchased from commercial suppliers (e.g., Aldrich Chemical Company, Dorset, UK).

To the 2-aminobenzothiazole (2 g) in a 60 mL flat bottomed test tube was added aqueous 50% w/v sodium hydroxide solution (10 mL) with stirring. The reaction was heated at 150° C. for 12 hours. During this time the starting material dissolved. The pH of the solution was adjusted to 6 with concentrated hydrochloric acid (~10 mL), diluted with water (10 mL) and stirred overnight. The resulting suspension was filtered and the residue washed with water and dried under vacuum to give the corresponding disulfide product.

To the disulphide (0.71 mmol) and the benzaldehyde (1.41 mmol, 2.0 eq.) in toluene (20 mL) was added triphenylphosphine (0.185 g, 0.71 mmol, 1.0 eq.) and para-toluenesulphonic acid (2 mg). The reaction mixture was heated at reflux for 3 days. After cooling, the solvent was removed in vacuo and the residue purified by flash column chromatography eluted with ethyl acetate/hexane (2/8) to give the corresponding substituted phenol product.

To the benzothiazole (0.120 g) and TEMPO (0.2 eq.) dissolved/suspended in acetonitrile (15 mL) and water (5 mL) was added BTIB (2.0 eq.), dissolved in acetonitrile (5 mL), dropwise over 5 min. After 5 min, poly(4-vinylpyridine) (4.0 equiv.) was added with stirring. After a further 5 min the reaction mixture was filtered and the residue washed with acetonitrile (2×5 mL) to give a yellow/orange filtrate. This was concentrated in vacuo and purified by flash column chromatography eluted with ethyl acetate/hexane (3/7) to give the desired quinol product.

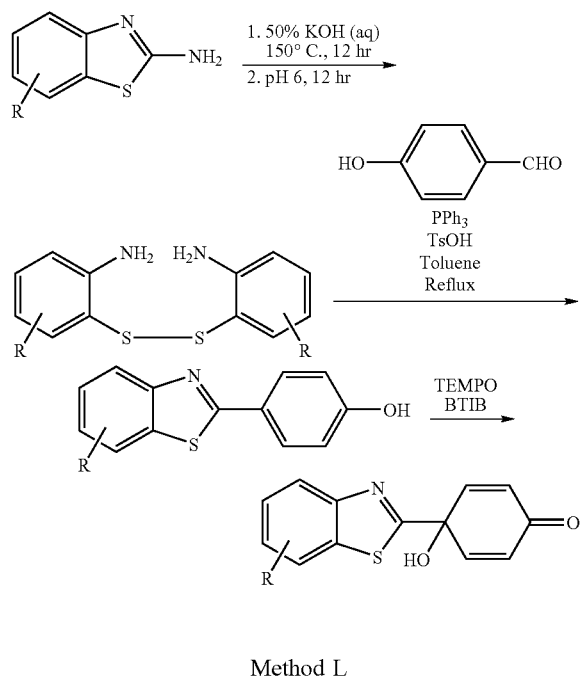

Method L

General Method for Synthesis of Cyclohexanones

To benzothiazole (3.46 g, 25.6 mmol) in dry THF (50 mL) under a nitrogen atmosphere at −78° C. was added n-butyllithium (17.1 mL of 1.5 M solution, 25.6 mmol) dropwise. The reaction was stirred for 1 hour and became yellowish in colour. To this was added 1,4-cyclohexadione-monoethyleneketal (4 g, 25.6 mmol, Aldrich Chemical Company) in one portion. The reaction was stirred at −78° C. for a further 3 hours then water (10 mL) was added and the reaction mixture allowed to rise to room temperature. The white precipitate formed was collected on a filter, washed with water (2×20 mL) then dried under vacuum. The yield of 8-benzothiazol-2-yl-1,4-dioxa-spiro[4.5]decan-8-ol was 4.403 g (59%).

The monoethylene ketal product (1.5 g, 5.15 mmol) was dissolved in acetic acid (40 mL) and concentrated hydrochloric acid (10 mL) and heated to 80° C. for 2 hours. The reaction mixture was then cooled and the volume reduced in vacuo. The remaining solution was carefully neutralised with saturated sodium hydrogen carbonate solution and extracted with ether (3×50 mL). The combined organic extracts were washed with water (2×50 mL) and dried over magnesium sulphate. Evaporation of the solvent gave the desired product as a white solid. The yield was 0.848 g (67%).

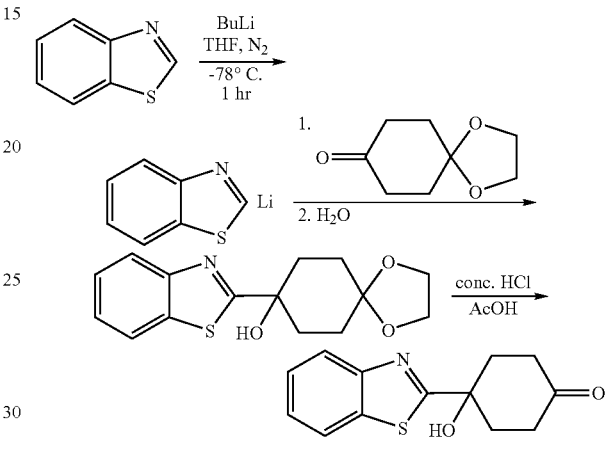

Method M

General Method for the Synthesis of Heteroaromatic Naphtho-Quinols

A solution of 4-methoxy-1-naphthol (2.76 g, 15.8 mmol) and DAIB (6.10 g, 18.9 mmol) on methanol (75 mL) was stirred at 25° C. under a nitrogen atmosphere for 1 h. The resultant dark blue solution was poured into a saturated NaHCO$_3$ (aq) solution (75 mL), then the mixture concentrated to approx. 50 mL in vacuo. The blue oil was extracted with dichloromethane (3×75 mL) and the organic layer washed with water (2×75 mL) and brine (2×75 mL), then dried (MgSO$_4$), filtered and concentrated in vacuo (water bath temperature <40° C.) to yield 4,4-dimethoxy-4H-naphthalen-1-one as a dark-blue semi-solid which was used without further purification; $^1$H NMR (CDCl$_3$) δ 8.15 (1H, d, J 8.0 Hz, ArH), 7.40–7.85 (3H, m, ArH), 6.90 (1H, d, J 12.2 Hz, H-3), 6.55 (1H, d, J 12.2 Hz, H-2), 3.15 (6H, s, OCH$_3$).

To a solution of n-butyllithium (3.4 mL of a 1.6 M solution in hexanes, 5.4 mmol) in THF (6 mL) at −78° C. was slowly added a solution of the aryl compound, e.g., benzothiophene or benzofuran (4.9 mmol) in THF (6 mL) with stirring under a nitrogen atmosphere. Following addition, the solution was stirred at −78° C. for 1 h. The lithiated heteroaromatic was then added via cannula to a stirring solution of freshly prepared 4,4-dimethoxy-4H-naphthalen-1-one (4.9 mmol) in THF (12 mL) at −78° C., followed by stirring for a further two hours. The resulting solution was then poured into brine (20 mL) and extracted using dichloromethane (3×20 mL). The combined organic layers were washed with water (2×15 mL) and brine (2×15 mL), and dried (MgSO$_4$), filtered and concentrated in vacuo. The dark oil was redissolved in acetone (10 mL), 10% aqueous acetic acid solution (10 mL) added and the mixture heated under reflux for 1 h. The solution was then allowed to cool and extracted with dichloromethane (3×20 mL). The organic layers were washed with water (2×15 mL) and brine (2×15 mL), then dried (MgSO$_4$), filtered and concentrated in vacuo to yield the crude product. Purification by column chromatography (4:1 hexane: EtOAc) then yielded the desired product.

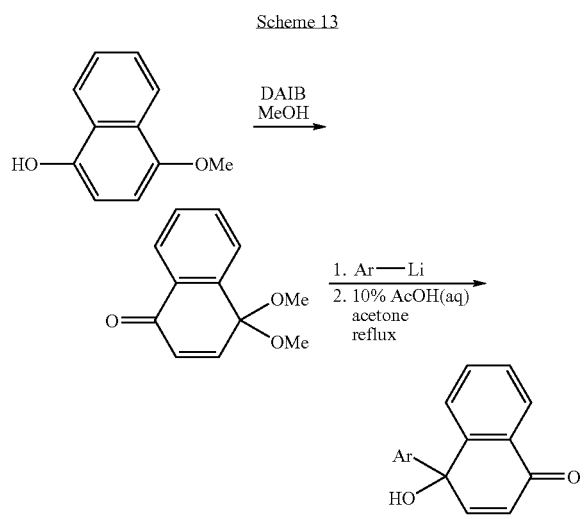

Scheme 13

Uses

The present invention provides active compounds, specifically, active antiproliferative agents, anticancer agents, antimycobacterial agents, antituberculosis agents, and/or thioredoxin/thioredoxin reductase inhibitors.

The term "active," as used herein, pertains to compounds which are capable of, e.g., inhibiting cell proliferation, treating cancer, treating mycobacterial conditions, treating tuberculosis, inhibiting thioredoxin/thioredoxin reductase, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound is active. For example, assays which may conveniently be used in order to assess the activity offered by a particular compound are described in the examples below.

Antiproliferative Applications

The present invention also provides active compounds which (a) regulate (e.g., inhibit) cell proliferation; (b) inhibit cell cycle progression; (c) promote apoptosis; or (d) a combination of one or more of these.

Thus, the present invention also provides methods of (a) regulating (e.g., inhibiting) cell proliferation; (b) inhibiting cell cycle progression; (c) promoting apoptosis; or (d) a combination of one or more of these, in vitro or in vivo, comprising contacting a cell with an effective amount of an active compound, as described herein.

One of ordinary skill in the art is readily able to determine whether or not a candidate compound regulate (e.g., inhibit) cell proliferation, etc. For example, assays which may conveniently be used to assess the activity offered by a particular compound are described in the examples below.

For example, a sample of cells (e.g., from a tumour) may be grown in vitro and an active compound brought into contact with said cells, and the effect of the compound on those cells observed. As an example of "effect," the morphological status of the cells (e.g., alive or dead, etc.) may be determined. Where the active compound is found to exert an influence on the cells, this may be used as a prognostic or diagnostic marker of the efficacy of the compound in methods of treating a patient carrying cells of the same cellular type.

The present invention further provides antiproliferative agents. The term "antiproliferative agent" as used herein, pertains to a compound which treats a proliferative condition (i.e., a compound which is useful in the treatment of a proliferative condition).

One of ordinary skill in the art is readily able to determine whether or not a candidate compound treats a proliferative condition for any particular cell type. For example, assays which may conveniently be used to assess the activity offered by a particular compound are described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

In one embodiment, the proliferative condition is renal cancer or colon cancer.

In one embodiment, the proliferative condition is renal cancer.

In one embodiment, the proliferative condition is colon cancer.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

In one embodiment, the cell is a renal cell (e.g., renal tumour cell, renal cancer cell) or a colon cell (e.g., colon tumour cell, colon cancer cell).

In one embodiment, the cell is a renal cell (e.g., renal tumour cell, renal cancer cell).

In one embodiment, the cell is a colon cell (e.g., colon tumour cell, colon cancer cell).

Anticancer Applications

Antiproliferative compounds of the present invention have application in the treatment of cancer, and so the present invention further provides anticancer agents.

The term "anticancer agent" as used herein, pertains to a compound which treats a cancer (i.e., a compound which is useful in the treatment of a cancer).

One of ordinary skill in the art is readily able to determine whether or not a candidate compound treats a cancerous condition for any particular cell type. For example, assays which may conveniently be used to assess the activity offered by a particular compound are described in the examples below.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Mycobacterial Applications

The present invention further provides antimycobacterial agents.

The term "antimycobacterial agent" as used herein, pertains to a compound which treats a mycobacterial condition/infection (i.e., a compound which is useful in the treatment of a mycobacterial condition/infection), especially M. tuberculosis.

One of ordinary skill in the art is readily able to determine whether or not a candidate compound treats a mycobacterial condition. For example, assays which may conveniently be used to assess the activity offered by a particular compound are described in the examples below.

The term "mycobacteria" is used herein in the conventional sense to refer to the genus of gram-positive, aerobic to microaerophilic, non-motile, asporogenous bacteria (order Actinomycetales, wall type IV) which are acid-fast during at least some stage of growth. The cells are straight or curved rods, ca. 0.2–0.8×1–10 µm, but may occur as coccoid forms, branched rods, or fragile filaments; some strains are capsulated. Species occur in soil as free-living saprotrophs, in water, on plants, and as parasites and pathogens of man and other animals (including fish). Tests used in the identification of mycobacteria include, e.g., the arylsulfatase test, catalase test, niacin test, nitrate reduction test, T2H test, and tween hydrolysis (see, e.g., Sonnenwirth et al., 1980). The genus includes about 40 species, including the following: M. africanum, M. avium, M. bovis, M. chelonei, M. farcinogenes, M. flavum, M. fortuitum, M. haemophilum, M. intracellulare, M. kansasii, M. leprae, M. lepraemurium, M. marinum, M. microti, M. paratuberculosis, M. phlei, M. scrofulaceum, M. senegalense, M. simiae, M. smegmatis, M. thermoresistibile, M. tuberculosis, M. ulcerans, and M. xenopi.

Tuberculosis (also known as phthisis and TB), is a chronic infectious disease of humans and animals, caused by Mycobacterium. In humans, tuberculosis is usually caused by M. tuberculosis, but may be caused, e.g., by M. bovis (acquired, e.g., from cattle). Infection occurs chiefly by inhalation (the pathogen can remain viable for weeks or months in moist or dried sputum). A lesion is formed in the lung, and from here tubercle bacilli are transported within macrophages, via the pulmonary lymphatic system, to the bloodstream, resulting in the formation of foci of infection in various parts of the body. Subsequently, as a result of antibody and cell-mediated immune responses, the foci of infection become encapsulated, forming granulomatous lesions called tubercles; a tubercle contains leucocytes, epithelioid cells, tubercle bacilli, and giant cells. A tubercle eventually becomes necrotic and undergoes caseation. Subsequently, it may calcify and remain quiescent (still containing viable tubercle bacilli); alternatively, it may discharge its contents into an adjacent region, spreading the infection, or it may rupture into a blood vessel, resulting in a massive dissemination of tubercle bacilli and the consequent formation throughout the body of numerous synchronously progressive tubercles (miliary tuberculosis). Clinical symptoms of tuberculosis include fever, chills, night sweats and weight loss. In pulmonary tuberculosis ("consumption") there is a persistent cough, initially unproductive, then productive of mucopurulent sputum (containing tubercle bacilli); in the later stages there may be dyspnoea and haemoptysis. Symptoms of extrapulmonary tuberculosis depend on the organs involved, and may include, e.g., lymphadenitis, pyuria and haematuria, meningitis, osteomyelitis, pericarditis, peritonitis, etc. Laboratory diagnosis is usually performed using a tuberculin test, by identification of tubercle bacilli (e.g., by acid-fast staining, culture, etc.) from sputum, CSF, urine sediments, biopsy specimens etc. Chemotherapy usually involves at least two drugs which are used in combination to discourage the emergence of resistant strains. Isoniazid (INH) with ethambutol is a commonly used combination; other anti-tuberculosis drugs include para-aminosalicylic acid (PAS), streptomycin, rifamycins (e.g., rifampicin), pyrazinamide, carpreomycin, and cycloserine.

Thioredoxin/Thioredoxin Reductase Applications

The present invention also provides active compounds which inhibit thioredoxin/thioredoxin reductase activity.

The term "inhibiting thioredoxin/thioredoxin reductase," as used herein, includes: inhibiting thioredoxin/thioredoxin reductase activity; inhibiting the formation of thioredoxin/thioredoxin reductase complexes; and inhibiting the activity of thioredoxin/thioredoxin reductase complexes.

One of ordinary skill in the art is readily able to determine whether or not a candidate compound inhibits thioredoxin/thioredoxin reductase activity. For example, one assay which may conveniently be used in order to assess the thioredoxin/thioredoxin reductase inhibition offered by a particular compound is described in the examples below.

Thus, the present invention also provides methods of inhibiting thioredoxin/thioredoxin reductase in a cell, comprising contacting said cell with an effective amount of an active compound. Such a method may be practised in vitro or in vivo. In one embodiment, the method is performed in vitro. In one embodiment, the method is performed in vivo. Preferably, the active compound is provided in the form of a pharmaceutically acceptable composition.

The present invention also provides active compounds which are anti-thioredoxin/thioredoxin reductase agents, and which treat a condition mediated by thioredoxin/thioredoxin reductase.

The term "a condition mediated by thioredoxin/thioredoxin reductase," as used herein pertains to a condition in which thioredoxin/thioredoxin reductase and/or the action of thioredoxin/thioredoxin reductase is important or necessary, e.g., for the onset, progress, expression, etc. of that condition, or a condition which is known to be treated by thioredoxin/thioredoxin reductase inhibitors.

The thioredoxins are ubiquitous proteins containing a conserved -Trp-Cys-Gly-Pro-Cys-Lys- redox catalytic site. Mammalian thioredoxin family members include thioredoxin-1 (Trx1), mitochondrial thioredoxin-2 (Trx2), and a larger thioredoxin-like protein, $p32^{TrxL}$. Thioredoxin is reduced by NADPH and thioredoxin reductase and, in turn reduces oxidized cysteine groups on proteins. When thioredoxin levels are elevated there is increased cell growth and resistance to the normal mechanism of programmed cell death. An increase in thioredoxin levels seen in many human primary cancers compared to normal tissue appears to contribute to increased cancer cell growth and resistance to chemotherapy. Mechanisms by which thioredoxin increases cell growth include an increased supply of reducing equivalents for DNA synthesis, activation of transcription factors that regulate cell growth, and an increase in the sensitivity of cells to other cytokines and growth factors. The mechanisms for the inhibition of apoptosis by thioredoxin are just now being elucidated. Because of its role in stimulating cancer cell growth and as an inhibitor of apoptosis, thioredoxin offers a target for the development of drugs to treat and prevent cancer. See, for example, the review article by Powis et al., 2000, and references cited therein.

Thioredoxin was first described in 1964 as a small redox protein from *Escherichia coli*. Mammalian thioredoxin was reported in 1967 as a redox protein present in rat Novikoff hepatoma cells. Thioredoxin was subsequently rediscovered under other names, including: (i) adult T cell leukemia-derived factor (ADF), an interleukin-2 (IL-2) receptor-inducing factor produced by human T-lymphotrophic virus type 1 (HTLV 1)-infected T cells; and, (ii) early pregnancy factor, part of a complex in the serum of pregnant animals that increases the complement-dependent inhibition of lymphocyte binding to heterologous blood cells. These proteins were shown to be identical when the correct predicted amino acid sequence of thioredoxin was published, and they are all now referred to as thioredoxin (Trx). A truncated form of thioredoxin, eosinophil cytotoxicity enhancing factor, has also been described.

Members of the thioredoxin family of proteins have as a conserved catalytic site -Trp-Cys-Gly-Pro-Cys-Lys- that undergoes reversible oxidation to the cysteine-disulfide (Trx-$S_2$) form through the transfer of reducing equivalents to a disulfide substrate (X-$S_2$). The oxidized thioredoxin is reduced back to the cysteine-thiol form [Trx-$(SH)_2$] by the NADPH-dependent flavoprotein thioredoxin reductase (TR).

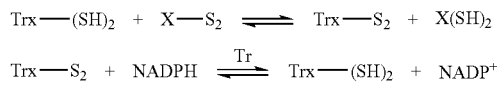

Mammalian thioredoxin reductases are homodimeric, flavin adenine dinucleotide-containing proteins with a penultimate C-terminal selenocysteine (SeCys) residue. The conserved redox catalytic site of thioredoxin reductase, -Cys-Val-Asn-Val-Gly-Cys-, undergoes reversible oxidation reduction in much the same way as thioredoxin. Although selenocysteine is essential for the full activity of mammalian thioredoxin reductases, human thioredoxin can be relatively efficiently reduced by the nonselenocysteine-containing bacterial thioredoxin reductase. To date, two human thioredoxin reductases have been cloned, TR1, found predominantly in the cytosol, and TR2, which has a putative mitochondrial import sequence.

Two forms of thioredoxin have been cloned, thioredoxin-1 (Trx-1) and thioredoxin 2 (Trx-2). Human Trx-1 is a 104 amino acid protein with a molecular weight of 12 kDa that contains two catalytic site Cys residues -Trp-$Cys^{32}$-Gly-Pro-$Cys^{35}$-Lys- found in all thioredoxin proteins, as well as three additional Cys residues, $Cys^{62}$, $Cys^{69}$, and $Cys^{73}$, that are not found in bacterial thioredoxins. Trx-1s from a number of other mammalian species, including chicken, rat, mouse, and bovine, have been cloned.

Thioredoxin variously acts as a growth factor, and antioxidant, a cofactor, as a transcription factor regulator, and as an inhibitor of apoptosis.

Studies with a variety of human primary tumors have shown that thioredoxin is overexpressed in the tumor compared to levels in the corresponding normal tissue. Recent immunohistochemical studies using paraffin-embedded tissue sections have shown that thioredoxin expression is increased in more than half of human primary gastric cancers. The thioredoxin levels showed a highly significant positive correlation (p<0.001) with cell proliferation measured by nuclear proliferation antigen and a highly significant negative correlation (p<0.001) with apoptosis measured by the terminal deoxynucleotidyl transferase assay. A comparison of 49,000 human gene transcripts in human normal colon epithelium and colorectal cancer by the serial analysis of gene expression (SAGE) technique revealed 548 differentially expressed transcripts. Thioredoxin mRNA was increased 2-fold in colon cancer cell lines and 4-fold in colon tumors.

Plasma and serum levels of thioredoxin, which in normal individuals are between 10 and 80 ng/ml (0.86.6 nM), have been reported to be elevated almost 2-fold in patients with hepatocellular carcinoma and to decrease following surgical removal of the tumor. Serum thioredoxin was not elevated in patients with other forms of liver disease such as chronic hepatitis or liver cirrhosis.

The growth-stimulating and transforming effects of thioredoxin, together with the finding that it is overexpressed by a number of human primary tumors, raise the possibility that thioredoxin is a factor leading to aggressive tumor growth and poor patient prognosis. Because thioredoxin has also been shown to inhibit apoptosis caused by a number of anticancer drugs and to be a cause of resistance to the cytotoxic effects of some anticancer drugs, it is possible that increased thioredoxin could be a cause of resistance to chemotherapy. These findings make thioredoxin an attractive target for the development of drugs to inhibit cancer cell growth. Several such compounds have been identified. They include PX-12 (1-methylhydroxypropyl 2-imidazoloyl disulfide), which was identified as an inhibitor of thioredoxin binding to the $Cys^{73}$ residue. The median $IC_{50}$ for growth inhibition of a variety of cell lines by PX-12 is 8.1 µM. PX-12 has been shown to have in vivo antitumor activity against human tumor xenografts in scid mice and chemopreventive activity in min (multiple intestinal neoplasia) mice, which have a germline mutation in the APC gene seen in familial adenomatous polyposis. The growth inhibition by compound PX-12 in the NCI 60 human tumor cell line panel was significantly correlated with the expression of thioredoxin mRNA. Several other inhibitors of thioredoxin have been identified by the COMPARE program from over 50,000 compounds tested by the National Cancer Institute as having a pattern of cell killing activity in the 60 human tumor cell line panel similar to PX-12. One of these compounds, NSC-131233 (2,5-bis[(dimethylamino)methyl] cyclopentanone) is an irreversible inhibitor of thioredoxin with a $K_i$ of 1.0 µM.

The thioredoxins are a family of small redox proteins whose functions include the regulation of cell growth, programmed cell death, and the development of the organism. When thioredoxin levels are elevated in cells, there is increased cell growth and resistance to normal mechanisms of programmed cell death. An increase in thioredoxin levels seen in many human primary cancers compared to normal tissue may be a contributing factor leading to increased cancer cell growth and resistance to chemotherapeutic drugs. The mechanism for the increase in thioredoxin in cancer cells remains unknown at this time. Because of its role as a stimulator of cell growth and an inhibitor of apoptosis, thioredoxin is a target for the development of drugs to treat and, possibly, prevent cancer.

Methods of Treatment, Etc.

The invention further provides methods of treatment for example, of a proliferative condition, cancer, a mycobacterial condition, tuberculosis, a condition mediated by thioredoxin/thioredoxin reductase, a condition known to be treated by thioredoxin/thioredoxin reductase inhibitors, or other condition as described herein, comprising administering to a subject in need of treatment a therapeutically-effective amount of an active compound, preferably in the form of a pharmaceutical composition.

The invention further provides active compounds for use in a method of treatment of the human or animal body, for example, in the treatment of a proliferative condition, cancer, a mycobacterial condition, tuberculosis, a condition mediated by thioredoxin/thioredoxin reductase, a condition known to be treated by thioredoxin/thioredoxin reductase inhibitors, or other condition as described herein.

The invention further provides the use of an active compound for the manufacture of a medicament, for example, for the treatment of a proliferative conditions, cancer, a mycobacterial condition, tuberculosis, a condition mediated by thioredoxin/thioredoxin reductase, a condition known to be treated by thioredoxin/thioredoxin reductase inhibitors, or other condition as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage form comprising an active compound, which is effective for producing some desired therapeutic effect, commensurate with a reasonable benefit-trisk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Active compounds may also be used, as described above, in combination therapies, that is, in conjunction with other agents, for example, cytotoxic agents.

Additional Uses

Active compounds may also be used as cell culture additives to inhibit thioredoxin/thioredoxin reductase, for example, in order to regulate cell proliferation in vitro.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other antiproliferative agents, anticancer agents, antimycobacterial agents, thioredoxin/thioredoxin reductase inhibitors, etc.

Kits

One aspect of the invention pertains to a kit comprising (a) the active ingredient, preferably provided in a suitable container and/or with suitable packaging; and (b) instructions for use, for example, written instructions on how to administer the active compound.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be a protoctista, an alga, or a protozoan.

The subject may be a plant, an angiosperm, a dicotyledon, a monocotyledon, a gymnosperm, a conifer, a ginkgo, a cycad, a fern, a horsetail, a clubmoss, a liverwort, or a moss.

The subject may be an animal.

The subject may be a chordate, an invertebrate, an echinoderm (e.g., starfish, sea urchins, brittlestars), an arthropod, an annelid (segmented worms) (e.g., earthworms, lugworms, leeches), a mollusk (cephalopods (e.g., squids, octopi), pelecypods (e.g., oysters, mussels, clams), gastropods (e.g., snails, slugs)), a nematode (round worms), a platyhelminthes (flatworms) (e.g., planarians, flukes, tapeworms), a cnidaria (e.g., jelly fish, sea anemones, corals), or a porifera (e.g., sponges).

The subject may be an arthropod, an insect (e.g., beetles, butterflies, moths), a chilopoda (centipedes), a diplopoda (millipedes), a crustacean (e.g., shrimps, crabs, lobsters), or an arachnid (e.g., spiders, scorpions, mites).

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening: agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 2nd edition, 1994.

The formulations may be prepared by any methods well known in the art of pharmacy. Such methods include the step of bringing into association the active compound with a carrier +which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in a the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g, by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 µg to about 100 mg per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

All compounds were characterised by elemental microanalysis (C, H, and N values within 0.4% of theoretical values). Melting points were determined using a Gallenkamp melting point apparatus and are reported uncorrected. $^1$H and $^{13}$C NMR spectra were recorded using a Bruker ARX250 spectrometer. IR spectra (as KBr discs) were determined using a Mattson 2020 Galaxy series FT-IR spectrophotometer. Mass spectra were recorded; on an AEI MS-902 or a VG Micromass 7070E spectrometer. TLC systems for routine monitoring of reaction mixtures, and for confirming the homogeneity of analytical samples used Kieselgel 60F$_{254}$ (0.25 mm) silica gel TLC aluminum sheets. Sorbsil silica gel C 60-H (40–60 μm) was used for flash chromatographic separations. All reactions were carried out under inert atmosphere using anhydrous reagents and solvents. THF was dried and purified before use by distillation from sodium-benzophenone. All other commerical materials were used as received.

Example 1

4-(Benzofuran-2-yl)-4-hydroxy-2,5-cyclohexadien-1-one (Q01)

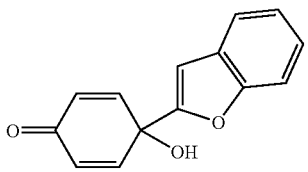

The title compound was synthesised according to Method A, described above. Yield 82%; mp 106.5–108.5° C.; $^1$H NMR (CDCl$_3$) δ 7.57 (1H, d, J 7.5 Hz, ArH), 7.49 (1H, d, J 7.5 Hz, ArH), 7.29 (2H, m, ArH), 7.16 (2H, d, J 10.3 Hz, H-3', H-5'), 6.77 (1H, s, H-3), 6.34 (2H, d, J 10.3 Hz, H-2', H-6'), 2.83 (1H, s, OH); IR$^{-1}$ 3368, 3270, 1669, 1622, 1175, 1036, 905, 745; MS (Cl) m/z 227 (M$^+$+1), 209; Anal. (C$_{14}$H$_{10}$O$_3$.¼H$_2$O) C,H.

Example 2

4-(Benzothiophen-2-yl)-4-hydroxy-2,5-cyclohexadien-1-one (Q02)

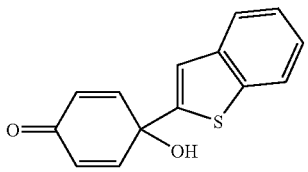

The title compound was synthesised according to Method A, described above. Yield 60%; mp 185–188° C.; $^1$H NMR (CDCl$_3$) δ 7.83 (1H, dd, J 4.3, 5.0 Hz, ArH), 7.73 (1H, dd, J 4.3, 5.0 Hz, ArH), 7.37 (2H, m, ArH), 7.26 (1H, s, H-3), 7.10 (2H, d, J 8.3 Hz, H-3', H-5'), 6.31 (2H, d, J 8.3 Hz, H-2', H-6'), 2.71 (1H, s, OH); IR$^{-1}$41; MS (Cl) m/z 243 (M$^+$+1), 225 (—H$_2$O); Anal. (C$_{14}$H$_{10}$O$_2$S) C, H, N.

Example 3

4-(Indol-2-yl)-4-hydroxy-2,5-cyclohexadien-1-one (Q03)

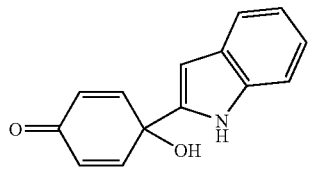

To N—(N,N-dimethylaminomethyl)indole (0.565 g, 3.2 mmol) dissolved in THF (10 mL) under nitrogen was added n-butyllithium (2.02 mL of 1.6 M solution, 3.2 mmol) at −78° C. After 10 minutes, the reaction was warmed to 0° C. over 35–40 minutes, then cooled again to −78° C. and 4,4-dimethoxycyclohexadienone (0.5 g, 3.2 mmol) added. After stirring at −78° C. for one hour, the reaction was warmed to room temperature over several hours and quenched by the addition of water (20 mL), then extracted with diethylether (2×20 mL). The organic fractions were combined, dried over sodium sulphate and concentrated in vacuo. The residue was dissolved in ethanol:THF (1:1, 10 mL) and sodium borohydride (0.135 g, 3.5 mmol, 1.1 equivalents) added and the reaction stirred at reflux for five hours. After cooling to room temperature, the solvent was removed in vacuo. The residue was dissolved in acetone (20 mL) and 10% aqueous acetic acid (20 mL) was added and the reaction stirred overnight. After cooling to room temperature, the acetone was removed under reduced pressure and the aqueous phase extracted with ether (2×20 mL). The combined organic layers were washed with saturated sodium hydrogen carbonate solution (20 mL) and water (20 mL) then dried and concentrated under vacuum. The title quinol was purified by flash column chromatography eluted with ethyl acetate:hexane (1:4).

The yield was 26%; mp 133° C.; $^1$H NMR (CDCl$_3$) δ 8.66 (1H, s), 7.58 (1H, d, J 7.8 Hz, ArH), 7.41 (1H, d, J 8.0 Hz, ArH), 7.25 (1H, t, J 7.0 Hz, ArH), 7.17 (1H, t, J 7.0 Hz, ArH), 7.07 (2H, d, J 10.3 Hz, H-3', H-5'), 6.44 (1H, s, H-3), 6.27 (2H, d, J 10.3 Hz, H-2', H-6'); IR 3405, 2361, 2342, 1667, 1620, 1454, 1289, 901, 856, 799, 748 cm$^{-1}$; MS (El) m/z 225 (M$^+$), 209, 117; Acc Mass (Cl) C$_{14}$H$_{11}$NO$_2$ requires M$^+$+1 226.0868, found M$^+$+1 226.0866; TLC R$_f$ 0.1 (EtOAc:hexane 2:8).

Example 4

4-(Benzoxazol-2-yl)-4-hydroxy-2,5-cyclohexadien-1-one (Q04)

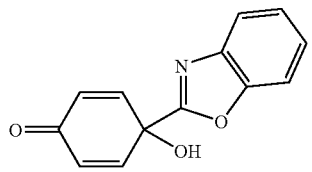

The title compound was synthesised according to Method A, described above. Yield 30%; mp 116–117° C.; $^1$H NMR (CDCl$_3$) δ 7.78 (1H, dd, J 1.8, 7.9 Hz, H-4), 7.58 (1H, dd, J 1.8, 8.0 Hz, H-7), 7.44 (2H, m, H-5, H-6), 7.12 (2H, d, J 9.3 Hz, H-3', H-5'), 6.45 (2H, d, J 9.3 Hz, H-2', H-6'); IR 3421, 3213, 1666, 1622, 1167, 1064, 925, 856, 744 cm$^{-1}$; MS (El) m/z 227 (M$^+$), 211, 119. Anal. (C$_{14}$H$_{10}$O$_3$) C, H, N.

Example 5

4-(Benzothiazol-2-yl)-4-hydroxy-2,5-cyclohexadien-1-one (Q05)

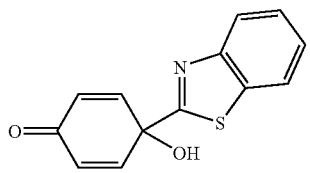

The title compound was synthesised according to Method A, described above. Yield 48%; mp 63–66° C.; $^1$H NMR (CDCl$_3$) δ 8.03 (1H, dd, J 1.0, 8.0 Hz, H-4), 7.89 (1H, dd, J 1.0, 7.8 Hz, H-7), 7.52 (1H, td, J 1.3, 7.3 Hz, H-5); 7.43 (1H, td, J 1.3, 8.0 Hz, H-6), 7.02 (2H, dd, J 1.9, 10.0 Hz, H-3', H-5'), 6.35 (2H, d, J 10.0 Hz, H-2', H-6'); IR 3482, 3165, 1667, 1622, 1150, 1081, 764 cm$^{-1}$; MS (CI) m/z 244 (M$^+$+1); Anal. (C$_{13}$H$_9$NO$_2$S) C, H, N.

Example 6

4-(Benzothiazol-2-yl)-3-chloro-4-hydroxy-2,5-cyclohexadien-1-one (Q06)

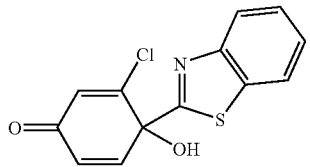

The title compound was synthesised according to Method A, described above, from benzothiazole and 2-chloro-4,4-dimethoxycyclohexa-2,5-dien-1-one (see, e.g., McKillop et al., 1993).

Yield 58%; mp 140–143° C.; $^1$H NMR (CDCl$_3$) δ 8.06 (1H, dd, J 0.8, 7.5 Hz, H-4), 7.90 (1H, dd, J 0.8, 7.5 Hz, H-7), 7.55 (1H, dt, J 1.5, 8.0 H-5), 7.46 (1H, dt, J 1.5, 8.0 Hz, H-6), 6.99 (1H, d, J 9.8 Hz, H-5'), 6.60 (1H, d, J 1.8 Hz, H-2'), 6.36 (1H, dd, J 1.8, 9.8 Hz, H-6'); IR 3376, 3061, 1657, 1616, 1314, 1144, 1074, 980, 910, 750, 592 cm$^{-1}$; MS (Cl) m/z 278/280 (M$^+$+1), 260/262; Anal. (C$_{13}$H$_8$ClNO$_2$S) C, H, N.

Example 7

4-(Benzimidazol-2-yl)-4-hydroxy-2,5-cyclohexadien-1-one (Q07)

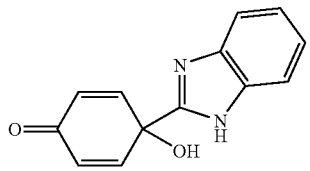

To N—(N-pyrrolidinomethyl)benzimidazole (0.571 g, 2.84 mmol) in dry THF (20 mL) under nitrogen was added n-butyllithium (1.25 mL of 2.5 M solution, 3.12 mmol) dropwise with stirring at −78° C. After two hours the reaction was allowed to rise to room temperature and 2 M HCl (20 mL) was added and the volume reduced under vacuum. The pH was adjusted to 6–7 with 1 M sodium hydrogen carbonate solution to form a white precipitate which was collected on a filter, washed with water and dried under vacuum.

The yield was 47%; mp 234° C.; $^1$H NMR (DMSO-d$_6$) δ 12.66 (1H, s), 7.51 (1H, d, J 6.6 Hz, ArH), 7.44 (1H, d, J 5.8 Hz, ArH), 7.13 (2H, d, J 10.1 Hz, H-3', H-5'), 7.12 (2H, m, ArH), 6.95 (1H, s), 6.19 (2H, d, J 10.1 Hz, H-2', H-6'); IR 3264, 3052, 1667, 1618, 1451, 1406, 1275, 1086, 1047, 860, 743 cm$^{-1}$; MS (EI) m/z 226 (M$^+$), 210, 118; Anal. (C$_{13}$H$_{10}$N$_2$O$_2$·¼H$_2$O) C, H, N.

Example 8

4-(Naphth-2-yl)-4-hydroxy-2,5-cyclohexadien-1-one (Q08)

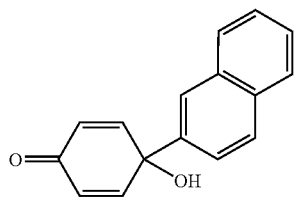

The title compound was synthesised according to Method A, described above. Yield 50%; mp 137° C.; $^1$H NMR (CDCl$_3$) δ 8.04 (1H, d, J 1.8 Hz, H-1), 7.84 (3H, m, ArH), 7.49 (3H, m, ArH), 6.97 (2H, d, J 10.0 Hz, H-3', H-5'), 6.28 (2H, d, J 10.0 Hz, H-2', H-6'); IR 3422, 3052, 1661, 1620, 1393, 1117, 1065, 976, 868, 818, 750 cm$^{-1}$; MS (EI) m/z 236 (M$^+$), 220, 128; Anal. (C$_{16}$H$_{12}$O$_2$) C, H.

Example 9

4-(Naphth-1-yl)-4-hydroxy-2,5-cyclohexadien-1-one (Q09)

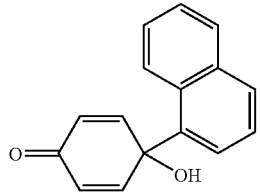

The title compound was synthesised according to Method A, described above. Yield 89%; mp 117–118° C.; $^1$H NMR (CDCl$_3$) δ 8.49 (1H, m, ArH), 7.89 (3H, m, ArH), 7.52 (3H, m, ArH), 7.26 (2H, d, J 9.0 Hz, ArH), 6.37 (2H, d, J 10.1 Hz, H-2, H-6), 2.67 (1H, s, OH); IR 3439, 3300, 1663, 1620, 1381, 1344, 1036, 1017, 862, 781 cm$^{-1}$; MS (EI) m/z 236 (M$^+$), 220, 128; Anal. (C$_{16}$H$_{12}$O$_2$) C, H.

Example 10

4-(Quinolin-3-yl)-4-hydroxy-2,5-cyclohexadien-1-one (Q10)

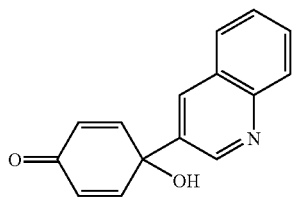

The title compound was synthesised according to Method A, described above. Yield 42%; mp 183–184° C.; $^1$H NMR (CDCl$_3$) δ 8.93 (1H, s, H-2), 8.34 (1H, d, J 2.3 Hz, H-4), 8.13 (1H, d, J 8.0 Hz, ArH), 7.85 (1H, d, J 9.0 Hz, ArH), 7.76 (1H, dt, J 1.5, 7.8 Hz, ArH), 7.60 (1H, dt, J 1.0, 7.6 Hz, ArH), 6.97 (2H, d, J 10.0 Hz, H-3', H-5'), 6.31 (2H, d, J 10.0 Hz, H-2', H-6'); IR 3048, 2766, 1663, 1624, 1497, 1279, 1163, 1069, 868, 748 cm$^{-1}$; MS (El) m/z 237 (M$^+$), 221, 129; Anal. (C$_{15}$H$_{11}$NO$_2$) C, H, N.

Example 11

4-Phenyl-4-hydroxy-2,5-cyclohexadien-1-one (Q11)

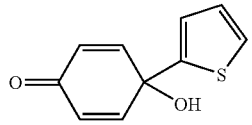

The title compound was synthesised according to Method A, described above. Yield 79%; mp 102–103° C. (lit. 99–100° C.); $^1$H NMR (CDCl$_3$) δ 7.49–7.31 (5H, m, ArH), 6.89 (2H, d, J 10.1 Hz, H-3', H-5'), 6.19 (2H, d, J 10.1 Hz, H-2', H-6').

Example 12

4-(Pyridin-2-yl)-4-hydroxy-2,5-cyclohexadien-1-one (Q12)

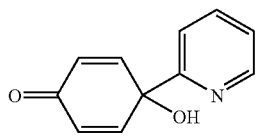

The title compound was synthesised according to Method A, described above. Yield 55%; mp 116–117° C.; $^1$H NMR (CDCl$_3$) δ 8.58 (1H, m, ArH), 7.72 (1H, dt, J 1.8, 7.6 Hz, ArH), 7.31 (2H, m, ArH), 6.76 (2H, d, J 10.3 Hz, H-3', H-5'), 6.28 (2H, d, J 10.3 Hz, H-2', H6'); IR 3131, 1670, 1626, 1439,1397, 1167, 1105, 1063, 963, 862, 795 cm$^{-1}$; MS (El) m/z 187 (M$^+$), 171, 79; Anal. (C$_{11}$H$_9$NO$_2$·¼H$_2$O) C, H, N.

Example 13

4-(Thiophen-2-yl)-4-hydroxy-2,5-cyclohexadien-1-one (Q13)

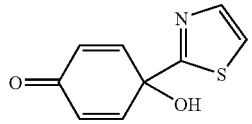

The title compound was synthesised according to Method A, described above. Yield 70%; mp 103° C.; $^1$H NMR (CDCl$_3$) δ 7.34 (1H, m, ArH), 7.07 (2H, d, J 10.1 Hz, H-3', H-5'), 7.02 (2H, m, ArH), 6.22 (2H, d, J 10.1 Hz, H-2', H-6'), 3.44 (1H, s, OH); IR 3358, 3128, 1665, 1613, 1398, 1055, 1034, 932, 903, 696 cm$^{-1}$; MS (El) m/z 192 (M$^+$), 176, 84; Anal. (C$_{10}$H$_8$O$_2$S) C, H, N.

Example 14

4-(Thiazol-2-yl)-4-hydroxy-2,5-cyclohexadien-1-one (Q14)

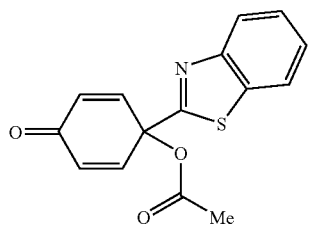

The title compound was synthesised according to Method A, described above. Yield 57%; mp 138–139° C.; $^1$H NMR (CDCl$_3$) δ 7.81 (1H, d, J 3.2 Hz, ArH); 7.46 (1H, d, J 3.2 Hz, ArH), 7.01 (2H, d, J 10.1 Hz, H-3', H-5'), 6.33 (2H, d, J 10.1 Hz, H-2', H-6'), 4.41 (1H, s, OH); IR$^{-1}$ 3109, 2805, 1674, 1628, 1497, 1148, 1069, 937, 910, 750; MS (El) m/z 193 (M$^+$), 177, 85; Anal. (C$_9$H$_7$NO$_2$S) C, H, N.

Example 15

4-Acetoxy-4-(benzothiazol-2-yl)-2,5-cyclohexadien-1-one (Q15)

The title compound was synthesised according to Method D, described above. Yield 24%; mp 101° C.; IR $^1$H (DMSO-d$_6$) δ 8.18 (1H, m, 4',7'-H), 8.04 (1H, m, 4',7'-H), 7.54 (2H, m, 5',6'-H), 7.37 (2H, d, J 10.1 Hz, 3,5-H), 6.45 (2H, d, J 10.1 Hz, 2,6-H), 2.22 (3H, s, O$_2$CCH$_3$); (KBr Disc) λ$_{max}$ 3050, 1753, 1670, 1630, 1217, 1051, 941, 764 cm$^{-1}$; m/z 286 (M$^+$+1), 228 (M$^+$—CH$_2$CO$_2$), 226 (M$^+$—CH$_3$CO$_2$H); C$_{15}$H$_{11}$NO$_3$S requires C 63.14, H 3.89, N 4.91; found C 63.14, H 3.88, N 4.87%.

Example 16

4-Methoxy-4-phenyl-2,5-cyclohexadien-1-one (Q16)

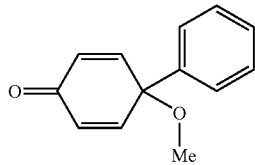

The title compound was synthesised according to Method E, described above. Yield 54%; mp 89° C. (lit. 88–90° C.); $^1$H NMR (CDCl$_3$) δ 7.48–7.30 (5H, m, ArH); 6.80 (2H, d, J 10.2 Hz, H-3, H-5); 6.40 (2H, d, J 10.2 Hz, H-2, H-6); 3.34 (3H, s, OCH$_3$).

Example 17

4-(Benzothiazol-2-yl)-4-methoxy-2,5-cyclohexadien-1-one (Q17)

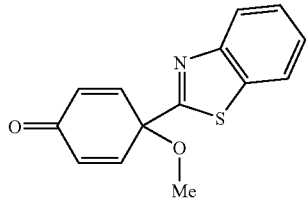

The title compound was synthesised according to Method E, described above. Yield 32%; mp 123° C.; $^1$H (CDCl$_3$) δ 8.05 (1H, d, J 7.8 Hz, 4'/7'-H), 7.94 (1H, d, J 8.0 Hz, 4'/7'-H), 7.49 (1H, td, J 1.3, 7.8 Hz, 5'/6'-H), 7.47 (1H, td, J 1.3, 7.5 Hz, 5'/6'-H), 6.98 (2H, d, J 9.5 Hz, 2,6-H), 6.57 (2H, d, J 9.0 Hz, 3,5-H), 3.51 (3H, s, OCH$_3$); IR (KBr Disc) $\lambda_{max}$ 2951, 1670, 1503, 1385, 1161, 1094, 860, 762 cm$^{-1}$.

Example 18

4-(Benzothiazol-2-yl)-4-ethoxy-2,5-cyclohexadien-1-one (Q18)

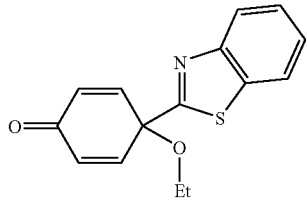

The title compound was synthesised according to Method E, described above. Yield 19%; mp 59° C.; $^1$H (CDCl$_3$) δ 8.04 (1H, dd, J 1.0, 7.0 Hz, 4'/7'-H), 7.94 (1H, dd, J 1.3, 8.0 Hz, 4'/7'-H), 7.51 (1H, td, J 1.5, 7.8 Hz, 5'/6'-H), 7.44 (1H, td, J 1.5, 7.8 Hz, 5'/6'-H), 7.01 (2H, d, J 10.3 Hz, 2,6-H), 6.53 (2H, d, J 10.3 Hz, 3,5-H), 3.70 (2H, q, J 6.8 Hz, CH$_2$), 1.32 (3H, t, J 7.0 Hz, CH$_3$); $^{13}$C (CDCl$_3$) δ 185.4 (C), 170.8 (C), 153.4 (C), 147.0 (CH), 135.6 (C), 131.7 (CH), 126.7 (CH), 126.0 (CH), 124.0 (CH), 122.1 (CH), 76.5 (C), 61.6 (CH$_2$), 16.2 (CH$_3$); IR (KBr Disc) $\lambda_{max}$ 2980, 1667, 1626, 1399, 1174, 1082, 866, 758 cm$^{-1}$; C$_{15}$H$_{13}$NO$_2$S requires M 271.0667, found M$^+$ 271.0672.

Example 19

4-(Benzothiazol-2-yl)-4-n-propoxy-2,5-cyclohexadien-1-one (Q19)

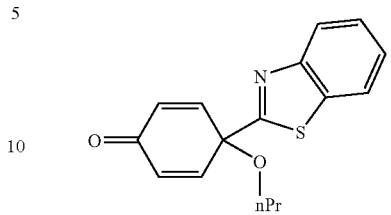

The title compound was synthesised according to Method E, described above. Yield 35%; $^1$H NMR (CDCl$_3$) δ 8.00 (1H, m, H-5', H-6'); 7.43 (2H, m, H4', H-7'); 6.94 (2H, d, J 10.3 Hz, H-3, H-5); 6.50 (2H, d, J=10.3 Hz, H-2, H-6); 3.55 (2H, t, J 6.5 Hz, OCH$_2$); 1.70 (2H, m, CH$_2$CH$_2$CH$_3$); 1.00 (3H, J 7.5 Hz, CH$_3$).

Example 20

4-(Benzothiazol-2-yl)-4-(3-propargyloxy)-2,5-cyclohexadien-1-one (Q20)

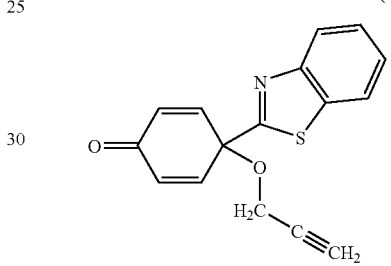

The title compound was synthesised according to Method E, described above. Yield 30%; $^1$H NMR (CDCl$_3$) δ 8.03 (1H, m, H-5', H-6'); 7.93 (1H, m, H-5', H-6'); 7.49 (2H, m, H4', H-7'), 7.06 (2H, d, J 10.3 Hz, H-3, H-5); 6.55 (2H, d, J 10.3 Hz, H-2, H-6); 4.31 (2H, d, J 2.3 Hz, OCH$_2$); 2.57 (1H, t, J 2.5 Hz, C≡CH).

Example 21

4-acetoxy-4-phenyl-2,5-cyclohexadien-1-one (Q21)

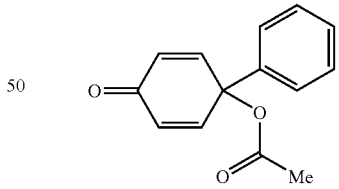

To 4-hydroxy-4-phenyl-2,5-cyclohexadienone (0.335 g, 1.8 mmol), acetic anhydride (0.276 g, 2.7 mmol, 1.5 equivalents) and triethylamine (0.273 g, 2.7 mmol, 1.5 equivalents) dissolved in dichloromethane (20 mL) was added 4-dimethylaminopyridine (DMAP) (0.044 g, 0.36 equivalents). The reaction mixture was stirred for 24 hours at room temperature, washed with 1 M HCl (20 mL) then saturated sodium hydrogen carbonate solution (2×20 mL) and the organic layer dried over magnesium sulphate. Removal of the solvent in vacuo gave an oil which was dissolved in ether, filtered and the solvent removed in vacuo to gave the title compound as a white solid. The yield was 62%; mp 100–101° C. (lit. 106–109° C.); $^1$H NMR (CDCl$_3$) δ 7.48–7.36 (5H, m, ArH); 6.99 (2H, d, J 19.2 Hz, H-3, H-5); 6.36 (2H, d, J 10.2 Hz, H-2, H-6); 2.22 (3H, s, O$_2$CCH$_3$).

Example 22

3,5-Di(ethylthio)-4-hydroxy-4-phenylcyclohexan-1-one (Q22)

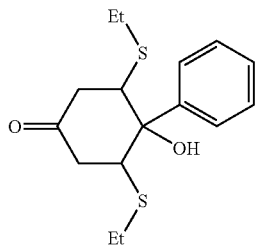

The title compound was synthesised according to Method H, described above. Yield 72%; mp 49–50° C.; $^1$H NMR (CDCl$_3$) δ 7.44–7.28 (5H, m, Ar—H); 3.40 (2H, dd, J 5.0, 13.5 Hz, H-3, H-5); 2.85 (2H, t, J 13.8 Hz, H-2, H-6); 2.65 (2H, m, H-2, H-6); 1.95–1.72 (4H, m, SCH$_2$); 0.93 (6H, t, J 7.4 Hz, CH$_3$).

Example 23

4-Hydroxy-4-phenyl-3,5-di(phenylthio)-cyclohexan-1-one (Q23)

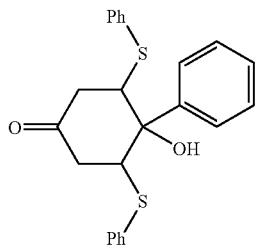

The title compound was synthesised according to Method H, described above. Yield 56%; mp126–7° C.; $^1$H NMR (CDCl$_3$) δ 7.29–7.01 (15H, m, Ar—H); 3.73 (2H, dd, J4.7, 13.5Hz, H-3, H-5); 3.02 (2H, t, J 14.0 Hz, H-2, H-6); 2.72 (2H, m, H-2, H-6).

Example 24

4-Hydroxy-4-phenyl-3,5-di[(phenyl)methylthio]-cyclohexan-1-one (Q24)

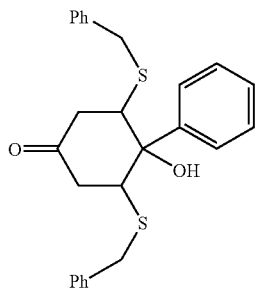

The title compound was synthesised according to Method H, described above. Yield 79%; mp 120° C.; $^1$H NMR (CDCl$_3$) δ 7.42 (3H, m, Ar—H); 7.25 (8H, m, Ar—H); 6.99 (4H, m, Ar—H); 3.37 (1H, s, OH); 3.17 (2H, dd, J4.5, 13.5 Hz, H-3, H-5); 3.04 (2H, d, J 13.5 Hz, CH$_2$Ph); 2.96 (2H, d, J 13.5 Hz, CH$_2$Ph); 2.82 (2H, t, J 13.9 Hz, H-2, H-6); 2.57 (2H, dd, J 4.5, 13.5 Hz, H-2, H-6).

Example 25

4-(Benzothiazol-2-yl)-4-hydroxy-3,3-di(phenylthio)-cyclohexan-1-one (Q25)

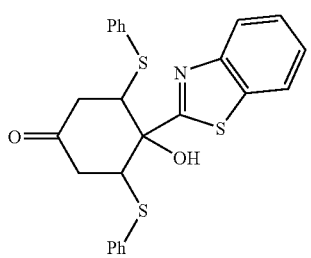

The title compound was synthesised according to Method H, described above. Yield 85%; mp 150–1° C.; $^1$H NMR (CDCl$_3$) δ 7.80 (1H, m, Ar—H); 7.61(1H, m, Ar—H); 7.41–7.31(2H, m, Ar—H); 7.13–7.08 (4H, m, Ar—H); 6.99–6.91 (6H, m, Ar—H); 4.37 (1H, s, OH); 4.10 (2H, dd, J 4.9, 13.4 Hz, H-3, H-5); 2.83 (2H, dd, J 4.83, 13.5 Hz, H-2, H-6); 2.00 (2H, t, J 14.1 Hz, H-2, H-6).

Example 26

3,5-[2-(N-Acetylamino)-2-(carboxymethyl)ethylthio]-4-hydroxy-4-phenylcylohexan-1-one (Q26)

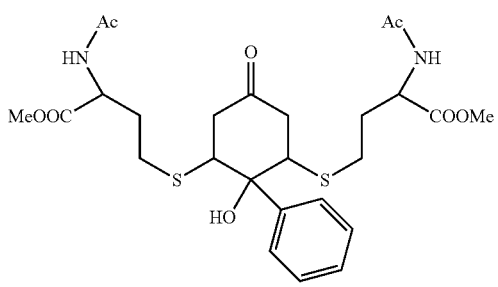

To 4-hydroxy-4-phenylcyclohexa-2,5-dien-1-one (0.1 g, 0.54 mmol) in ethanol (5 mL) was added N-acetylcysteine methyl ester (0.209 g, 1.18 mmol, 2.2 equivalents) and triethylamine (0.054 g, 0.54 mmol, 1.0 equivalents). After two hours the solvent was removed under vacuum and the residue stirred with diethylether (5 mL) to remove residual starting material. The gummy residue was collected, triturated with diethylether (2×5 mL). The product was collected as a white solid. The yield was 74%; mp 68–9° C.; $^1$H NMR (DMSO) δ 8.20 (1H, d, J 7.7 Hz, exch. D$_2$O, N—H); 8.12 (1H, d, J 7.5 Hz, exch D$_2$O, N—H); 7.55 (2H, m, Ar—H); 7.29 (3H, m, Ar—H); 5.53 (1H, s, exch. D$_2$O, OH); 4.20 (2H, m, H-α); 3.65 (2H, m, H-3, H-5); 3.59 (3H, s, OCH$_3$); 3.56 (3H, s, OCH$_3$); 2.73 (2H, m, H-2, H-6); 2.53–2.34 (4H, m, SCH$_2$); 2.19 (2H, m, H-2, H-6); 1.82 (3H, s, NHCOCH$_3$); 1.77 (3H, s, NHCOCH$_3$).

Example 27

4-(Benzothiazol-2-yl)-4-hydroxy-3-phenylthio-5-cyclohexen-1-one (Q27)

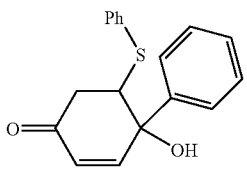

The title compound was synthesised according to Method I, described above. Yield 72%; mp 66° C.; $^1$H NMR (CDCl$_3$) δ 7.89 (2H, m, Ar—H); 7.52–7.38 (2H, m, Ar—H); 7.31–7.27 (2H, m, Ar—H); 7.07 (3H, m, Ar—H); 6.87 (1H, d, J 10.0 Hz, H-5); 6.23 (1H, d, J 10.0 Hz, H-6); 4.56 (1H, s, OH); 4.34 (1H, dd, J 4.5, 10.1 Hz, H-3); 3.20 (1H, dd, J 4.5, 16.7 Hz, H-2); 3.01 (1H, dd, J 10.1, 16.7 Hz, H-2).

Example 28

4-Benzothiazol-2-yl-5-S-glutathionyl-4-hydroxy-cyclohex-2-enone (Q28)

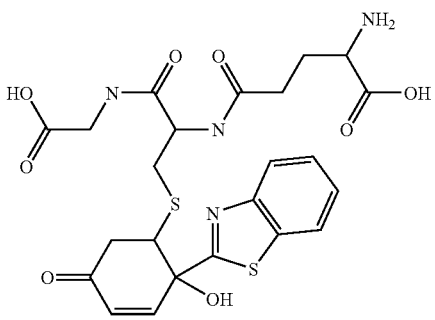

To a solution of 4-benzothiazol-2-yl-4-hydroxycyclo-hexa-2,5-dienone (0.1 g, 0.41 mmol) in ethanol (2 mL) was added glutathione (0.126 g, 0.41 mmol, 1 eq.) in water (2 mL). After mixing, the reaction mixture was left to stand for 6 days. TLC (cellulose, eluted with the upper phase of an n-butanol:water:acetic acid 5:4:1 mixture) suggested adduct formation (product R$_F$ 0.5). The product was purified by column chromatography (Sephadex LH-20) eluted with water. Fractions were collected in batches of 10×10 mL, freeze dried and analysed by NMR spectroscopy. Fractions 1–10 yielded the 'mono' adduct as a white powder (0.040 g).

$^1$H-NMR (D$_2$O) δ 7.64 (2H, m, Ar—H); 7.17 (2H, m, Ar—H); 6.82 (1H, dd, J=10.0, 1.5 Hz, cyclohex H-3); 6.72 (1H, dd, J=10.0, 4.0 Hz, cyclohex H-3); 6.04 (1H, d, J=9.8 Hz, cyclohex H-2); 5.92 (1H, dd, J=10.0, 1.6 Hz, cyclohex H-2); 4.61 (1H, m, cyst □-H); 3.84 (1H, m, cyclohex H-5); 3.58 (3H, m, gly □-H, glu □-H); 3.30–2.50 (4H, m, cyst CH$_2$, cyclohex H-6×2); 2.19 (2H, m, glu GH$_2$CONH—); 1.88 (2H, m, CH$_2$CH$_2$CONH—).

Example 29

N-[4-methoxy-4-(benzothiazol-2-yl)cyclohexa-2,5-dienylidene]-4-methylbenzenesulphonamide (Q29)

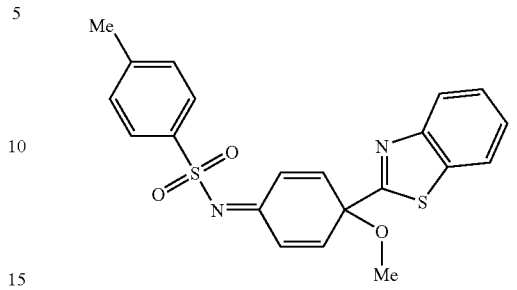

The title compound was synthesised according to Method J, described above.

To 2-(4-aminophenyl)-benzothiazole (0.5 g, 2.2 mmol) in pyridine (6 mL) was added para-toluenesulphonyl chloride (0.506 g, 2.7 mmol, 1.5 equiv.) in pyridine (4 mL). The reaction mixture was heated at reflux for 10 mins, then cooled and water (10 mL) added. The white precipitate formed was collected on a filter, washed with water and dried under vacuum to give N-[(4-benzothiazol-2-yl)phenyl]-4-methylbenzenesulfonamide as a white solid. The yield was 0.807 g (96%).

To the the sulfonamide (0.1 g) dissolved in methanol (2 mL) was added BTIB (1.1 eq.) in one portion as a solid. The resulting suspension was stirred at room temperature for 5 hours. The precipitate formed was collected on a filter, washed with ice cold methanol (2 mL) and dried under vacuum to give the title compound.

Yield 73%; $^1$H NMR (d$_6$-DMSO) δ 8.18 (1H, m, benzothiazole-H); 8.03 (1H, m, benzothiazole-H); 7.88 (1H, d, J=8.3 Hz, benzenesulphonamide H-2, H-6); 7.65 (1H, dd, J=10.3, 2.1 Hz, cyclohex-H); 7.55–7.48 (5H, m, benzothiazole-H×2, benzenesulphonamide H-3, H-5); 7.24 (1H, dd, J=10.2, 2.8 Hz, cyclohex-H); 7.12 (1H, dd, J=10.0, 2.8 Hz, cyclohex-H); 6.67 (1H, dd, J=9.8, 2.0 Hz, cyclohex-H); 3.41 (3H, s, OCH$_3$); 2.45 (3H, s, CH$_3$).

Example 30

N-[4-methoxy-4-(6-methylbenzothiazol-2-yl)cyclohexa-2,5-dienylidene]4-methylbenzenesulphonamide (Q30)

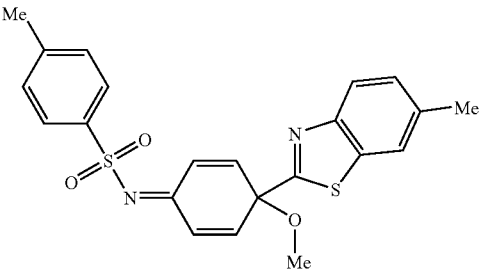

The title compound was synthesised according to Method J, described above.

To 2-(4-aminophenyl)-6-methylbenzothiazole (5 g, 20.8 mmol) in pyridine (60 mL) was added para-toluenesulphonyl chloride (5.953 g, 31.2 mmol, 1.5 eq.) in pyridine (40 mL). The reaction mixture was heated at reflux for 10 mins, then cooled and water (100 mL) added. The white precipitate formed was collected on a filter, washed with water and dried under vacuum to give N-[4-(6-methylbenzothiazol-2-yl)phenyl]-4-methylbenzenesulfonamide as a white solid. The yield was 8.091 g (99%).

To the sulfonamide (0.1 g) dissolved in methanol (2 mL) was added BTIB (1.1 eq.) in one portion as a solid. The resulting suspension was stirred at room temperature for 5 hours. The precipitate formed was collected on a filter, washed with ice cold methanol (2 mL) and dried under vacuum to give the title compound.

Yield 67%; mp 166–168° C.; $^1$H NMR (CDCl$_3$) δ 7.90 (4H, m, cyclohexadienylidene H-2, cyclohexadienylidene H-6, benzene H-2, benzene H-6), 7.37 (3H, m, benzothiazole H-7, benzene H-3, benzene H-5), 7.10 (1H, dd, J 2.5, 9.0 Hz, benzothiazole H05), 6.90 (2H, m, cyclohexadienylidene H-3, cyclohexadienylidene H-5), 6.63 (1H, m, benzothiazole H-4), 3.90 (3H, s, OCH$_3$), 3.45 (3H, s, OCH$_3$), 2.48 (3H, s, CH$_3$).

Example 31

N-[4-methoxy-4-(6-methoxybenzothiazol-2-yl)cyclohexa-2,5-dienylidene]-4-methylbenzenesulphonamide (Q31)

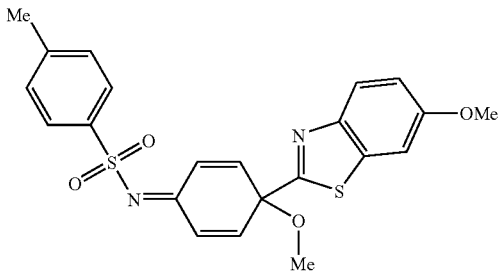

The title compound was synthesised according to Method J, described above, using 2-(4-aminophenyl)-6-methoxybenzothiazole. Yield 67%; mp 166–168° C.; $^1$H NMR (CDCl$_3$) δ 7.90 (4H, m, H-2, H-6, toluenesulphonyl H-2, H-6), 7.37 (3H, m, H-7', toluenesulphonyl H-3, H-5), 7.10 (1H, dd, J2.5, 9.0 Hz, H-5'), 6.90 (2H, m, H-3, H-5), 6.63 (1H, m, H-4'), 3.90 (3H, s, OCH$_3$), 2.48 (3H, s, CH$_3$); IR 1651, 1605, 1545, 1464, 1316, 1158, 860, 677 cm$^{-1}$; MS (Cl) m/z 441 (M$^+$+1), 409 (M$^+$—OCH$_3$); Anal. (C$_{21}$H$_{18}$N$_2$O$_3$S$_2$.½H$_2$O) (C$_{22}$H$_{20}$N$_2$O$_4$S$_2$) C, H, N.

Example 32

N-[4-methoxy-4-(6-fluorobenzothiazol-2-yl)cyclohexa-2,5-dienylidene]-4-methylbenzenesulphonamide (Q32)

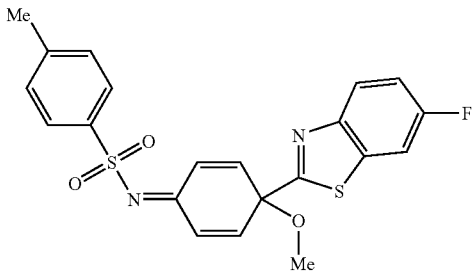

The title compound was synthesised according to Method J, described above, using 2-(4-aminophenyl)-6-fluorobenzothiazole. Yield 78%; mp 135° C.; $^1$H NMR (CDCl$_3$) δ 7.98 (4H, m), 7.61 (1H, dd, J 2.1, 8.0 Hz), 7.39 (2H, d, J 7.9 Hz), 7.25 (1H, m), 6.87 (2H, m), 6.64 (1H, m), 3.46 (3H, s, OCH$_3$), 2.48 (3H, s, CH$_3$); IR 1651, 1609, 1544, 1454, 1317, 1152, 858, 675 cm$^{-1}$; MS (Cl) m/z 429 (M$^+$+1), 397 (M$^+$—OCH$_3$); Anal. (C$_{21}$H17FN$_2$O$_3$S$_2$) C, H, N.

Example 33

N-[4-methoxy-4-(4-fluorobenzothiazol-2-yl)cyclohexa-2,5-dienylidene]-4-methylbenzenesulphonamide (Q33)

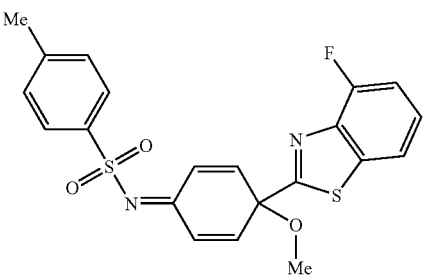

The title compound was synthesised according to Method J, described above, using 2-(4-aminophenyl)-4-fluorobenzothiazole. Yield 78%; mp 176° C.; $^1$H NMR (CDCl$_3$) δ 8.04 (3H, d, J 7.7 Hz, benzothiazole-H, toluenesulphonyl H-2, H-6), 7.82 (1H, d, J 7.6 Hz, benzothiazole-H), 7.50 (2H, d, J 7.7 Hz, toluenesulphonyl H-3, H-5), 7.35 (2H, m), 7.00 (2H, t, J 8.8 Hz), 6.78 (1H, d, J 9.9 Hz), 3.58 (3H, s, OCH$_3$), 2.60 (3H, s, CH$_3$); IR 1655, 1609, 1543, 1468, 1316, 1154, 862, 675 cm$^{-1}$; MS (Cl) m/z 429 (M$^+$+1), 397 (M$^+$—OCH$_3$); Anal. (C$_{21}$H$_{17}$FN$_2$O$_3$S$_2$.H$_2$O) C, H, N.

Example 34

4-(para-nitrobenzoyloxy)-4-(benzothiazol-2-yl)-2,5-cyclohexadien-1-one (Q34)

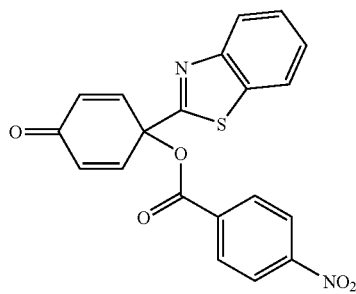

The title compound was synthesised according to Method F, described above, using para-nitrophenylacyl chloride. mp 138° C.; NMR $^1$H (DMSO) δ 8.46 (2H, d, J 10.0 Hz, benzoyl H-3,5), 8.33 (2H, d, J 10.0 Hz, benzoyl H-2,6), 8.31 (1H, m, benzothiazole-H), 8.17 (1H, m, benzothiazole-H), 7.58 (2H, m, benzothiazole-H), 7.56 (2H, d, J 12.5 Hz, H-3,5), 6.56 (2H, d, J 12.5 Hz, H-2,6); IR (Kbr disc) 1734, 1670, 1526, 1348, 1265, 1161, 939, 718 cm$^{-1}$; Mass Spectrum (AP) 393 (M$^+$+1); Elemental Analysis C$_{20}$H$_{12}$N$_2$O$_5$S.½H$_2$O Requires C 59.85, H 3.26, N 6.99; found C 59.59, H 3.08, N 7.12%.

Example 35

4-(para-methoxybenzoyloxy)-4-(benzothiazol-2-yl)-2,5-cyclohexadien-1-one (Q35)

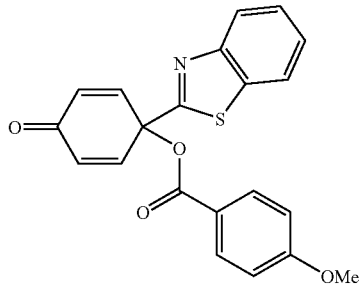

The title compound was synthesised according to Method F, described above, using para-methoxyphenylacyl chloride. mp 137° C.; IR 1732, 1688, 1672, 1603, 1429, 1260, 1165, 764 cm$^{-1}$; Mass Spectrum (AP) 378 (M$^+$+1); Elemental Analysis $C_{21}H_{15}NO_4S \cdot H_2O$ Requires C 63.79, H 4.33, N 3.54; found C 64.07, H 4.37, N 3.28%.

Example 36

4-Hydroxy-4-(6-methoxybenzothiazol-2-yl)-2,5-cyclohexadien-1-one) (Q36)

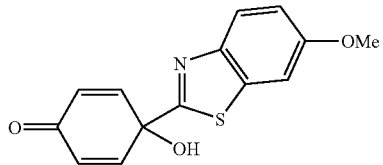

The title compound was synthesised according to Method K, described above.

Example 37

4-Hydroxy-4-(6-fluorobenzothiazol-2-yl)-2,5-cyclohexadien-1-one) (Q37)

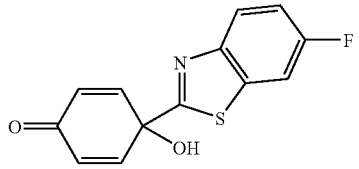

The title compound was synthesised according to Method K, described above.

Example 38

4-Hydroxy-4-(6-chlorobenzothiazol-2-yl)-2,5-cyclohexadien-1-one) (Q38)

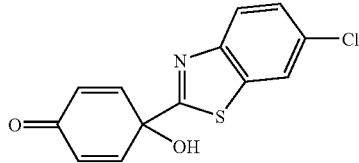

The title compound was synthesised according to Method K, described above.

Example 39

4-Hydroxy-4-(6-bromobenzothiazol-2-yl)-2,5-cyclohexadien-1-one) (Q39)

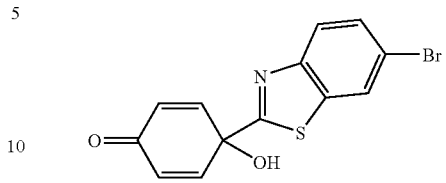

The title compound was synthesised according to Method K, described above.

Example 40

4-Hydroxy-4-(6-mesylbenzothiazol-2-yl)-2,5-cyclohexadien-1-one) (Q40)

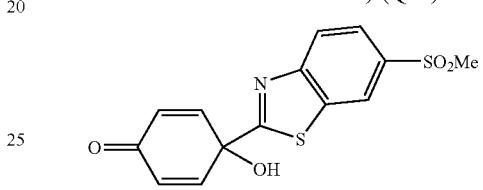

The title compound was synthesised according to Method K, described above.

Example 41

4-Hydroxy-4-(5-trifluoromethylbenzothiazol-2-yl)-2,5-cyclohexadien-1-one) (Q41)

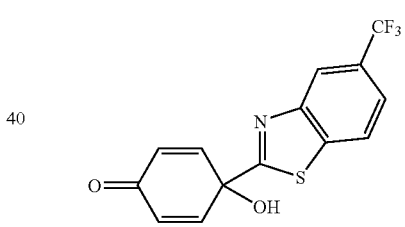

The title compound was synthesised according to Method K, described above.

Example 42

4-Hydroxy-4-(5-fluorobenzothiazol-2-yl)-2,5-cyclohexadien-1-one) (Q42)

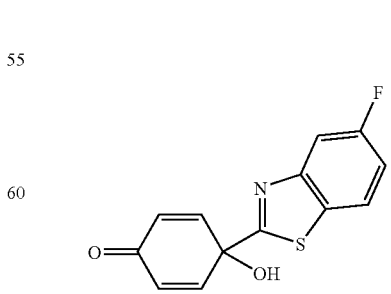

The title compound was synthesised according to Method K, described above.

Example 43

4-(Benzothiazol-2-yl)-4-hydroxycyclohexanone (Q43)

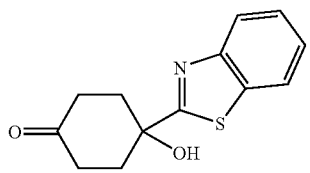

The title compound was synthesised according to Method L, described above.

To benzothiazole (3.46 g, 25.6 mmol) dissolved in dry THF under a nitrogen atmosphere at −78° C. was added butyl lithium (17.1 mL of 1.5M solution, 1 equiv.) dropwise. The reaction mixture was stirred for 1 h then 1,4-cyclohexanedione mono-ethylene ketal dissolved in dry THF (15 mL) in one portion. The reaction mixture was stirred at −78° C. for a further 3 h then water (10 mL) was added. The mixture was warmed to room temperature and the white precipitate was collected on a filter, washed with water (2×20 mL) then dried under vacuum to give 4-(benzothiazol-2-yl)-1,1-ethylenedioxy-4-hydroxycyclohexane. The yield was 4.403 g (59%); mp 165° C.; $^1$H NMR (CDCl$_3$) δ 8.05 (1H, m, benzothiazole H-4/7), 7.89 (1H, m, benzothiazole H-4/7), 7.47 (1H, m, benzothiazole H-5/6), 7.39 (1H, m, benzothiazole H-5/6), 4.02 (4H, s, ethylene 2×CH$_2$), 3.16 (1H, s, OH), 2.41–2.31 (4H, m, cyclohexanone 2×CH$_2$), 1.82–1.72 (4H, m, cyclohexanone 2×CH$_2$); IR (KBr disc) 2897, 1501, 1437, 1368, 1038, 997, 764 cm$^{-1}$; MS (AP+) 292 (M$^+$+1), 274 (M$^+$+1-H$_2$O); Anal. (C$_{15}$H$_{17}$NO$_3$) C, H, N.

A solution of 4-(benzothiazol-2-yl)-1,1-ethylenedioxy-4-hydroxycyclohexane (1.0 g, 3.4 mmol) in acetic acid (40 mL) and conc. HCl (10 mL) was heated at 80° C. for 2 h with stirring. The volume was reduced on a rotary evaporator and the remaining solution was carefully neutralized with saturated sodium hydrogen carbonate solution and then extracted with diethyl ether (3×50 mL). The organic layers were combined, washed with water (2×50 mL) and dried over magnesium sulphate. Removal of the solvent under vacuum gave the product 4-(benzothiazol-2-yl)-4-hydroxycyclohexan-1-one (0.618 g) as an off white solid (73%); mp 134° C.; $^1$H NMR (CDCl$_3$) δ 8.00 (1H, m, benzothiazole H-4/7), 7.91 (1H, m, benzothiazole H-4/7), 7.49 (1H, m, benzothiazole H-5/6), 7.41 (1H, m, benzothiazole H-5/6), 3.66 (1H, s, OH), 2.97–2.85 (4H, m, cyclohexanone CH$_2$), 2.53–2.34 (4H, m, cyclohexanone CH$_2$); IR (KBr disc) 2913, 1690, 1505, 1427, 1312, 1198, 889, 768 cm$^{-1}$; MS (AP+) 248 (M$^+$+1), 230 (M$^+$+1−H$_2$O); Anal. (C$_{13}$H$_{13}$NO$_2$S) C, H, N.

Example 44

4-(benzothiazol-2-yl)-4-hydroxy-2,6-dimethylcyclohexa-2,5-dien-1-one (Q44)

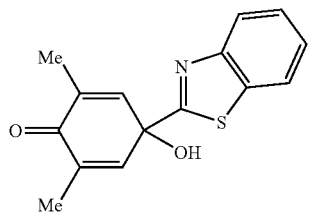

To 2,6dimethyl-1,4-benzoquinone (2 g, 14.7 mmol) and trimethylsilyl cyanide (1.45 g, 14.7 mmol) dissolved in dry dichloromethane under a nitrogen atmosphere was added triphenylphosphine (5 mg). The reaction mixture was heated at reflux for 1 h then cooled to room temperature. The solvent was removed under vacuum and the residue treated with hexane. The crystalline solid was collected on a filter washed with a little cold hexane and dried under vacuum. The yield was 3.35 g (97%). The product 4-cyano-2,6-dimethyl-4-trimethylsilyloxycyclohexa-2,5-dien-2-one (0.862 g, 6.4 mmol) was used without further purification in the next step, according to Method B, to yield the title compound as an off-white solid (0.919 g, 3.4 mmol) in 53% yield; mp 132° C.; $^1$H NMR (CDCl$_3$) δ 8.07 (1H, m, benzothiazole H-4/7), 7.92 (1H, m, benzothiazole H4/7), 7.57 (1H, m, benzothiazole H-5/6), 7.50 (1H, m, benzothiazole H-5/6), 6.81 (2H, s, H-3, H-5), 4.28 (1H, s, OH), 2.02 (6H, s, CH$_3$×2), IR (KBr disc) 2359, 1669, 1632, 1507, 1433, 1373, 1057, 768 cm$^{-1}$; MS (AP+) 272 (M++1), 254 (M$^+$+1—H$_2$O); Anal. (C$_{15}$H$_{13}$NO$_2$S) C, H, N.

Example 45

4-(benzothiazol-2-yl)-2,6-bis(phenylmethinyl)-4-hydroxycyclohexanone (Q45)

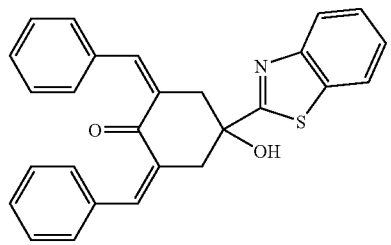

A solution of 4-(benzothiazol-2-yl)-4-hydroxycyclohexan-1-one (0.124 g, 0.5 mmol) and benzaldehyde (0.212 g, 2.0 mmol) dissolved in DMSO (1 mL) and 1M sodium hydroxide solution (5 mL) was heated at reflux for 3 h. The reaction mixture was cooled, diluted with ethanol (25 mL) and 1M HCl solution (5 mL) was added. Concentration under vacuum to a volume of 10 mL gave a white precipitate which was collected on a filter and washed with water. The solid was purified by flash column chromatography eluting with ethyl acetate/hexane 2/8. The product was a yellow solid 0.120 g (58%); mp 184° C.; $^1$H NMR (CDCl$_3$) δ 8.07 (2H, s, methylene C—H×2), 8.04 (1H, m, benzothiazole H-4/7), 7.91 (1H, m, benzothiazole H-4/7), 7.54–7.36 (12H, m, benzothiazole H-5,6, Ph-H×10), 3.72 (2H, dd, J 2.6, 15.9 Hz, H-3,5), 3.51 (2H, dd, J 7.3, 14.5 Hz), 3.05 (1H, s, OH); IR (KBr disc) 1672, 1599, 1447, 1242, 1193, 1179, 986, 768 cm$^{-1}$; MS (AP+) 424 (M$^+$+1), 406 (M$^+$+1—H$_2$O); Anal. (C$_{27}$H$_{21}$NO$_2$S.½H$_2$O) C, H, N.

Example 46

4-Benzothiophen-2-yl-4-hydroxy-4H-naphth-1-one (Q46)

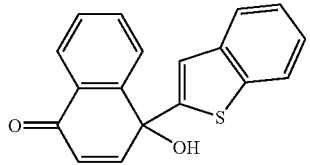

The title compound was synthesised according to Method M, described above. Yield 52%; mp 150–152° C.; $^1$H NMR (CDCl$_3$) δ 8.20 (1H, d, J 7.5 Hz, ArH), 7.92–7.81 (2H, m, ArH), 7.72–7.65 (2H, m, ArH), 7.49 (1H, d, J 4.0 Hz, ArH), 7.40 (1H, td, J 1.5, 7.5 Hz, ArH), 7.38–7.33 (2H, m, ArH), 7.30 (1H, d, J 10.1 Hz, H-3), 7.09 (1H, s), 6.65 (1H, s, H-3'), 6.45 (1H, d, J 10.1 Hz, H-2); $^{13}$C NMR (CDCl$_3$) δ 185.1, 151.9, 149.9 146.9, 140.1, 139.9, 133.6, 129.7, 128.9, 128.6, 126.4, 126.3, 124.7, 124.6, 123.9, 122.6, 121.2, 70.7; IR 3430, 1648, 1597, 1434, 1276, 1155, 1036, 760 cm$^{-1}$; MS (CI) m/z 293 (M$^+$+1); Anal. (C$_{18}$H$_{12}$O$_2$S) C, H.

Example 47

4-(Benzofuran-2-yl)-4-hydroxy-4H-naphth-1-one (Q47)

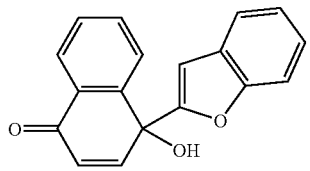

The title compound was synthesised according to Method M, described above. Yield 65%; mp 105–107° C.; $^1$H NMR (CDCl$_3$) δ8.14 (1H, d, J 7.2 Hz, ArH), 7.80 (1H, d, J 5.3 Hz, ArH), 7.65 (1H, t, J 7.5 Hz, ArH), 7.55–7.49 (2H, m, ArH), 7.40 (1H, d, J 7.5 Hz, ArH), 7.28–7.12 (3H, m, ArH), 6.58 (1H, s, H-3'), 6.40 (1H, d, J 10.2 Hz, H-2); $^{13}$C NMR (CDCl$_3$) δ 157.0, 155.0, 148.5. 143.3, 133.8, 131.0, 130.4, 128.6, 128.5, 128.0, 127.0, 125.2, 123.6, 121.8, 111.9, 104.7, 69.4; IR 3311, 1657, 1624, 1451, 1240, 1170, 1038, 765 cm$^{-1}$; MS (CI) m/z 277.1 (M$^+$+1), 259; Anal. (C$_{18}$H$_{12}$O$_3$) C, H.

Biological Data

Compounds were assessed for their activity using various in vitro and in vivo assays, described below.

NCI Screening

Compounds were tested for in vitro activity (48 h drug exposure) across 60 human cancer cell lines through the National Cancer Institute (NCI) Developmental Therapies Screening Program (Boyd et al., 1995). The mean growth inhibition (GI50) and cytotoxicity lethal concentration (LC50) values are summarized in Table 1. Surprisingly and unexpectedly, many of the compounds had particular activity in colon and renal sub-panels.

TABLE 1

Activity of Compounds In NCI in Vitro 60 Cell Panel

| Cmpd | mean GI$_{50}$ (μM)[a] | mean LC$_{50}$ (μM)[a] | mean LC$_{50}$ in colon sub-panel (μM)[b] | mean LC$_{50}$ in renal sub-panel (μM)[c] | HCT 116[d] | ACHN[f] |
|---|---|---|---|---|---|---|
| Q01 | 0.52 | 7.24 | 3.66 | 2.40 | 0.60 | 1.00 |
| Q02 | 0.25 | 5.75 | 1.69 | 1.40 | 0.60 | 0.33 |
| Q03 | 1.41 | | | | | |
| Q04 | 0.46 | 7.08 | 1.13 | 1.64 | 0.87 | 4.90 |
| Q05 | 0.23 | 3.39 | 1.76 | 1.57 | 0.43 | 0.69 |
| Q06 | 0.46 | 6.31 | 2.31 | 1.80 | 0.68 | 0.58 |
| Q07 | 1.10 | | | | | |
| Q08 | 0.81 | 11.7 | 6.58 | 4.68 | 4.47 | 7.76 |
| Q09 | 1.82 | 25.7 | 12.2 | 17.0 | 5.37 | 13.2 |
| Q10 | 1.07 | 15.8 | 10.2 | 9.66 | 4.26 | 15.1 |
| Q11 | 2.29 | 21.9 | 10.6 | 16.7 | 6.31 | 5.50 |
| Q12 | 1.91 | 20.4 | 6.9 | 11.35 | 5.24 | 8.91 |
| Q13 | 1.78 | 30.9 | 32.5 | 14.4 | 5.89 | 35.5 |
| Q14 | 1.35 | 14.5 | 6.19 | 9.17 | 4.90 | 7.94 |
| Q15 | 0.36 | 6.76 | 1.98 | 1.27 | 0.52 | 0.53 |
| Q16 | 25.4 | | | | | |
| Q17 | 1.91 | 33.1 | 8.81 | 22.4 | 9.55 | 24.5 |
| Q19 | 0.71 | 11.7 | 7.47 | 9.55 | 4.57 | 3.23 |
| Q21 | 4.79 | | | | | |
| Q22 | 12.6 | | | | | |
| Q23 | 1.82 | | | | | |
| Q24 | 3.98 | | | | | |
| Q25 | 0.59 | | | | | |
| Q28 | 2.19 | | | | | |
| Q29 | 15.5 | 83.2 | >100 | >100 | 44.7 | >100 |
| Q30 | 1.20 | 19.5 | 9.92 | 10.6 | 1.78 | 6.92 |
| Q31 | 1.91 | 18.6 | 13.2 | 11.2 | 5.01 | 8.32 |
| Q32 | 1.74 | 30.2 | 25.6 | 19.1 | 5.25 | >100 |
| Q33 | 2.57 | 27.5 | 26.9 | 14.4 | 57.5 | 7.59 |
| Q43 | >100 | >100 | >100 | >100 | >100 | >100 |
| Q44 | 38.2 | >100 | >100 | >100 | >100 | >100 |
| Q45 | 2.69 | 47.9 | 17.4 | 37.2 | 5.37 | 30.9 |
| Q46 | 2.29 | 70.8 | >100 | >100 | >100 | >100 |
| Q47 | 0.74 | 7.76 | 7.76 | 6.48 | 4.90 | 5.75 |

[a]For definitions of mean GI$_{50}$ and mean LC$_{50}$ see Boyd et al., 1995, and Weinstein et al., 1997.
[b]Normally n = 6 and excluding the insensitive SW-620 colon cell line.
[c]Normally n = 8.
[d]The most sensitive colon cell line.
[f]The most sensitive renal cell line.

Growth Inhibitory Assay

Compounds were prepared as 10 mM top stocks, dissolved in DMSO, and stored at 4° C., protected from light, for a maximum period of 4 weeks. Human derived cell lines (HCT 116, HT29 colon carcinoma; MCF-7 (ER+), MDA 468 (ER−) breast carcinoma; A549 lung adenocarcinoma) were routinely cultivated at 37° C. in an atmosphere of 5% CO$_2$ in RPMI 1640 medium supplemented with 2 mM L-glutamine and 10% fetal calf serum and subcultured twice weekly to maintain continuous logarithmic growth. Cells were seeded into 96-well microtiter plates at a density of 5×10$^3$ per well and allowed 24 hr to adhere before drugs were introduced (final concentration 0.1 nM–100 μM, n=8). Serial drug dilutions were prepared in medium immediately prior to each assay. At the time of drug addition and following 72 hr exposure, MTT was added to each well (final concentration 400 g/mL). Incubation at 37° C. for 4 hr allowed reduction of MTT by mitochondrial dehydrogenase to an insoluble formazan product. Well contents were aspirated and formazan solubilized by addition of DMSO:glycine buffer (pH 10.5) (4:1). Absorbance was measured using an Anthos Labtec systems plate reader at 550 nm, and used as a measure of cell viability; thus cell growth or drug toxicity was determined. The results are summarised in Table 2.

TABLE 2

In Vitro Activity

IC50 (µM)

| Cmpd. No. | Colon | | Breast | | Lung |
|---|---|---|---|---|---|
|  | HCT 116 | HT 29 | MCF-7 | MDA 468 | A549 |
| Q01 | 0.159 | 0.419 | — | — | 2.30 |
| Q02 | 0.169 | 0.552 | — | — | 2.43 |
| Q03 | 2.84 | 1.76 | — | — | 6.13 |
| Q04 | 0.18 | 0.29 | 0.39 | 0.35 | 2.33 |
| Q05 | 0.04 | 0.38 | 0.35 | 0.79 | 2.35 |
| Q06 | 14.92 | 26.32 | — | — | — |
| Q07 | 0.21 | 0.504 | 0.509 | 0.353 | — |
| Q08 | 0.82 | 2.5 | 1.3 | 1.4 | — |
| Q09 | 0.42 | 1.36 | 0.78 | 1.77 | — |
| Q10 | 0.72 | 0.97 | 0.77 | 1.7 | — |
| Q11 | 2.22 | 3.63 | — | — | — |
| Q12 | 0.547 | 0.46 | 0.72 | 1.5 | — |
| Q13 | 0.663 | 1.25 | 0.569 | 0.719 | — |
| Q14 | 0.618 | 0.719 | — | — | — |
| Q15 | 0.24 | 0.52 | 0.23 | 0.09 | — |
| Q17 | 0.60 | 2.6 | 0.56 | 0.51 | — |
| Q18 | 0.89 | 1.98 | 0.51 | 0.74 | — |
| Q19 | 0.27 | 1.10 | 0.31 | 0.19 | — |
| Q20 | 0.53 | 1.81 | 0.28 | 0.77 | — |

In Vitro Propidium Iodide Cytotoxicity Assay

This assay was performed essentially according to the method described by Dengler et al., 1995. Human tumor cells (see Table 2) were plated in 96 well flat-bottomed microtiter plates (50 µL cell suspension, $1 \times 10^5$ or $5 \times 10^4$ cells/mL) and additional 50 µL of culture medium were added. After a 24 hr recovery, 50 µL of culture medium containing 50 µg/mL gentamycin was added into the 6 control wells or medium containing the test drug (Q05) was added to the wells. Each drug concentration was plated in triplicate. Following 3–6 days of incubation, depending on cell doubling time, a modified propidium iodide (PI) assay was performed. Culture medium was replaced by fresh medium and 50 µL of an aqueous propidium iodide solution (25 µg/mL) were added to each well. PI does not cross intact cell membranes and enters only the nucleus of dead cells by intercalation into DNA and RNA. The fluorescence signal correlates with the numbers of dead cells. Fluorescence ($FU_1$) was measured using a Millipore Cytofluor 2350 microplate reader (excitation 530 nm, emission 620 nm). Microplates were then kept at −18° C. for 24 hr, yielding a total cell kill. After thawing of the plates and a second fluorescence measurement ($FU_2$), the amount of viable cells was calculated by subtraction of $FU_2$ from $FU_1$). Growth inhibition was expressed as treated/control ×100 (% T/C) (that is, growth inhibition at a given concentration is represented as a percentage of treated cell growth over control cell growth). Inhibiting concentrations (IC) were determined by plotting compound concentration versus cell viability. Mean $IC_{50}$, $IC_{70}$, and $IC_{90}$ values were calculated for each individual cell line. The results are summarised in Table 3.

TABLE 3

Activity In Vitro, Q05

Mean IC (µg/mL ± S.D.)

| Cell Line | IC50 | IC70 | IC90 |
|---|---|---|---|
| RXF 944L | 0.265 ± 0.06 | 0.48 ± 0.08 | 0.87 ± 0.09 |
| RXF 393NL | 0.34 ± 0.03 | 0.67 ± 0.09 | 8.63 ± 5.4 |
| RXF 631L | 0.37 ± N.E. | 0.56 ± N.E. | 0.84 ± N.E. |

FIG. 1 is a graph of % of control (fluorescence units) (one representative of three independent experiments) versus drug concentration (µg/mL) for the compound under study, Q05, and shows dose response curves for three renal carcinoma cell lines, hypernephroma RXF 944L (♦) followed by RXF 631L (▲) and RXF 393NL (■).

The most sensitive cell line was RXF 944L, followed by RXF 631 L and RXF 393NL. This activity is reflected in the in vivo data (Table 3) which show that RXF 944 in vitro sensitivity did translate into in vivo efficacy against the xenograft.

In Vivo Antitumor Activity

In vivo antitumor activity of the following compound (Q05) was examined.

Animals. Six to eight weeks old outbred nude mice of NMRI genetic background were used for all experiments. The animals were bred and raised in animal facilities in Freiburg, Germany and housed in Macrolon™ cages. The mice were kept under laminar air flow on natural day light cycles. Diet (Altromin, Lage, Germany) and water were provided ad libitum and room temperature (25+/−2° C.) as well as humidity (60+/−10%) were maintained. The experiments were conducted essentially according to the UKC-CCR guidelines under a project license approved by the German Federal Government (Regierungspräsidium Freiburg). The gender of the mice was chosen according to the gender of the patients from which the tumors were originally derived.

Tumors and Data Evaluation. For the experiments, three subcutaneously (s.c.) growing renal human tumor xenograft models from the Freiburg tumor panel were selected (RXF 944LX, RXF 393, and RXF 1220). All renal cell carcinomas were hypernephromas. For the experiments, the latter were engrafted from tumors in serial passage growing s.c. in nude mice. Fragments of approximately 25 mg were implanted s.c. in both flanks of the animals. When the tumors were clearly palpable and had reached a volume of 100–200 mm³, animals (6–12 tumors) were randomly allocated into treatment groups. Tumor growth was followed twice weekly by serial caliper measurement. Tumor volumes were calculated using the formula length×width²/2, where length (a) is the largest dimension and width (b) the smallest dimension perpendicular to the length (a×b²/2) (see, e.g., Geran et al., 1972).

Data evaluation was performed using software by plotting relative tumor volume against time. Relative tumor volumes were calculated for each single tumor by dividing the tumor volume on day X by the tumor volume on day 0 at the time of randomization. Tumor doubling time of test and control groups was defined as the period required to double the initial tumor volume (200%). Growth curves were analyzed in terms of maximal tumor inhibition (treated/control, T/C, calculated as median tumor weight of treated animals divided by median tumor weight of control animals times 100), growth delay (the difference in days to double the initial tumor volume of the test minus the control groups). Median relative tumor volumes of each treatment group were compared to those of the control group. Human tumors growing s.c. in nude mice were treated intraperitoneally (i.p.) with doses of 15 and 10 mg/kg drug either on days 1 and 2; on days 1 and 5; on days 1 and 8; or on days 1, 5 and 8. The data are summarised in Table 4.

The drug doses and treatment schedules used, were determined as being tolerated in non-tumor bearing nude mice prior to initiation of tumor experiments.

The RXF 393 and RXF 1220 renal tumor xenografts induce severe cachexia when tumors reach a certain size; thus, in these two models body weight loss occurring during treatment may be due to a combination of drug effect and tumor cachexia. It also appeared that in renal tumor bearing mice the drug was less well tolerated than intumour free mice.

TABLE 4

Activity of Q05 In Vivo

| Tumor Designation | Dose (1) (mg/kg) | Schedule (2) | T/C (3) | DT (4) | GD (5) | BWC (6) |
|---|---|---|---|---|---|---|
| RXF 944LX | Vehicle (7) | 1, 2 | 100 | 1.1 | — | +12 |
|  | 15 | 1, 2 | 27 | 4.1 | 2.9 | −14 |
| RXF 944LX | Vehicle | 1, 8 | 100 | 1.9 | — | +10 |
|  | 15 | 1, 8 | 43 | 4.2 | 2.3 | −3 |
| RXF 393 | Vehicle | 1, 5 | 100 | 2.1 | — | −17 |
|  | 15 | 1, 5 | 56 | 2.6 | 0.5 | −19 |
|  | 10 | 1, 5 | 63 | 3.0 | 0.9 | −16 |
| RXF 1220 | Vehicle | 1, 5, 8 | 100 | 3.1 | — | −5 |
|  | 15 | 1, 5, 8 | 66 | 5.3 | 2.2 | −20 |

(1) route: interperitoneally.
(2) see text.
(3) T/C = optimal test/control.
(4) DT = tumor doubling time.
(5) GD = growth delay.
(6) BWC = maximal body weight change.
(7) Vehicle = 10% DMSO/saline/0.05% Tween80.

Figure 2:
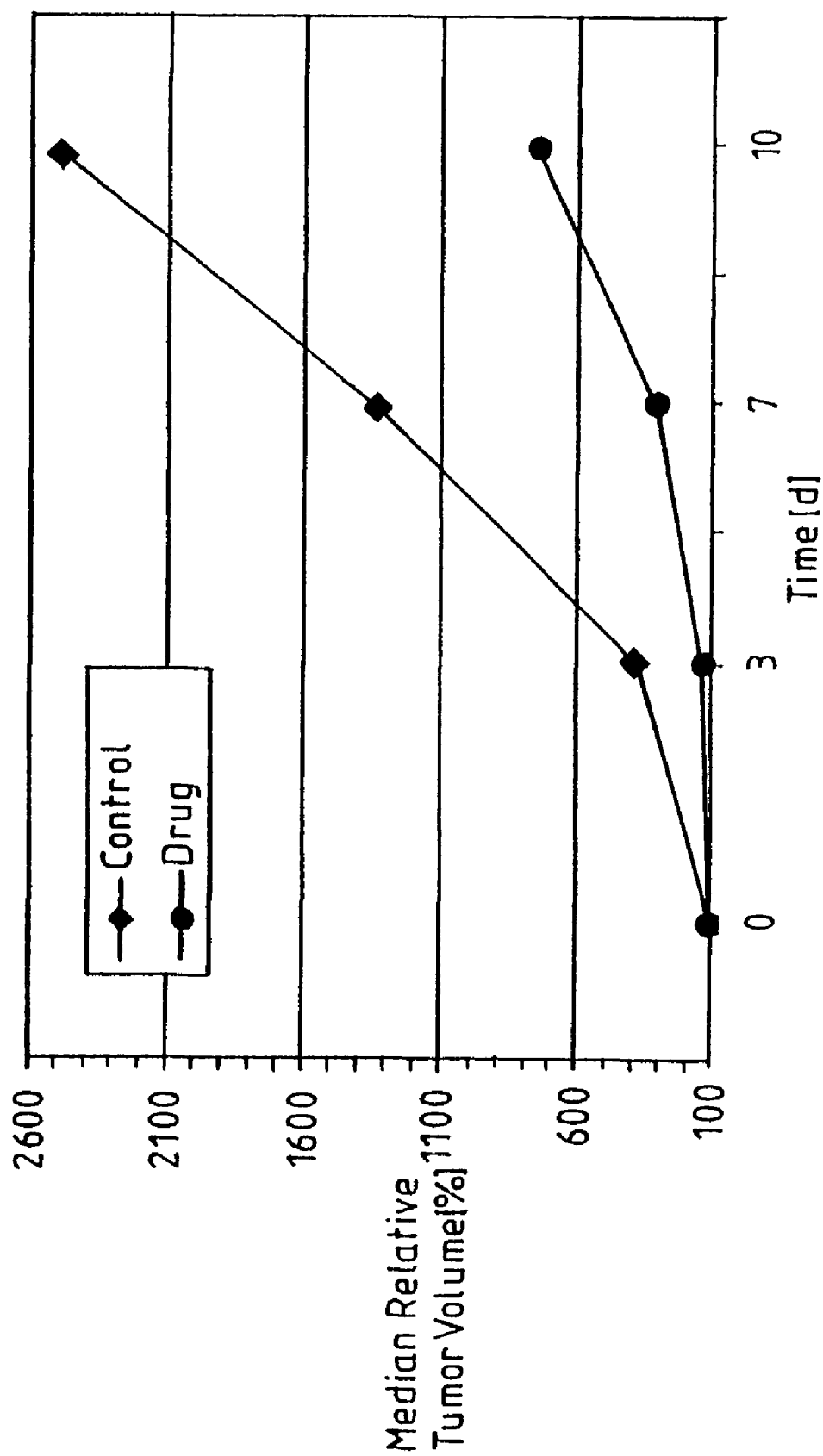
FIG. 2 is a graph of median relative tumor volume (%) versus time (days) for human renal tumor xenograft RXF 944LX, for control animals (♦) and animals treated with the compound under study, Q05 (■) (with T/C=43%). Six animals per group. 11–12 tumors per group. No deaths in control group. 1/6 toxic death in treatment group.

FIG. 2 is a graph of median relative tumor volume (%) versus time (days) for human renal tumor xenograft RXF 944LX, for control animals (♦) and animals treated with the compound under study, Q05 (■) (with T/C=43%). Six animals per group. 11–12 tumors per group. No deaths in control group. 1/6 toxic death in treatment group.

Figure 3:
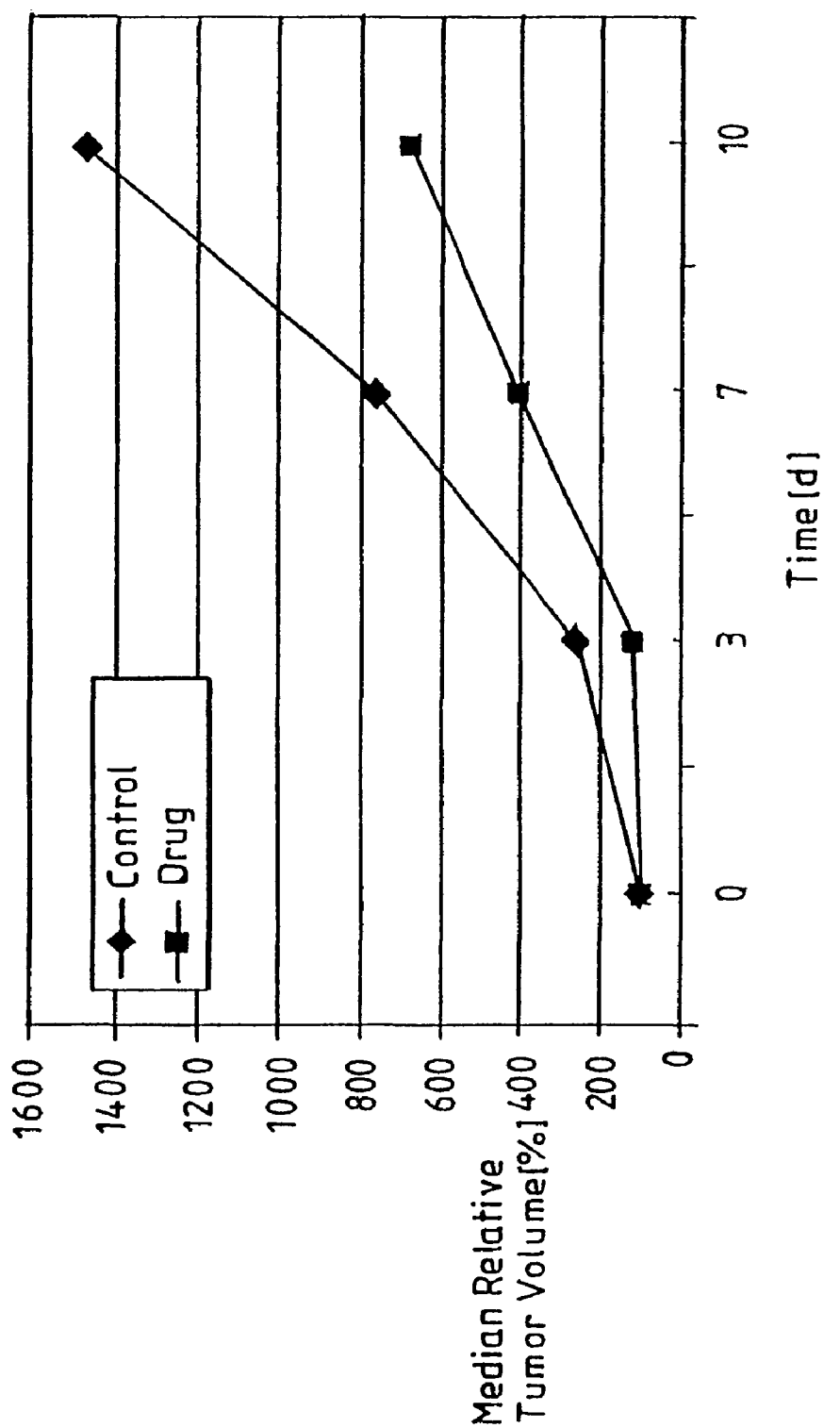
FIG. 3 is a graph of median relative tumor volume (%) versus time (days) for human renal tumor xenograft RXF 944LX, for control animals (♦)and animals treated with the compound under study, Q05 (■) (with T/C=27%). Three animals per group. 3 tumors per group.

FIG. 3 is a graph of median relative tumor volume (%) versus time (days) for human renal tumor xenograft RXF 944LX, for control animals (♦)and animals treated with the compound under study, Q05 (■) (with T/C=27%). Three animals per group. 3 per group.

Compounds of the present invention have also been shown to have in vivo activity against human colon cancer.

Thioredoxin Activity

Assays were performed using methods analogous to those described in Kirkpatrick et al., 1999 and Kunkel et al., 1997.

Thioredoxin (TR) (specific activity 43.6 μmol NADPH reduced/min/mg protein at 21° C.) was purified from human placenta as previously described (Oblong et al., 1993). Recombinant hTrx was expressed in *Escherichia coli* and purified as previously described (Gasdaska et al., 1994). The Trx and TR were stored at −20° C. with 5 mM dithiothreitol (DTT) which was removed before use with a desalting column (PDIO, Pharmacla, Uppsala, Sweden).

Microtiter plate colorimetric assays, based on the increase in absorbance at 405 nm which occurs as dithionitrobenzoic acid (DTNB) is reduced by the enzyme-mediated transfer of reducing equivalents from NADPH, were used to measure TR/Trx-dependent insulin-reduction and TR activity (see, e.g., Kunkel et al., 1997).

Thioredoxin reductase/thioredox independent insulin reducing activity was measured in an incubation with a final volume of 60 μL containing 100 mM HEPES buffer, pH 7.2, 5 mM EDTA (HE buffer), 1 mM NADPH, 1.0 μM thioredoxin reductase, 0.8 μM thioredoxin, and 2.5 mg/ml bovine insulin in flat-bottom 96-well microtitre plates. Compounds were diluted in HE buffer and added to the wells as 20 μL aliquots. Incubations were for 30 min at 37° C. The reaction was stopped by the addition of 100 μL of 6 M guanidine HCl, 50 mM Tris, pH 8.0, and 10 mM DTNB, and the absorbance measured at 405 nm.

Assays of TR activity were run in flat-bottom 96-well microtitre plates in a final incubation volume of 60 μL containing HE buffer, 10 mM DTNB, 1.0 μM thioredoxin reductase, and 1 mM NADPH. Compounds were diluted in HE buffer and added to, the wells as aliquots. To ensure uniform coverage of the bottom of the well, the plate was briefly spun at 3000 g. To start the reaction, NADPH and DTNB were added as a 20 μL aliquots in HE buffer and the plate was moved to the plate reader preheated to 37° C. The optical density at 405 nm was measured every 10 s and initial linear reaction rates were determined. The data are summarised in Table 5.

TABLE 5

Inhibition of Thioredoxin/Thioredoxin Reductase (Tx/TR)-catalysed reduction of Insulin

| Compound | IC$_{50}$ | | Mean GI$_{50}$ (μM) |
|---|---|---|---|
|  | Tx/TR | TR |  |
| Q02 | 9.4 | >10 | 0.55 |
| Q05 | 12.2 | >10 | 0.29 |

Tuberculosis Activity

Compounds were submitted to the Tuberculosis Antimicrobial Acquisition and Coordinating Facility (TAACF) for testing as antimycobacterial drugs.

Compounds were subjected to in vitro evaluation for antimycobacterial activity.

Primary screening was conducted at 6.25 μg/mL (or molar equivalent of highest molecular weight compound in a series of congeners) against *Mycobacterium tuberculosis* H$_{37}$Rv (ATCC 27294) in BACTEC 12B medium using a broth microdilution assay, the Microplate Alamar Blue Assay (MABA) and the % inhibition reported. Compounds exhibiting fluorescence were tested in the BACTEC 460 radiometric system. See, for example, Collins et al., 1997. The minimum inhibitory concentration (MIC) is defined as the lowest concentration effecting a reduction in fluorescence of 90% relative to controls. The data are summarised in Table 6.

TABLE 6

In Vitro Anti-Mycobaterial Activity (MABA Assay)

| Cmpd. No. | % Inhibition | MIC (μg/mL) |
|---|---|---|
| Q01 | 100 | 1.56 |
| Q10 | 100 | 3.13 |
| Q25 | 100 | 1.56 |

TABLE 6-continued

In Vitro Anti-Mycobaterial Activity
(MABA Assay)

| Cmpd. No. | % Inhibition | MIC (µg/mL) |
|---|---|---|
| Q05 | 99 | 0.78 |
| Q14 | 99 | 3.13 |
| Q07 | 99 | 3.13 |
| Q04 | 99 | 1.56 |
| Q13 | 98 | 6.25 |
| Q03 | 98 | 3.13 |
| Q12 | 97 | 6.25 |
| Q17 | 96 | 6.25 |
| Q15 | 91 | 6.25 |
| Q09 | 89 | — |
| Q19 | 80 | — |
| Q30 | 45 | — |
| Q28 | 18 | — |
| Q08 | 17 | — |
| Q11 | 14 | — |
| Q17 | 8 | — |
| Q02 | 7 | — |
| Q22 | 2 | — |
| Q21 | 1 | — |
| Q29 | 0 | — |

Note that the most active compounds (e.g., at least the 10 most active listed above) have —OH groups on the quinol ring, that is, $R^O$ is —OH. Also note that the benzothiazolyl compounds, where $R^O$ is —OH (e.g., Q05), are more active than corresponding compounds where $R^O$ is —OR (e.g., Q17, Q15, Q19).

Additional Data

Recent unpublished studies by the inventors have shown that the benzothiazolyl acetoxy compound (Q15) is unstable in cell culture medium, and undergoes rapid hydrolysis (determined using HPLC analysis) to give the corresponding benzothiazolyl-substituted quinol (Q05), which retains anti-tumor activity.

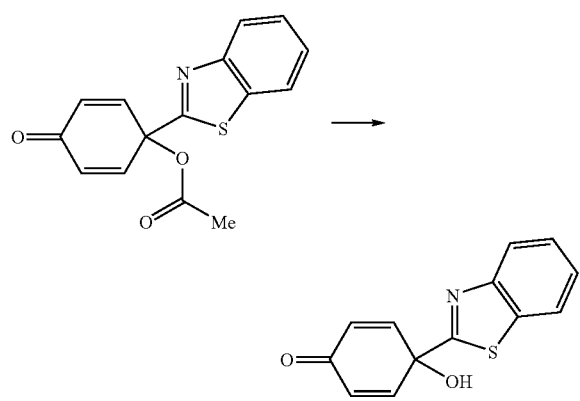

X-ray crystal structure determination of Q05 confirmed the tetrahedral geometry of the aryl group, Ar, attached to the quinol ring moiety; this arrangement is substantially different from the planar arrangment in the mechanistically unrelated 2-(4-aminophenyl)benzothiazoles.

Other biological properties of the compounds of the present invention (e.g., Q05) include:
  in vitro selectivity for certain colon and renal cells lines (NCI analysis: $\log_{10}LC_{50} < -6.0$);
  mean log10GI50 of −6.63;
  equi-potent MCF-7 wt and MCF-7/adr (breast cancer);
  equi-potent MCF-7 (wt p53) and MDS 468 (mut p53) (breast cancer);
  equi-active against $ZR^{75}$ clones expressing different levels of epidermal growth factor receptor (EGFR);
  lag phase (48 h), then induces apoptotic events;
  localised in nucleus (confocal microscopy);
  depletes cellular glutathione;
  up-regulates p53 in MCF-7 (breast cancer) and HCT 116 (colon cancer).

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Alcaraz, L., et al., 1998, "Manumycin A: synthesis of the (+)-enantiomer and revision of stereochemical assignment," J. Org. Chem., Vol. 63, pp. 3526–3527.

Alley et al., 1988, "Feasibility of drug screening with panels of human tumor cell lines using a microculture tetrazolium assay," Cancer Research, Vol. 48, p. 589.

Boyd, M. R., Paull, K. D., 1995, "Some practical considerations and applications of the National Cancer Institute in vitro anticancer drug discovery system," Drug Dev. Res., Vol. 34, pp. 91–104.

Callinan et al., 1990, "Spiro-annulated 2,5-cyclohexadienones via oxidation of 2'-alkenyl-p-phenyl phenols with iodobenzene diacetate," Tetraderon Letters, Vol. 31, No. 32, pp. 4551–4552.

Capparelli et al., 1987, "Structural and solvent/electrolyte effects on the selectivity and efficiency of the anodic oxidation of para-substituted aromatic ethers. An efficient route to quinol ether ketals and quinol ethers," J. Org. Chem., Vol. 52, pp 4953–4961.

Collins, L.; Franzblau, S. G.; 1997, "Microplate Alamar Blue Assay versus BACTEC 460 System for High-throughput Screening of Compounds against Mycobacterium tuberculosis and Mycobacterium avium," Antimicrob. Agents Chemother., Vol. 41, pp. 1004–1009.

Dengler et al., 1995, "Development of a propidium iodide fluorescence assay for proliferation and cytotoxicity assays," Anti-cancer drugs, Vol. 6, pp. 522–532.

Faaland et al., 1991, "Rapid uptake of tyrphostin into A431 human epidermoid cells is followed by delayed inhibition of epidermal growth factor (EGF) stimulated EFG receptor tyrosine kinase activity," Mol. Cell Biol., Vol. 11, pp. 2697–2703.

Gasdaska et al., 1994, "The predicted amino acid sequence of human thioredoxin is identical to that of the autocrine growth factor human adult T-cell derived cofactor (ADF): thioredoxin mRNA is elevated in some human tumors," Biochimica et Biophysica Acta, Vol. 1218, p. 292.

Geran et al., 1972, "Protocols for screening chemical agents and natural products against tumor and other biological systems," *Cancer Chemother. Rep.*, Vol. 3, p. 1–103.

Hutchinson et al., 2001, Antitumour benzothiazoles. 14. Synthesis and in vitro biological properties of flurorinated 2-(4-aminophenyl)benzothiazoles," *J. Med. Chem.*, Vol. 44, pp. 1446–1455.

Kirkpatrick et al., 1999, "Parallel synthesis of disulfide inhibitors of the thioredoxin redox system as potential antitumor agents," *Anti-Cancer Drug Design*, Vol. 14, pp. 421–432.

Kunkel et al., 1997, "Cell line-directed screening assay for inhibitors of thioredoxin reductase signaling as potential anti-cancer drugs," *Anti-Cancer Drug Design*, Vol. 12, pp. 659–670.

McKillop et al., 1993, "A concise synthesis of the novel antibiotic aranorosin," *Tetrahedron Lett.*, Vol. 34, pp. 5519–5522.

Milić, D. R., et al., "X-Ray crystal structure of 10β-hydroxy-4β,5β-epoxyestr-1-en-3,17-dione and antitumor activity of its congeners," *Molecules*, Vol. 4, pp. 338–352.

Oblong et al., 1993, "Purification of human thioreductase; properties and characterization by absorption and circular dichroism spectroscopy," *Biochemistry*, Vol. 32, p. 7271.

Pelter, A., Elgendy, S. M. A., 1993, "Phenolic oxidations with phenyliodonium diacetate," *J. Chem. Soc., Perkin Trans.* 1, pp. 1891–1896.

Powis, G., Mustacich, D, Coon, A., 2000, "The role of the redox protein thioredoxin in cell growth and cancer," *Free Radical Biology & Medicine*, Vol. 29, Nos. 3/4, pp. 312–322.

Rambas et al., 1994, "The degree of inhibition of protein tyrosine kinase activity by Tyrphostin 23 and 25 is related to their instability," *Cancer Research*, Vol 54, pp. 867–869.

Reddy et al., 1992, "Inhibition of breast cancer cell growth in vitro by a tyrosine kinase inhibitor," *Cancer Research*, Vol. 52, pp. 3631–3641.

Sonnenwirth, A. C., and Jarett, L. (eds.), Gradwohl's Clinical Laboratory Methods and Diagnosis, 8th edition, Vol. 2, p.1707.

Umezawa et al., 1991, "Use of erbstatin as protein tyrosine kinase inhibitor," *Methods Enzymol.*, Vol. 201, pp. 379–385.

Wada, H., et al., 1987, "Chemical and chemotaxonomical studies of ferns. LXXIII. New flavonoids with modified B-ring from the genus *Pseudophegopteris* (Thelypteridacae)," *Chem. Pharm. Bull.*, Vol. 35, pp. 4757–4762.

Weinstein, J. N., et al., 1997, "An information-intensive approach to the molecular pharmacology of cancer," *Science*, Vol. 275, pp. 343–349.

Wells et al., 06 Mar. 2000, "Antitumour benzothiazoles. Part 10: The synthesis and antitumour activity of benzothiazole substituted quinol derivatives," *Bioorganic & Medicinal Chemistry Letters*, Vol.10, No.5, pp. 513–515.

Wessely et al., 1952, "Uber die Einwirkung von metallorganischen Verbingungen auf Chinole I," *Monatsch. Chem.*, Vol. 83, pp. 1253–1261.

Wipf, P., et al., "Synthesis of the antitumor antibiotic LL-C10037α," *J. Org. Chem.*, Vol. 59, pp. 3518–3519.

The invention claimed is:

1. A compound selected from compounds having the following formula:

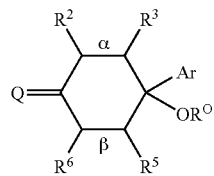

wherein:

Q is =O or =N—S(=O)$_2$—R$^Q$;

R$^Q$, if present, is —H or optionally substituted C$_{1-7}$alkyl, C$_{3-20}$heterocyclyl, or C$_{5-20}$aryl;

Ar is one of the following groups, and is optionally substituted:

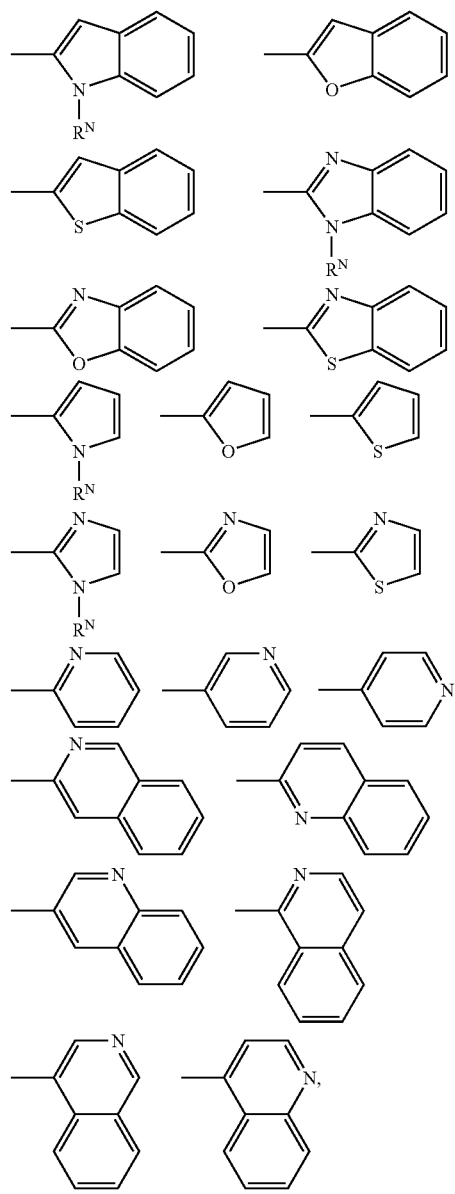

R$^N$ is —H, C$_{1-7}$alkyl, C$_{3-20}$heterocyclyl, or C$_{5-20}$aryl, $R^O$ is an oxy substituent and is —H or optionally substituted $C_{1-7}$alkyl, $C_{3-20}$heterocyclyl, $C_{5-20}$aryl, $C_{1-7}$alkyl-acyl, $C_{3-20}$heterocyclyl-acyl, or $C_{5-20}$aryl-acyl;
and wherein
either (i):
the bond marked α is a double bond;
the bond marked β is a double bond;
$R^3$ and $R^5$ are each independently ring substituents selected from: H, halo, —S— $C_{1-7}$alkyl, —S—$C_{1-7}$alkyl-$C_{5-20}$aryl, —S—$C_{5-20}$aryl, and amino acid thioether groups;
$R^2$ and $R^6$ are H;
or (ii):
the bond marked α is a single bond or a double bond;
the bond marked β is a single bond or a double bond;
$R^3$ and $R^5$ are each independently ring substituents selected from: H, halo, —S—$C_{1-7}$alkyl, —S—$C_{1-7}$alkyl-$C_{5-20}$aryl, —S—$C_{5-20}$aryl, and amino acid thioether groups;
but with the proviso that one or both of $R^3$ and $R^5$ is selected from: —S—$C_{1-7}$alkyl, —S—$C_{1-7}$alkyl-$C_{5-20}$aryl, —S—$C_{5-20}$aryl, and amino acid thioether groups;
$R^2$ and $R^6$ are H;
and pharmaceutically acceptable salts, esters, amides, solvates, and hydrates thereof;
with the proviso that, if Q is =O, α is a double bond, β is a double bond, each of $R^2$, $R^3$, $R^5$, and $R^6$ is —H; and Ar is benzothiazol-2-yl, then $R^O$ is other than: -Me, -Et, -Pr, —CH$_2$—C≡CH, and —C(=O)CH$_3$; and,
with the proviso that, if Q is =O, α is a double bond, β is a double bond, then Ar is other than: thiophenyl.

2. A compound according to claim 1, wherein Q is =O.

3. A compound according to claim 1, wherein Q is =N—S(=O)$_2$—$R^Q$, wherein $R^Q$ is —H or optionally substituted $C_{1-7}$alkyl, $C_{3-20}$heterocyclyl, or $C_{5-20}$aryl.

4. A compound according to claim 3, wherein $R^Q$ is selected from methyl, ethyl, phenyl, tolyl, and halo-substituted analogs thereof.

5. A compound according to claim 1, wherein $R^O$ is —H.

6. A compound according to claim 2, wherein $R^O$ is —H.

7. A compound according to claim 3, wherein $R^O$ is $C_{1-7}$alkyl; $C_{3-20}$heterocyclyl; $C_{5-20}$aryl; $C_{1-7}$alkyl-acyl; $C_{3-20}$heterocyclyl-acyl; or $C_{5-20}$aryl-acyl; and is optionally substituted.

8. A compound according to claim 2, wherein $R^O$ is $C_{1-7}$alkyl; $C_{3-20}$heterocyclyl; $C_{5-20}$aryl; $C_{1-7}$alkyl-acyl; $C_{3-20}$heterocyclyl-acyl; or $C_{5-20}$aryl-acyl; and is optionally substituted.

9. A compound according to claim 1, wherein $R^O$ is an amino-alkyl-acyl group of the formula —C(=O)-J-K, wherein J is a $C_{1-7}$alkylene group, and K is an amino group.

10. A compound according to claim 1, wherein $R^O$ is an amino-alkyl-acyl group of the formula —C(=O)(CH$_2$)$_n$—K, where n is an integer from 1 to 7, and K is an amino group.

11. A compound according to claim 2, selected from compounds having the following formula, and pharmaceutically acceptable salts, esters, amides, solvates, and hydrates thereof:

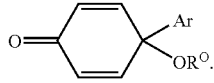

12. A compound according to claim 6, selected from compounds having the following formula, and pharmaceutically acceptable salts, esters, amides, solvates, and hydrates thereof:

13. A compound according to claim 1, selected from compounds having the following formula, wherein each of the ring substituents, $R^3$ and $R^5$, is other than —H, and pharmaceutically acceptable salts, esters, amides, solvates, and hydrates thereof:

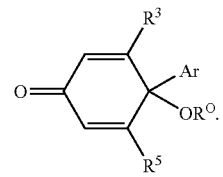

14. A compound according to 1, selected from compounds having one of the following formulae, wherein each of the ring substituents, $R^3$ and $R^5$, is other than —H, and pharmaceutically acceptable salts, esters, amides, solvates, and hydrates thereof:

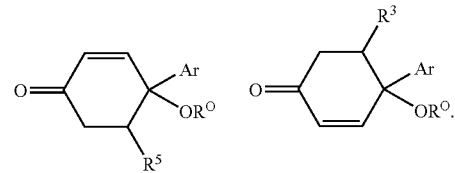

15. A compound according to claim 1, selected from compounds having the following formula, wherein each of the ring substituents, $R^3$ and $R^5$, is other than —H, and pharmaceutically acceptable salts, esters, amides, solvates, and hydrates thereof:

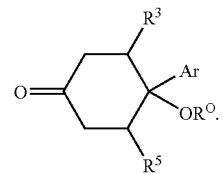

16. A compound according to claim 1, wherein:
the bond marked α is a double bond;
the bond marked β is a double bond;
$R^3$ and $R^5$ are each independently ring substituents selected from: H and halo;
$R^2$ and $R^6$ are H.

17. A compound according to claim 1, wherein:
the bond marked α is a double bond;
the bond marked β is a double bond;
$R^3$ and $R^5$ are each independently ring substituents selected from: H and Cl;

R² and R⁶ are H.

18. A compound according to claim 1, wherein:
the bond marked α is a single bond or a double bond;
the bond marked β is a single bond or a double bond;
R³ and R⁵ are each H or a ring substituent;
but with the proviso that one or both of R³ and R⁵ is a ring substituent;
wherein said ring substituent is independently selected from: —S—$C_{1-7}$alkyl, —S—$C_{1-7}$alkyl-$C_{5-20}$aryl, —S—$C_{5-20}$aryl, and amino acid thioether groups; and
R² and R⁶ are each independently H.

19. A compound according to claim 1, wherein:
the bond marked α is a single bond or a double bond;
the bond marked β is a single bond or a double bond;
R³ and R⁵ are each H or a ring substituent;
but with the proviso that one or both of R³ and R⁵ is a ring substituent;
wherein said ring substituent is independently selected from: —S-Et, —S—$CH_2$-Ph, —S-Ph,

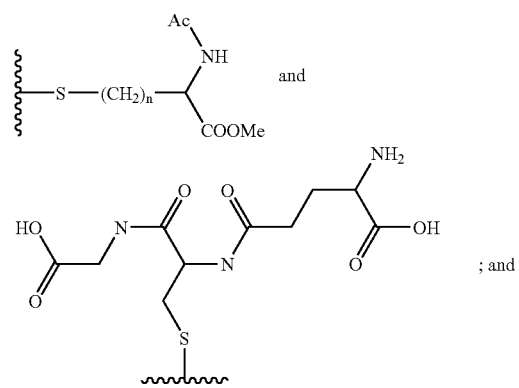

; and

R² and R⁶ are each independently H.

20. A compound according to claim 1, wherein Ar is one of the following groups, and is optionally substituted:

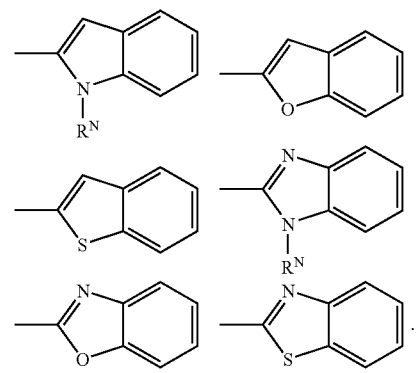

21. A compound according to claim 1, wherein Ar is one of the following groups, and is optionally substituted:

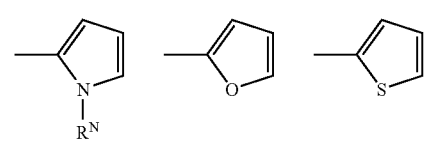

-continued

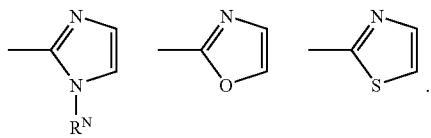

22. A compound according to claim 1, wherein Ar is one of the following groups, and is optionally substituted:

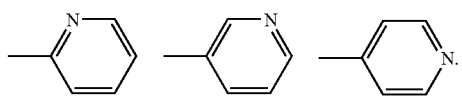

23. A compound according to claim 1, wherein Ar is one of the following groups, and is optionally substituted:

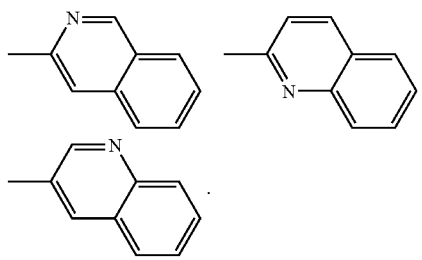

24. A compound according to claim 1, wherein Ar is one of the following groups, and is optionally substituted:

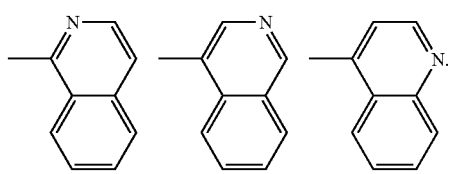

25. A compound according to claim 1, wherein Ar is the following group, and is optionally substituted:

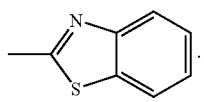

26. A compound according to claim 2, wherein Ar is the following group, and is optionally substituted:

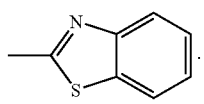

27. A compound according to claim 5, wherein Ar is the following group, and is optionally substituted:

28. A compound according to claim 6, wherein Ar is the following group, and is optionally substituted:

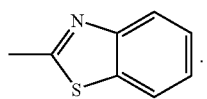

29. A compound according to claim 11, wherein Ar is the following group, and is optionally substituted:

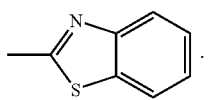

30. A compound selected from compounds having the following formula:

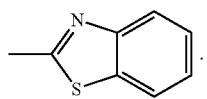

wherein Ar is the following group, and is optionally substituted:

and pharmaceutically acceptable salts, esters, amides, solvates, and hydrates thereof.

31. A compound according to claim 1, wherein Ar is substituted with one or more of: halo; hydroxy; ether; formyl; acyl; carboxy; ester; acyloxy; amido; acylamido; thioamido; tetrazolyl; amino; nitro; azido; cyano; cyanato; thiocyano; isothiocyano; sulfhydryl; thioether; sulfonic acid; sulfonate; sulfonyl; sulfonyloxy; sulfinyloxy; sulfamino; sulfonamino; sulfinamino; sulfamyl; sulfonamido; $C_{1-7}$alkyl; $C_{3-20}$heterocyclyl; and $C_{5-20}$aryl.

32. A compound according to claim 1, wherein Ar is substituted with one or more of: halo; hydroxy; ether; formyl; acyl; carboxy; ester; acyloxy; amido; acylamido; amino; sulfonyl; sulfonamido; $C_{1-7}$alkyl; $C_{3-20}$heterocyclyl; and $C_{5-20}$aryl.

33. A compound according to claim 1, wherein Ar is substituted with one or more of: halo; $C_{1-7}$alkyl; $C_{1-7}$haloalkyl; $C_{1-7}$alkoxy; $C_{1-7}$haloalkoxy; and sulfonyl.

34. A compound according to claim 1, wherein Ar is substituted with one or more of: —F, —Cl, —Br, —I, -Me, -Et, —CF$_3$, —CCL$_3$, —OMe, —OEt, —SO$_2$Me, and —SO$_2$Et.

35. A compound according to claim 30, wherein Ar is substituted with one or more of: halo; hydroxy; ether; formyl; acyl; carboxy; ester; acyloxy; amido; acylamido; thioamido; tetrazolyl; amino; nitro; azido; cyano; cyanato; thiocyano; isothiocyano; sulfhydryl; thioether; sulfonic acid; sulfonate; sulfonyl; sulfonyloxy; sulfinyloxy; sulfamino; sulfonamino; sulfinamino; sulfamyl; sulfonamido; $C_{1-7}$alkyl; $C_{3-20}$heterocyclyl; and $C_{5-20}$aryl.

36. A compound according to claim 30, wherein Ar is substituted with one or more of: halo; hydroxy; ether; formyl; acyl; carboxy; ester; acyloxy; amido; acylamido; amino; sulfonyl; sulfonamido; $C_{1-7}$alkyl; $C_{3-20}$heterocyclyl; and $C_{5-20}$aryl.

37. A compound according to claim 30, wherein Ar is substituted with one or more of: halo; $C_{1-7}$alkyl; $C_{1-7}$haloalkyl; $C_{1-7}$alkoxy; $C_{1-7}$haloalkoxy; and sulfonyl.

38. A compound according to claim 30, wherein Ar is substituted with one or more of: —F, —Cl, —Br, —I, -Me, -Et, —CF$_3$, —CCl$_3$, —OMe, —OEt, —SO$_2$Me, and —SO$_2$Et.

39. A compound selected from the following compounds, and pharmaceutically acceptable salts, esters, amides, solvates, and hydrates thereof:

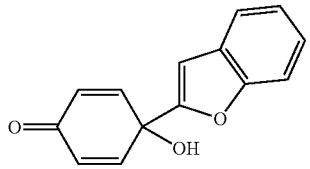

Q01

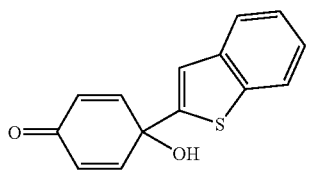

Q02

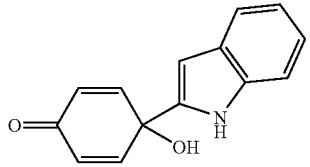

Q03

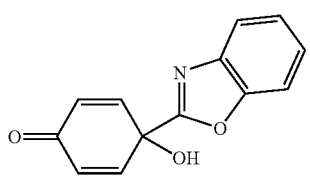

Q04

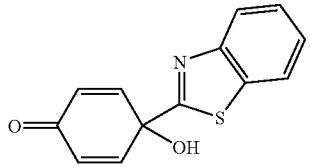

Q05

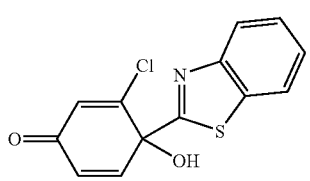

Q06

-continued
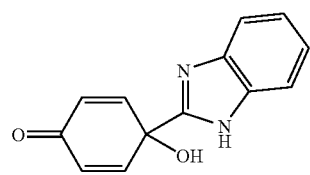 Q07
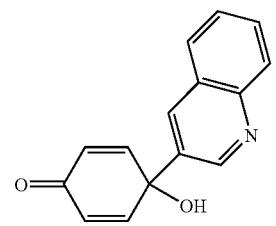 Q10
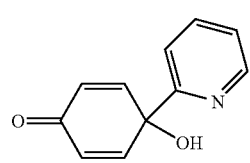 Q12
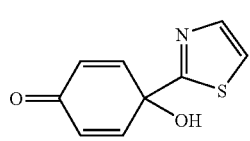 Q14
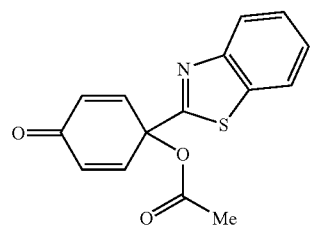 Q15
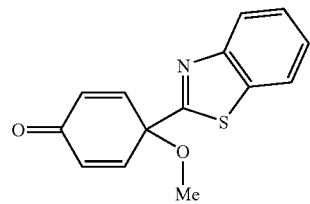 Q17
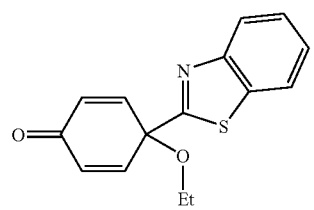 Q18
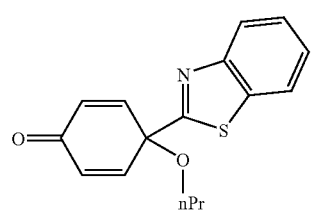 Q19
-continued
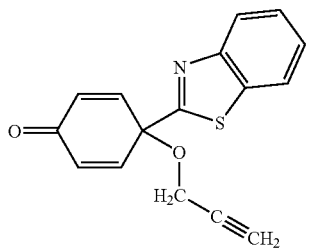 Q20
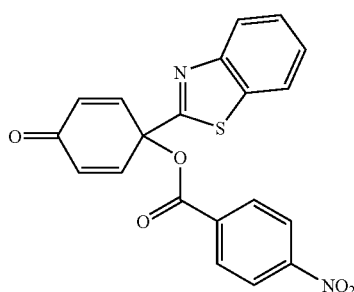 Q34
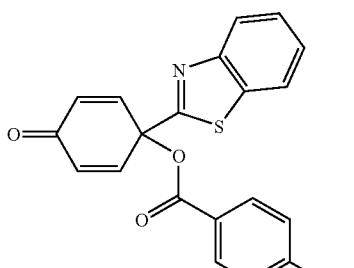 Q35
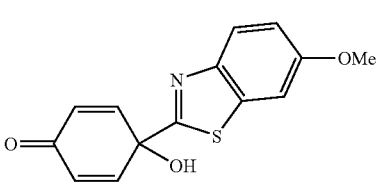 Q36
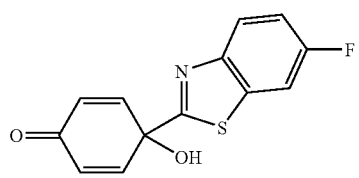 Q37
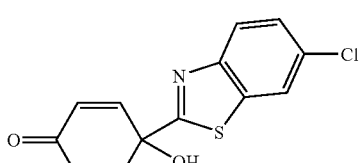 Q38
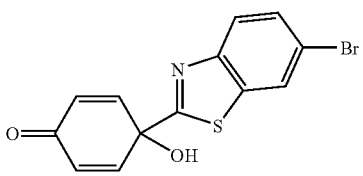 Q39

-continued
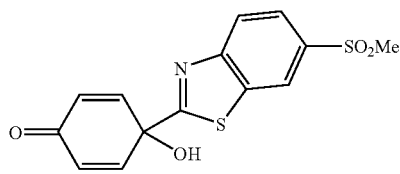 Q40
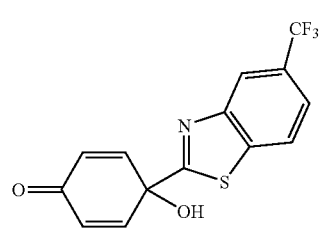 Q41
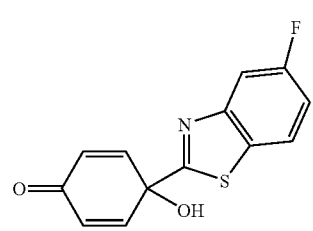 Q42
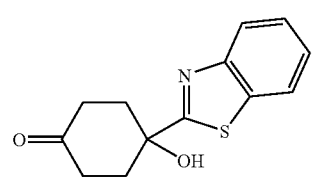 Q43
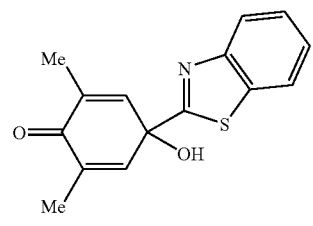 Q44
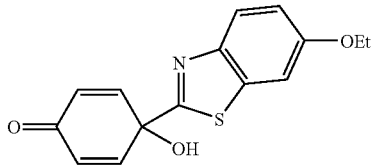 Q48
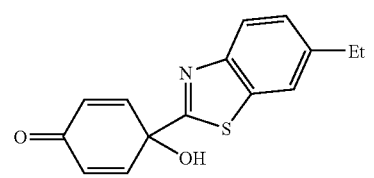 Q49
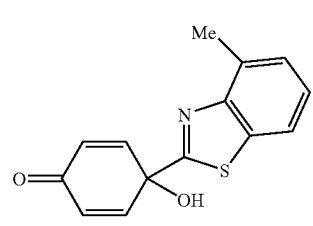 Q50
-continued
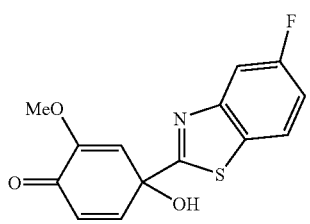 Q53
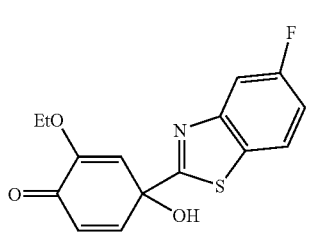 Q54.
40. A compound according to claim 1, selected from the following compounds, and pharmaceutically acceptable salts, esters, amides, solvates, and hydrates thereof:
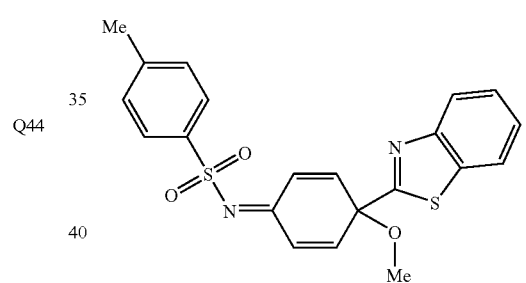 Q29
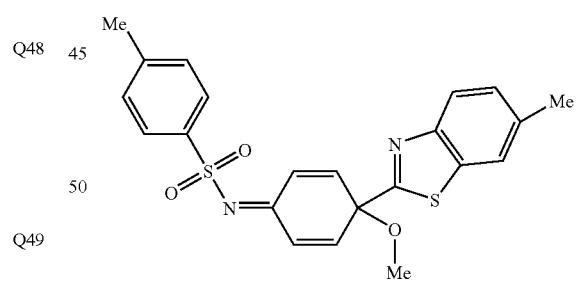 Q30
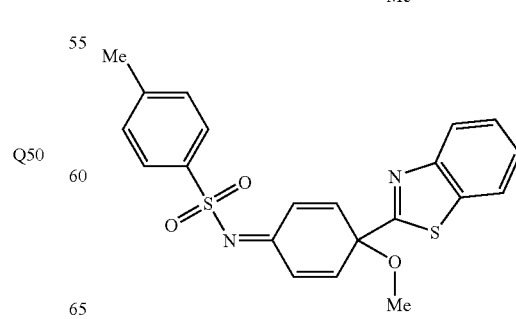 Q31

-continued

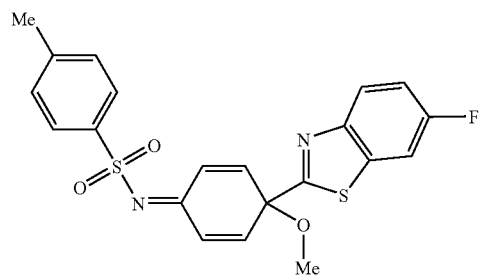

Q32

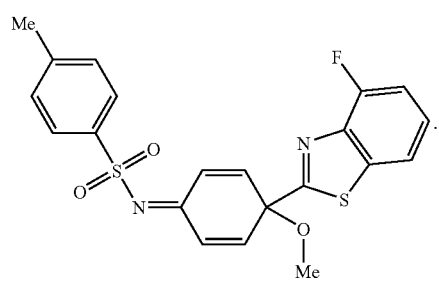

Q33

41. A compound according to claim 1, selected from the following compounds, and pharmaceutically acceptable salts, esters, amides, solvates, and hydrates thereof:

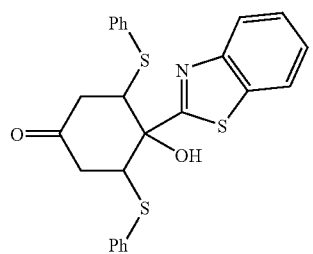

Q25

-continued

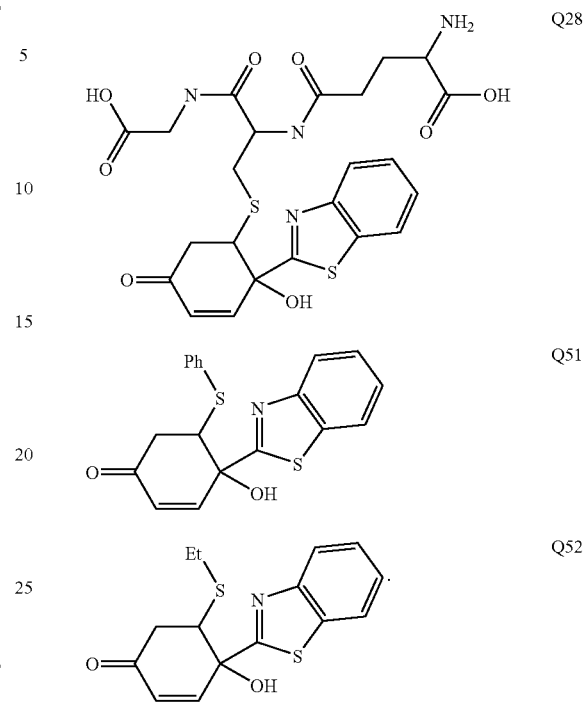

Q28

Q51

Q52

42. A composition comprising a compound according to claim 1 and a pharmaceutically acceptable carrier or diluent.

43. A composition comprising a compound according to claim 30 and a pharmaceutically acceptable carrier or diluent.

44. A method for the treatment of renal cancer comprising administering to a subject suffering from said cancer a therapeutically-effective amount of a compound according to claim 1.

45. A method for the treatment of renal cancer comprising administering to a subject suffering from said cancer a therapeutically-effective amount of a compound according to claim 30.

* * * * *